(12) United States Patent
Lang et al.

(10) Patent No.: US 10,139,418 B2
(45) Date of Patent: Nov. 27, 2018

(54) RAPID METHOD FOR TARGETED CELL (LINE) SELECTION

(75) Inventors: Dietmar Lang, Liverpool (GB); Elaine B. Martin, South Gosforth (GB); Gary A. Montague, Newcastle (GB); Christopher J. O'Malley, Newcastle (GB); Tracy S. Root, Slough (GB); Carol M. Trim, Ramsgate (GB); Jane F. Povey, Deal (GB); Christopher M. Smales, Chartham (GB); Andrew J. Racher, Brightwalton Newbury (GB)

(73) Assignee: LONZA BIOLOGICS PLC, Slough (GB)

(*) Notice: Subject to any disclaimer, the term of this patent is extended or adjusted under 35 U.S.C. 154(b) by 145 days.

(21) Appl. No.: 13/881,170

(22) PCT Filed: Oct. 27, 2011

(86) PCT No.: PCT/EP2011/005407
§ 371 (c)(1),
(2), (4) Date: Jul. 9, 2013

(87) PCT Pub. No.: WO2012/055554
PCT Pub. Date: May 3, 2012

(65) Prior Publication Data
US 2013/0295596 A1    Nov. 7, 2013

(30) Foreign Application Priority Data
Oct. 27, 2010   (EP) .................................. 10014005

(51) Int. Cl.
*G01N 27/62* (2006.01)
*G01N 33/68* (2006.01)
(Continued)

(52) U.S. Cl.
CPC ......... *G01N 33/6848* (2013.01); *G01N 27/62* (2013.01); *G01N 33/5005* (2013.01);
(Continued)

(58) Field of Classification Search
None
See application file for complete search history.

(56) References Cited

U.S. PATENT DOCUMENTS

2006/0151688 A1    7/2006  Castro-Perez et al.
2006/0257852 A1*  11/2006  Rappuoli ............. C07K 14/005
                                                              435/5

(Continued)

FOREIGN PATENT DOCUMENTS

EP    2216395 A1    8/2010

OTHER PUBLICATIONS

Lennart Eriksson, Henrik Antti, Johan Gottfries, Elaine Holmes, Erik Johansson, Fredrik Lindgren, Ingrid Long, Torbjörn Lundstedt, Johan Trygg, Svante Wold, Using chemometrics for navigating in the large data sets of genomics, proteomics, and metabonomics (gpm), 2004, Anal Bioanal Chem, vol. 380, pp. 419-429.*

(Continued)

*Primary Examiner* — Renee Claytor
*Assistant Examiner* — Trent Clarke
(74) *Attorney, Agent, or Firm* — Stephen T. Olson; Harness, Dickey & Pierce, P.L.C.

(57) ABSTRACT

The present invention relates to a process for the prediction of cell culture performance data of sample cells, a process for the isolation of said cells and a device for the prediction of cell culture performance data of sample cells.

14 Claims, 64 Drawing Sheets

(51) Int. Cl.
*G01N 33/50* (2006.01)
*H01J 49/00* (2006.01)
*H01J 49/16* (2006.01)
*H01J 49/40* (2006.01)

(52) U.S. Cl.
CPC ......... *H01J 49/0031* (2013.01); *H01J 49/164* (2013.01); *H01J 49/40* (2013.01)

(56) References Cited

U.S. PATENT DOCUMENTS

2008/0108553 A1   5/2008   Luan et al.
2011/0312087 A1  12/2011   Khan

OTHER PUBLICATIONS

NPL pdf document labeled "Surface Areas and Recommended Medium Volumes for Corning Cell Culture Vessels" downloaded from http://csmedia2.corning.com/LifeSciences/Media/pdf/cc_surface_areas.pdf accessed Jul. 9, 2016, online since Jun. 1, 2006 according to Google.*

NPL document "basic cho cell culture", a webpage from Pamela Stanley's lab accessible at http://stanxterm.aecom.yu.edu/wiki/index.php?page=basic_cho_cell_culture, accessed Jul. 9, 2016, online since Dec. 28, 2005 according to Google.*

International Search Report and Written Opinion regarding Application No. PCT/EP2011/005407, dated Jan. 13, 2012.

Feng, Hua-Tao et al: "Rapid characterization of high/low producer CHO cells using matrix-assisted laser desorption/ionization time-of-flight," Rapid Communications in Mass Spectrometry, vol. 24, No. 9, May 2010 (May 2010), pp. 1226-1230, XP002627392, ISSN: 0951-4198.

Reid, C. Q. et al: "Rapid whole monoclonal antibody analysis by mass spectrometry: An ultra scale-down study of the effect of harvesting by centrifugation on the post-translational modification profile," Biotechnology and Bioengineering Sep. 1, 2010, John Wiley and Sons Inc. USA. LNKD-DOI: 10.1002/BIT.2279, vol. 107, No. 1, Sep. 1, 2010, (Sep. 1, 2010), pp. 85-95, XP002627393, ISSN: 0006-3592.

Varghese, R. S. et al: "Analysis of LC-MS data for characterizing the metabolic changes in response to radiation," Journal of Proteome Research May 7, 2010, American Chemical Society USA LNKD-DOI: 10.1021/PR100185B, vol. 9, No. 5, May 7, 2010, (May 7, 2010), pp. 2786-2793, XP002627394, ISSN: 1535-3893.

Feng, Hua-Tao et al: "Rapid characterization of protein productivity and production stability of CHO cells by matrix-assisted laser desorption/ionization time-of-flight mass spectrometry," Rapid Communications in Mass Spectrometry: RCM May 30, 2011 LNKD-DOI: 10.1002/RCM.5011 PUBMED: 21504006, vol. 25, No. 10, May 30, 2011, (May 30, 2011), pp. 1407-1412, XP002635999, ISSN: 1097-0231.

Clare, J.J. et al: "High-Level Expression of Tetanus Toxin Fragment C in Pichia Pastoris Strains Containing Multiple Tandem Integrations of the Gene," Bio/Technology, Nature Publishing Co. New York, US, vol. 9, No. 5, May 1, 1991, (May 1, 1991), pp. 455-460, XP001019042, ISSN: 0733-222x, DOI: 10.38/NBT0591-455.

* cited by examiner

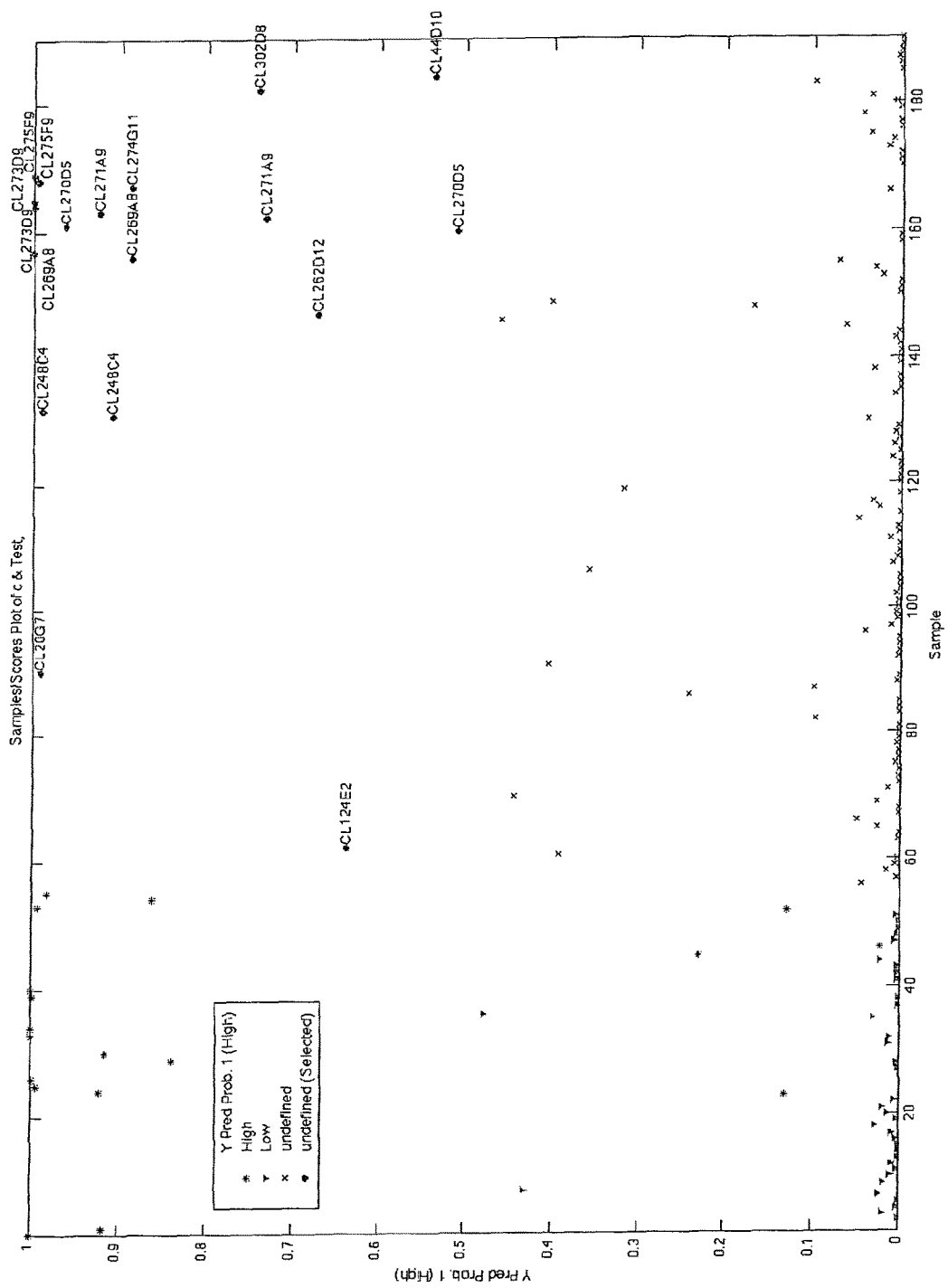

RAPID METHOD FOR TARGETED CELL (LINE) SELECTION

CROSS-REFERENCE TO RELATED APPLICATIONS

This application is a 371 U.S. National Stage of International Application No. PCT/EP2011/005407, filed Oct. 27, 2011. This application claims priority to European Patent Application No. 10014005.2, filed Oct. 27, 2010. The disclosures of the above applications are incorporated herein by reference.

The present invention relates to a process for the prediction of cell culture performance data of sample cells, a process for the isolation of said cells and a device for the prediction of cell culture performance data of sample cells.

According to the prior art methods for isolating recombinant mammalian cell lines with desired manufacturing properties are inefficient both in terms of resources and the ability to isolate specific combinations of desired characteristics.

For instance, Adrichem et al. (Anal. Chem., 1998, 70, 923-930) disclose investigations of protein patterns and mammalian cells in culture supernatants by matrix-assisted laser desorption/ionisation mass spectrometry (MALDI mass spectrometry). Said MALDI mass spectrometry can be used for protein profiling by monitoring proteins which have either been excreted into the media or located in cell lysates. The detectable mass range by MALDI mass spectrometry is from 16000 to several hundred thousands of Daltons, preferably from several hundred to several thousand. The results obtained thereby are complementary with standard SDS-PAGE electrophoresis. Therefore, these methods can be used for e.g. monitoring a large scale cultivation of hybridoma cells expressing an antibody of the IgG type.

Zhang et al. (J. Am. Soc. Mass Spectrom., 2006, 17, 490-499) disclose the identification of mammalian cell lines using MALDI-TOF and LC-ESI-MS/MS mass spectrometry. It is stated that MALDI-TOF mass spectrometry is effective for peptide profiling directly from single cell. LC-ESI-MS/MS analysis can provide useful sequence information after a tryptic digestion of sample cells. It was found to yield unique and reproducible MALDI-MS patterns, which can be used as a fingerprint to identify and distinguish the different cell lines measured. However, the obtained MS spectra were compared visually on basis of the clear visible MS peaks to distinguish the three different mammalian cell types. Alternatively, Zhang et al. demonstrate that a different technique—a combination of liquid chromatography followed by electrospray ionisation and tandem mass spectroscopy (LC-ESI MS/MS) for which it is necessary to digest the samples—is also useful to shed light on proteome profile differences.

Feng et al. (Rapid Commun. Mass Spectrom., 2010, 24, 1226-1230) disclose a rapid characterisation of high/low producer CHO cells using matrix-assisted laser desorption/ionisation time-of-light (MALDI-TOF). The process disclosed therein is able to distinguish between high and low producer cells when produced in the same culture at the same scale by applying two statistical methods, namely principle component analysis (PCA) and linear partial least squares (PLS), to analyse the MALDI-TOF spectra. Especially, the method according to Feng et al. allows distinguishing between productivity data from different cell lines producing a recombinant protein IFN-gamma at the same scale, i.e. grown at low scale. According to Feng et al. this approach could possibly be used to predict cell productivity.

The linear PLS used derives its usefulness from the ability to analyse data with many variables which is relevant to find cell lines subfamilies at a given scale.

As mentioned above the methods according to the prior art, especially to Feng et al., teach merely that MALDI-TOF data being analysed by statistical programs, namely PLS and PCA, can be used for differentiating between low and high producer cells at a given scale of culturing.

However, the prior art fails to teach a method which predicts the cell characteristics of an unknown cell at a later stage of up-scaling, in particular in large volume bioreactors, while these cells are still cultivated in a medium with a low volume. Especially, the known statistical programmes of PCA and PLS produce data being insufficient to be used as a basis for an accurate and reliable prediction of cell characteristics at a later state of up-scaling.

A cell line at the early stage expressing a specific balance of proteins can exhibit for instance a high productivity at this stage, but after up-scaling to bioreactor stage this productivity can be deteriorated due to different factors, which are inter alia shear forces, volume effects, different fermenter type or format, cultivation parameters, for example pH and gas-controlled cell density differences.

Therefore, there is a need for a method having the ability to rapidly screen large numbers of cell lines early in cell line development and cultured in small volumes only, which is able to predict the growth and specific production characteristics, for instance increased volumetric productivities, of said cell line at a given and desired culture scale, in particular in a bioreactor scale, that means in large volume scale.

Thus, the technical problem underlying the present invention is to provide a method to overcome the above identified problems, in particular to provide a method for the prediction of the cell culture, in particular bioreactor, performance of a cell with unknown cell characteristics, in particular already at an early state of up scaling, being additionally time-saving and cost-reducing, but having a high prediction accuracy for said performance in a large volume scale cultivation and/or under high productivity conditions, in particular in a bioreactor scale.

This problem is solved by the independent claims of the present invention.

Thus, the present invention provides a process, preferably an in vitro process, for the prediction of cell culture performance data of at least one sample cell comprising the steps:
  a) providing a probe of the at least one sample cell, preferably cultivated in a low volume of a medium, cell culture performance data from a standard cell and raw standard MS (mass spectrometry) data from a standard cell,
  b) subjecting the probe of the at least one sample cell to a MS analysis to obtain a raw sample MS data thereof,
  c) subjecting the raw standard and the raw sample MS data to at least one first MS signal processing method to obtain pre-treated standard and sample MS profiles and
  d) subjecting the cell culture performance data from the standard cell from step a) and the pre-treated sample and standard MS profiles obtained in step c) to a second MS signal processing method including, preferably to a data analysis comprising of, a PLS-DA (partially least squares-discriminant analysis) based comparative evaluation so as to predict the cell culture performance data of the at least one sample cell.

The present invention therefore provides an advantageous process for the accurate and reliable prediction of cell culture, preferably bioreactor, performance data of at least one sample cell with unknown cell culture, preferably bioreactor, performance data, which allows the time saving and cost-reducing prediction of particular cell culture, preferably bioreactor, performance data, such as the productivity of cells. The present invention not only provides such an advantageous process, but also provides a cell prepared, and in particular isolated, by said method, wherein said cell is particularly characterised by desired cell culture, preferably bioreactor, performance data, such as a high productivity. Furthermore, the present invention provides a device for the prediction of cell culture performance data capable of conducting the process of the present invention.

In contrast to the prior art which usually upscales from a 96 well plate first to a 24 well plate, then to a shake flask and finally to bioreactor scale, the present invention obviates the cultivation steps in a 24 well plate and in a shake flask. Directly after the prediction of the cell culture, preferably bioreactor, performance data of at least one sample cell cultivated in low volume, for instance in a 96 well plate, the cultivation in a bioreactor can be performed.

According to the present invention, the PLS-DA allows the separation of very specific classes of observations on the basis of one variable, so that with the use of PLS-DA the problem of productivity classification for cell lines is overcome and their cell culture, preferably bioreactor, performance at different scale can be predicted.

In the context of the present invention the cell culture performance data are preferably bioreactor performance data.

In the context of the present invention the term "a probe of the at least one sample cell" has the same meaning as the term "a sample of the at least one sample cell".

In the context of the present invention the term "bioreactor performance data" is understand to mean data on the behaviour and the characteristics of a cell, when said cell is cultivated or reproduced under a large volume condition and/or high productivity conditions, in particular in a bioreactor. The bioreactor performance data are preferably data on the individual and specific cell productivity for a specific cell product, e.g. protein, in particular antibody, antibody fragment or fused antibody, antibiotics, cultivation needs, growth or lifetime of said cell. In a preferred embodiment, the cell product is a protein, in particular an antibody, peptide, proteoglycan, glycoprotein, carbohydrate, lipid, antibiotic or hormone.

The term "standard cell" means a cell with known cell culture performance data, in particular known characteristics and behaviour at a given scale, preferably at a large volume scale and/or under high productivity conditions, in particular at a bioreactor scale. These known characteristics were measured and analysed by methods according to the state of the art. For instance, the cell productivity can be determined by ELISA (enzyme-linked immuno sorbent assay).

In the context of the present invention the term "sample cell" relates to a cell having at least one unknown cell culture performance data, in particular cell characteristic. Preferably, at least one characteristic of said sample cell is known.

In the context of the present invention the term "low volume of a medium" means that the medium preferably has a volume of preferably 1 µl to 100 l, preferably 1 µl to 90 l, preferably 1 µl to 80 l, preferably 1 µl to 70 l, preferably 1 µl to 60 l, preferably 1 µl to 50 l, preferably 1 µl to 40 l, preferably 1 µl to 30 l, preferably 1 µl to 20 l, preferably 1 µl to 10 l, preferably 1 µl to 5 l, preferably 1 µl to 4 l, preferably 1 µl to 3 l, preferably 1 µl to 2 l, preferably 1 µl to 1 l, preferably 1 µl to 0.5 l, preferably 1 µl to 0.4 l, preferably 1 µl to 0.3 l, preferably 1 µl to 0.2 l, preferably 1 µl to 0.1 l, preferably 1 µl to 90 ml, preferably 1 µl to 80 ml, preferably 1 µl to 70 ml, preferably 1 µl to 60 ml, preferably 1 µl to 50 ml, preferably 1 µl to 40 ml, preferably 1 µl to 30 ml, preferably 1 µl to 20 ml, preferably 1 µl to 10 ml, preferably 1 µl to 5 ml, preferably 1 µl to 4 ml, preferably 1 µl to 3 ml, preferably 1 µl to 2 ml, preferably 1 µl to 1 ml, preferably 1 to 999 µl, preferably 1 µl to 0.5 ml, preferably 1 µl to 0.4 ml, preferably 1 µl to 0.3 ml, preferably 1 µl to 0.2 ml, preferably 1 µl to 0.1 ml, preferably 1 µl to 50 µl, preferably 1 µl to 40 µl, preferably 1 µl to 30 µl, preferably 1 µl to 20 µl, preferably 1 µl to 10 µl, preferably from 20 to 90 µl, preferably 20 to 80 µl, preferably from 20 to 70 µl, preferably from 20 to 60 µl, preferably from 20 to 50 µl, preferably from 20 to 40 µl, preferably from 20 to 30 µl, preferably from 30 to 70 µl, preferably from 30 to 60 µl, preferably from 30 to 50 µl, preferably from 30 to 40 µl, preferably from 10 to 100 µl, preferably from 10 to 90 µl, preferably from 10 to 80 µl, preferably from 10 to 70 µl, preferably from 10 to 60 µl, preferably from 10 to 50 µl, preferably from 10 to 40 µl, preferably from 10 to 30 µl, preferably from 10 to 20 µl, preferably from 40 to 60 µl, preferably from 40 to 50 µl.

In the context of the present invention the term "early stage of up-scaling" is understood as a point of time where the cells are cultivated in a low volume of a medium as defined above.

In the context of the present invention the term "bioreactor" means a container capable of containing cells for the production of at least one desired cell product, which preferably enables a high productivity in terms of the production speed and/or amount of said desired cell product. In a particularly preferred embodiment the bioreactor is a device or system supporting a biologically active environment. In a particularly preferred embodiment a bioreactor of the present invention is a container suitable for industrial and commercial production of said cell product of interest. In a particularly preferred embodiment such a container is able to create cell culture conditions suitable for producing the cell product of interest with a high productivity. In a particularly preferred embodiment the bioreactor contains a volume of medium of at least 10 l, at least 20 l, at least 50 l, at least 100 l, at least 200 l, at least 300 l, at least 400 l, at least 500 l, at least 600 l, at least 700 l, at least 800 l, at least 900 l, at least 1000 l, in particular at least 2000 l, at least 3000 l or at least 4000 l, which is preferably termed to be a "large volume" or "large volume of a medium" as used herein.

In the context of the present invention the expression "and/or" used in between two elements is meant to designate that both elements linked by said term are referred to in a cumulative or alternative manner. Thus, the expression "A and/or B" encompasses the meanings "A or B" and "A and B", that means "any one of A, B or both".

Thus, the present invention provides a method which enables a person skilled in the art to predict the characteristics of at least one sample cell, especially at least one cell line, by providing in a first step a) a probe of at least one sample cell cultivated in a medium having a low volume and low cell concentration therein, preferably from $10^4$ to $10^8$, preferably from $10^4$ to $10^8$ viable cells/ml culture medium, the cell culture performance data of a standard cell and the raw standard MS data thereof. Subsequently, in a second step the at least one sample cell is analysed by a mass spectrometry method. In a third step both the raw MS data of the at least one sample cell and the standard cell are treated by a MS signal processing method so as to obtain pre-treated MS profiles of the at least one sample cell and standard cell. In a fourth step the cell culture performance data from the standard cell and the pre-treated sample and standard MS profiles are subjected to a statistical method, namely PLS-DA, preferably in combination with PCA. This statistical program is employed to compare and evaluate the pre-treated MS profiles of the sample cell to the pre-treated MS profiles of a standard cell.

In a preferred embodiment of the present invention in step a) a sample of the at least one sample cell is provided in order to be subjected to a MS analysis to obtain a raw sample MS data thereof in step b).

The term "a probe of the at least one sample cell" and the term "a sample of the at least one sample cell" means a defined number of sample cells, namely at least one sample cell.

Preferably, the sample is provided in step a) in a low volume of a medium and subjected to a MS analysis to obtain a raw sample MS data thereof.

In a preferred embodiment of the present invention, the concentration of the cells, preferably in the sample, is from $10^4$ to $10^8$, from $10^5$ to $10^7$, in particular from $10^6$ to $10^7$ viable cells/ml culture medium after finishing the cultivation.

The present invention enables the prediction of the cell culture, preferably bioreactor, performance data, e.g. the productivity, of the at least one sample cell being cultivated at an early stage of up-scaling. The method according to the present invention allows the rapid development of for instance highly productive cell lines and thereby reduces the costs of therapeutic protein manufacturing and speeds up the development of pharmaceuticals.

The present process provides a novel screening tool for identifying, preferably early in the product development cycle, i.e. in a phase where a culture medium with a volume of preferably 1 to 999 µl is used, cells, preferably cell lines, that have the desired properties, for instance a high volumetric productivity, in particular in large-scale bioreactors, in particular in bioreactors containing culture medium in a volume above 10 liter. Moreover, the method according to the present invention improves the probability of finding a cell, especially cell line, with specific cell characteristics, for instance comprising a high product productivity, preferably at least 1 g/l, preferably at least 5 g/l and most preferably 10 g/l, early in development. In addition to identifying valuable cells, preferably cell lines, the method can also be used preferably for isolating new host cells, preferably cell lines, with improved properties for instance for therapeutic protein manufacturing, especially monoclonal antibody manufacturing. In particular, by the combination of the MS analysis with the statistical method of PLS-DA, preferably by the combination of PLS-DA with PCA (principle component analysis), the present process allows the identification of patterns in different product productivity levels as to predict the productivities at different scale therefrom in a fast and, if applicable, an automatic way.

In a preferred embodiment of the present invention the cell specific productivity, preferably high product productivity of the cells, is at least 0.1 g/l/h, preferably at least 1 g/l/h, preferably at least 5 g/l/h, preferably at least 10 g/l/h and most preferably 10 g/l/h.

The high probability of finding high producing cells, preferably cell lines, has the potential to reduce the number of cells, preferably cell lines, that needed to be screened before one suitable for manufacturing is identified. By reducing the number of screened cells, preferably cell lines, the materials required are reduced. Consequently, fewer resources will be required during the cell, preferably cell line, construction with concomitant generation of less waste materials. Higher producing cells, preferably cell lines, will reduce the number of bioreactor cultures required to supply the market requirements for the product. The present process is able to reduce the raw material requirements, in particular costs, of the production process, especially water that is used both as a raw material and in cleaning and sanitisation of the equipment.

In a preferred embodiment of the present invention the cell culture performance data, preferably the bioreactor performance data, reflects the performance of the cells, preferably of the sample cells and/or the standard cells, in a large volume.

In a preferred embodiment of the present invention the cell culture, preferably bioreactor, performance data is cell specific productivity, integral viable cell count or cell product concentration, in particular are cell specific productivity, integral viable cell count or cell product concentration data.

In a particularly preferred embodiment the cell culture, preferably bioreactor, performance data is the cell specific productivity (qP).

In a particularly preferred embodiment the cell culture, preferably bioreactor, performance data is the integral viable cell count data (IVC).

In a particularly preferred embodiment the cell culture, preferably bioreactor, performance data is the cell product concentration data.

In a preferred embodiment of the present invention the cell product concentration data is the titre data of the cell product.

The term "titre" means the concentration of a medium, preferably of a cell culture medium, preferably in a bioreactor, as determined by titration.

In a preferred embodiment of the present invention data on the production stability of cells is not understood as cell culture performance data.

In a preferred embodiment of the present invention the sample cell and/or standard cell is selected from the group consisting of human cell lines, animal cell lines, plant cell lines, antibodies, cells from fungi, cells from bacteria, cells from yeast and stem cells.

In a preferred embodiment of the present invention both the sample cell and the standard cell is selected from the same cell type, especially cell line or strain.

In a preferred embodiment of the present invention the sample cell is a CHO cell line, preferably a CHO-K1 cell line, preferably a modified CHO-K1 cell line. In a preferred embodiment of the present invention the standard cell is also a CHO cell line, preferably a CHO-K1 cell line (ATCC Number: CCL-61™), preferably a modified CHO-K1 cell line.

A CHO-K1 cell line is a subclone of the parental CHO cell line, which was derived from the ovary of an adult Chinese hamster. CHO-K1 cells require proline due to the absence of the gene for proline synthesis, with the block in the biosynthetic chain occurring in the step converting glutamic acid to glutamine γ-semialdehyde.

In a preferred embodiment of the present invention at least one part, preferably all of the standard cells express different cell products, preferably proteins, preferably antibodies compared to the at least one sample cell.

In a preferred embodiment of the present invention the cell line construction of at least one part, preferably all of the standard cells is different to that of the at least one sample cell.

In a preferred embodiment of the present invention the MS analysis used in step b) is selected from the group consisting of MALDI-TOF, LC-ESI-MS (liquid chromatography electrospray ionisation mass spectrometry) and LC-ESI-MS/MS (liquid chromatography coupled to tandem mass spectrometry with electrospray ionization).

In a preferred embodiment of the present invention the MS analysis used in step b) is MALDI-TOF. The sample cells subjected to MALDI-TOF need not to be digested by e.g. trypsin, but can be embedded into the matrix in intact form by a very simple preparation of the cells.

In a preferred embodiment of the present invention the MS analysis used in step b) is LC-ESI-MS. LC-ESI-MS analysis provides a particular great discrimination between cell lines in terms of productivity, growth and other desirable characteristics. The LC-ESI-MS analysis provides an extra dimension of information.

In a preferred embodiment of the present invention the raw standard MS data is obtained by MS analysis selected from the group consisting of MALDI-TOF, LC-ESI-MS and LC-ESI-MS/MS, preferably MALDI-TOF.

In a preferred embodiment of the present invention, the ionisation used for MALDI-TOF MS or LC-ESI-MS is carried out in a negative or positive reflection mode or in a positive or negative linear mode being optimal according to instrument-specific parameters, for example being device-dependent, with or without mass suppression and pulsed ion extraction.

In a preferred embodiment of the present invention, the following settings of the MALDI-TOF mass spectrometer instrument are used for the method according to the present invention:
Polarity: +ve
Suppress at: 1000 Da (Daltons)
Range: 1000 to 50000 Da In a preferred embodiment of the present invention the mass suppression during the MS analysis of MALDI-TOF and LC-ESI-MS is below 500 Da, preferably below 1000 Da and most preferred below 1500 Da.

In a preferred embodiment of the present invention the mass suppression during the MS analysis of MALDI-TOF and LC-ESI-MS is above 500 Da, preferably above 1000 Da and most preferred above 1500 Da.

In a preferred embodiment of the present invention the detected range during the MS analysis of MALDI-TOF and LC-ESI-MS is 200 to 100000 Da, preferably 200 to 60000 Da, preferably 500 to 50000 Da, preferably 1000 to 100000 Da, 1000 to 18000 Da, preferably 500 to 10000 Da and most preferably 200 to 8000 Da.

In a preferred embodiment of the present invention, the at least one sample cell is washed, preferably with a buffer solution, before being subjected to the MS analysis, preferably to MALDI-TOF.

In a preferred embodiment of the present invention the at least one sample cell is washed either with phosphate buffered saline (PBS) alone or followed by an aqueous sucrose solution wash step, in particular with 0.2 to 0.7 M, preferably 0.3 to 0.5 M, preferably 0.35 M sucrose before being subjected to the MS analysis, preferably to MALDI-TOF.

In a preferred embodiment of the present invention, the matrix used for the MALDI-TOF analysis is sinapinic acid (SA). According to the present invention the use of sinapinic acid (SA) as a matrix for the MALDI-TOF MS analysis provides advantageous spectra with a particular wide range of peaks, preferably up to 70 kDa, and being particularly well resolved. In a further embodiment of the present invention 2,5-dihydroxybenzoic acid (DHB) can also be used as a matrix.

In a preferred embodiment of the present invention the probe of the at least one sample cell subjected in step b) comprises not more than $1 \times 10^6$ cells, preferably $0.015 \times 10^6$ to $0.0625 \times 10^6$ cells, in particular $0.03 \times 10^6$ cells.

In a preferred embodiment of the present invention the MS profiles are taken after 1 to 5 hours, preferably 1 to 4 hours, in particular 1 to 3 hours of acclimatisation at low temperature, for instance at 0 to 10° C., preferably at 2 to 8° C., in particular at 4° C., resulting in the best reproducibly and a lower signal to noise-containing mass spectra.

In a preferred embodiment of the present invention the sample cells are subjected to the MS analysis at a specific time of growth. The preferred sampling times are mid and/or end log phase of the cell growth.

In a preferred embodiment of the present invention the raw sample MS data obtained in step b) and/or the raw standard MS data provided in step a) are signal processed by an operation selected from the group consisting of baseline correction, normalisation, alignment, filtering and cropping.

In a preferred embodiment, the first MS signal processing method used in step c) is selected from the group consisting of baseline correaction, normalisation, alignment, filtering and cropping.

MS data profiles typically exhibit a varied baseline due to issues such as chemical noise in the MALDI matrix and ion overloading. This is undesirable when using data analysis techniques to compare MS profiles as their utilised distance matrix to measure the similarity between profiles. Therefore, in a preferred embodiment of the present invention the raw sample and/or standard MS data are signal processed by the operation of baseline correction.

Another commonly observed phenomenon with MS profiles is the variation in the amplitude of the ion intensities. This can be caused by a number of factors, such as variation in the sample preparation or changes in the sensitivity over the instrument. Therefore, in a preferred embodiment of the present invention the raw sample and/or standard MS data are signal processed by the operation of normalisation.

Peak alignment is used to correct variation between the observed M/Z value and the true time of flight. These errors usually occur as a result of calibration errors and can be observed as a systematic shift between peaks. Therefore, in a preferred embodiment of the present invention the raw sample and/or standard MS data are signal processed by the operation of peak alignment.

Filtering of the MS profiles is carried out by smoothing the signal preferably by a Savitzky-Golay filter. Therefore, in a preferred embodiment of the present invention the raw sample and/or standard MS data are signal processed by the operation of filtering.

Cropping the MS profiles is performed to remove parts of the signal containing little or no information. Preferably the range of 0 to 500 m/z units is removed from the MS spectra. Therefore, in a preferred embodiment of the present invention the raw sample and/or standard MS data are signal processed by the operation of cropping.

In a preferred embodiment of the present invention the probe of the at least one sample cell is re-sampled. This specific preferred process step allows up-sampling and down-sampling of the original signal, whilst preserving the information contained within the spectra, i.e. altering the amounts channels of different data points measured. Typically, re-sampling is utilised in situations where the original high resolution MS signal would be considered impractical to work with due to computational constraints such as lack of computer memory. Re-sampling can also be used to create a consistent m/z range, which facilitates lining up multiple spectra.

In a preferred embodiment of the present invention the sample of the at least one sample cell is up-sampled to at least 50,000, preferably to account for slight differences in m/z vector.

In a preferred embodiment of the present invention the raw standard and sample MS data are visually analysed.

In a preferred embodiment of the present invention the pre-treated standard and sample MS profiles obtained in step c) are optically analysed, preferably to detect outlier and to remove unusual, defective pre-treated standard and sample MS profiles.

In a preferred embodiment, the first MS signal processing method used in step c) comprises, preferably in the following order, the following steps of resampling, baseline correction, filtering, alignment, visual analysing and normalisation of the raw standard and/or sample MS data.

In a preferred embodiment of the present invention the sample cell with the predicted cell culture, preferably bioreactor, performance data evaluated in step d) is cultivated in a cell culture, preferably bioreactor, so as to verify its cell culture, preferably bioreactor, performance data.

In a preferred embodiment of the present invention the raw sample MS profiles obtained in step b) and the verified bioreactor performance data of the sample cell are used in step a) as standard MS data and bioreactor performance data from the standard cell. By providing a higher number of MS profiles from standard cells with their known cell culture, preferably bioreactor, performance data the probability, preferably reliability, of the prediction is more accurate and dependable.

In a preferred embodiment of the present invention the PLS-DA model according to step (d) requires two different sets of information, namely the x-block and the y-block. In a preferred embodiment of the present invention the x-block contains the information from within the pre-treated sample MS data generated at the 96 DWP (deep well plate) stage of the process. In a preferred embodiment of the present invention each pre-treated sample MS data is treated as a sample, with the signal intensities recorded over a specific range of m/z values being treated as the variables. In a preferred embodiment of the present invention the y-block contains information assigning each of the pre-treated standard MS data to a class variable. In a preferred embodiment of the present invention the y-block contains information preferably relating to specific measures of productivity of a cell line at the bioreactor scale, that means product concentration, specific productivity or integral of viable cell count.

In a preferred embodiment of the present invention the statistical program PLS-DA is not applied to differentiate stable and unstable cell lines. In a preferred embodiment of the present invention the statistical program PLS-DA is the only statistical program used in the process according to the present invention. In a preferred embodiment of the present invention the statistical programs PLS-DA and PCA are the only statistical programs used in the process according to the present invention. Preferably, the raw standard and raw sample MS data are pre-treated in step c) without the usage of a statistical analysis, preferably PLS, before being subjected in step d) to a second MS signal processing method including a PLS-DA-based comparative evaluation as to predict the cell culture performance data of at least one sample cell.

In a preferred embodiment of the present invention using the x-block data, a PLS mapping of the original variables into the latent variable space is performed. This has the effect of reducing the dimensionality of the problem, whilst describing as much of the variability in the original data as possible. In a preferred embodiment of the present invention the PLS-DA algorithm utilises the information in the y-block to fit the linear discrimination boundary that best separates the x-block data based on the class information stored in the y-block. If there are only two classes described in the y-block, a single discrimination boundary is sufficient. In cases where three or more classes are present, the within class samples should be compared to the out of class samples for each available class.

In a preferred embodiment of the present invention the following classes are used in the PLS-DA based comparative evaluation to predict the integral viable cell count data:
High>$4500 \times 10^6$ cells×h/ml,
$4500 \times 10^6$ cells×h/ml>Medium>$3250 \times 10^6$ cells×h/ml and
Low<$3250 \times 10^6$ cells×h/ml.

In a preferred embodiment of the present invention the following classes are used in the PLS-DA based comparative evaluation to predict the cell specific productivity data:
High>2.35 pg×cell×h,
2.35 pg×cell×h>Medium>1.75 pg×cell×h and
Low<1.75 pg×cell×h.

In a preferred embodiment of the present invention the following classes are used in the PLS-DA based comparative evaluation to predict the cell product concentration data:
High>4 g/l and
Low<4 g/l The present invention relates also to a process for the production of a cell product, preferably a protein, from a cell comprising the steps:
a) predicting the cell culture performance data according to a method of the present invention,
b) identifying the sample cells with the desired cell culture performance data,
c) cultivating said sample cells identified in step b), preferably in a large volume of a medium, and
d) obtaining the cell product, preferably the protein, produced by the cultivation in step c).

Preferably, in the process for the production of a cell product, preferably a protein, the sample cell which cell culture performances data are predicted in step a) is cultivated in a low volume of a medium.

Furthermore, the present invention provides a process for the preparation, in particular isolation, of a cell with desired cell culture, preferably bioreactor, performance data, wherein the process for the prediction of cell culture, preferably bioreactor, performance data of at least one sample cell is performed and the at least one desired cell is prepared, preferably isolated.

The present invention provides a cell obtained, in particular isolated, by a process according to the present invention.

In a preferred embodiment of the present invention the cell isolated is characterised by a protein productivity of at least 1 g/l, preferably at least 5 g/l, preferably at least 6, 7, 8, 9 or preferably at least 10 g/l.

In a preferred embodiment of the present invention the cell isolated is characterised by a protein productivity of at least 0.1 g/l/h, preferably at least 1 g/l/h, preferably at least 5 g/l/h, preferably at least 6, 7, 8, 9 or preferably at least 10 g/l/h.

In a preferred embodiment of the present invention the cell isolated is characterised by a protein productivity of at least 0.1 g/l/h/cell, preferably at least 1 g/l/h/cell, preferably at least 5 g/l/h/cell, preferably at least 6, 7, 8, 9 or preferably at least 10 g/l/h/cell.

The present invention solves its underlying problem also by a device for the prediction of cell culture, preferably bioreactor, performance data of at least one sample cell, preferably adapted to providing a prediction of cell culture performance data, preferably when supplied with a probe of at least one sample cell, comprising: a) a means adapted for subjecting a probe of the at least sample cell to a MS (mass spectrometric) analysis to obtain a raw sample MS data thereof, (b) a means adapted for subjecting a raw standard and the raw sample MS data to at least one first MS signal processing method to obtain pre-treated standard and sample MS profiles and (c) a means adapted for subjecting cell culture, preferably bioreactor, performance data from a standard cell and the pre-treated sample and standard MS profiles to a second MS signal processing method including a PLS-DA (partial least square discriminant analysis) based comparative evaluation so as to predict the bioreactor performance data of the sample cell.

Further preferred embodiments are the subject matter of the subclaims.

The present invention is further illustrated by way of the following examples and the corresponding figures.

FIGS. 16a, 16b, 46 and 47 show PLSDA loading plots: (16a, 46) latent variable 1 and (16b, 47) latent variable 2.

Figure 17:
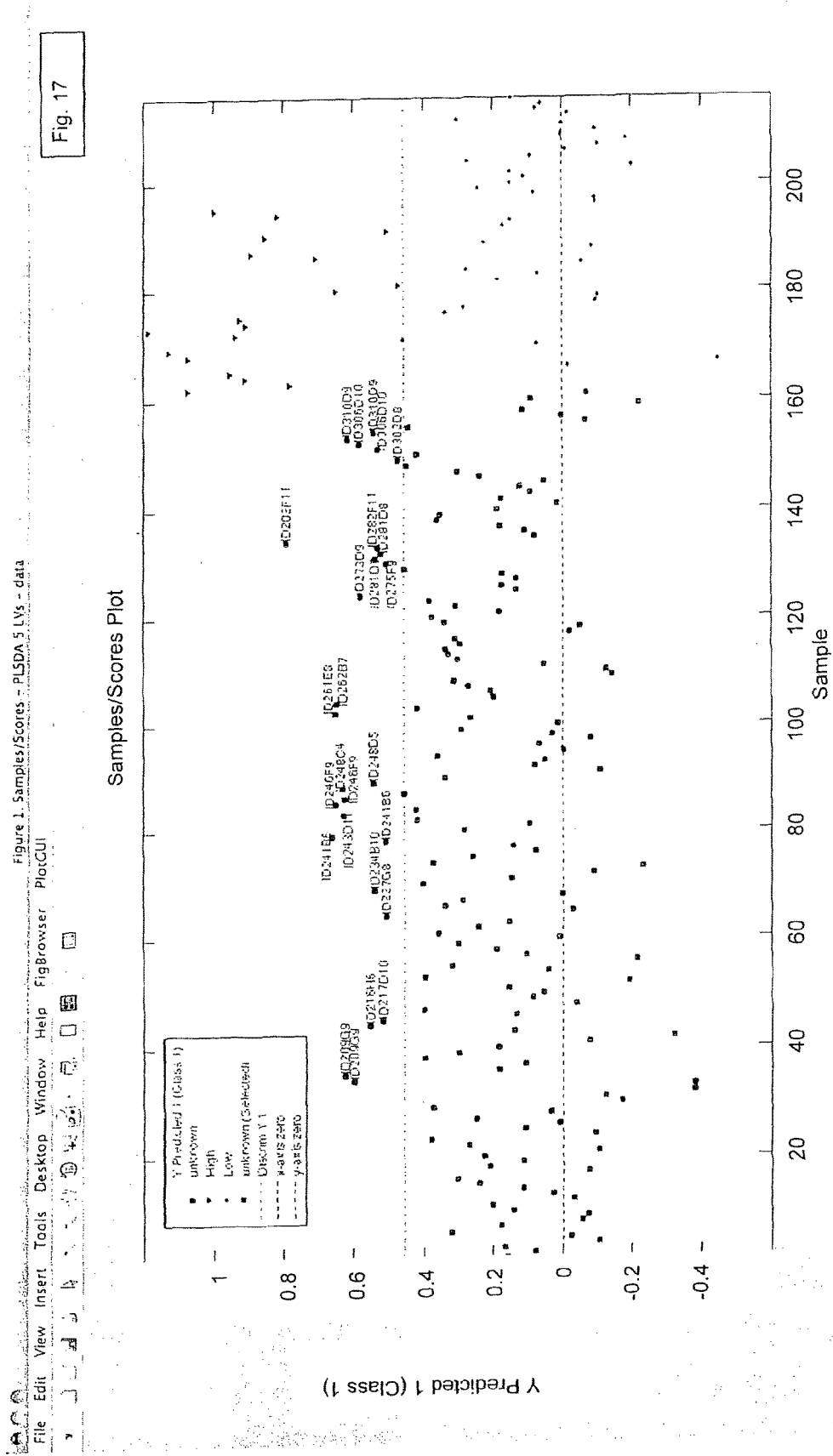
Figure 48:
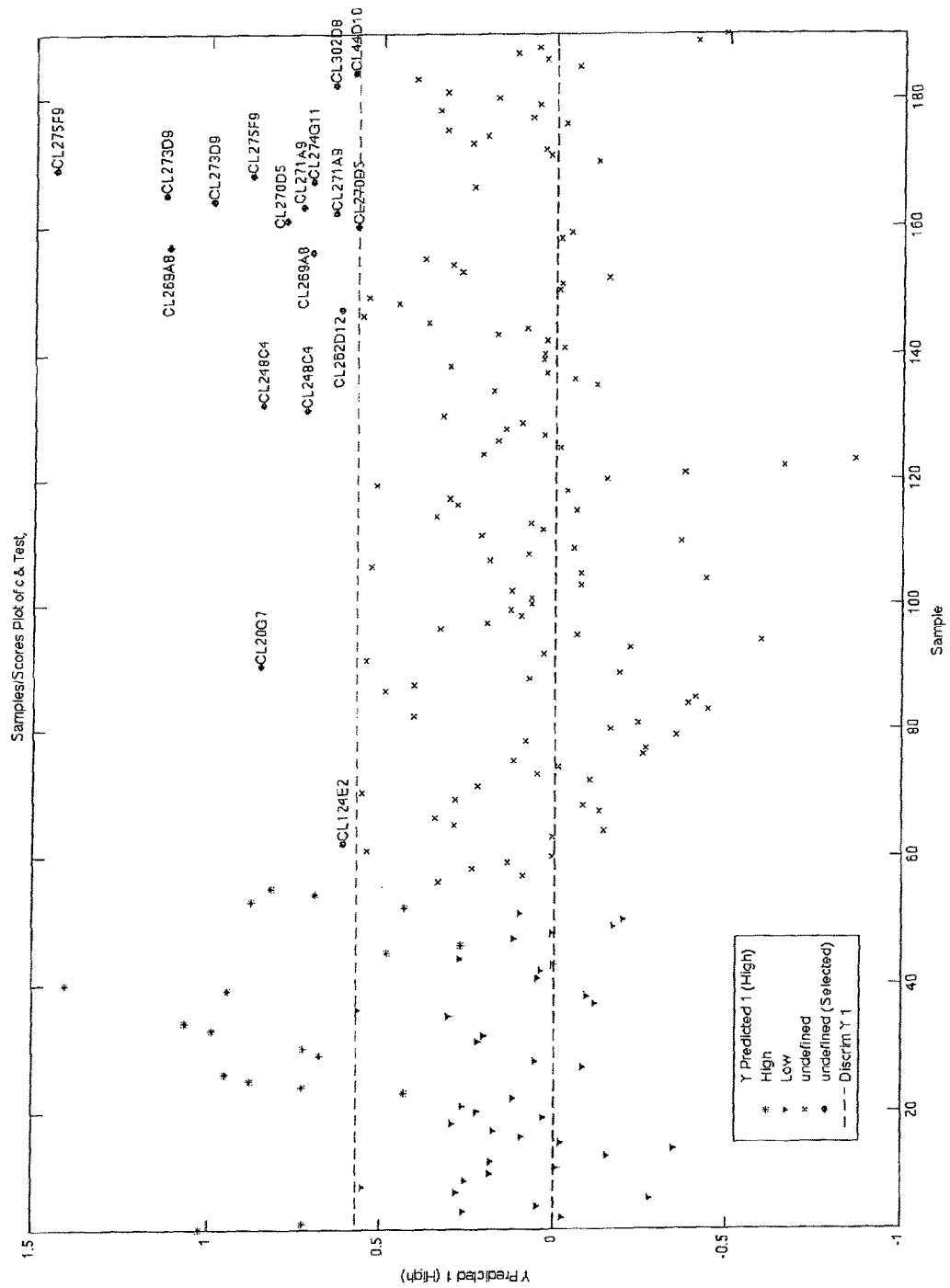

FIGS. 17 and 48 show PLSDA decision boundary plot for Ypredicted Class 1.

Figure 18:
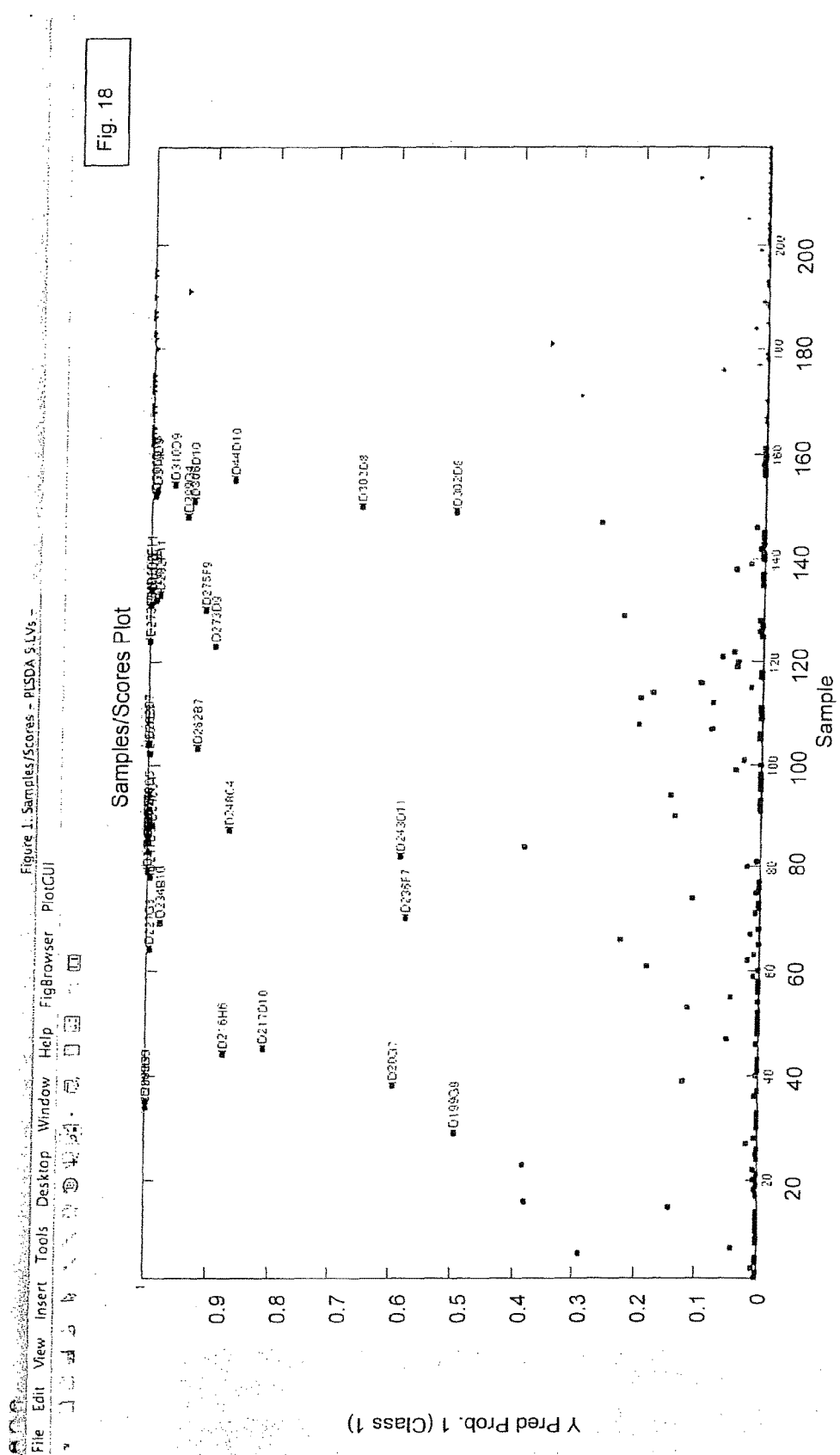

FIGS. 18 and 49 show a PLSDA probability plot for Ypredicted Class 1.

Figure 19A:
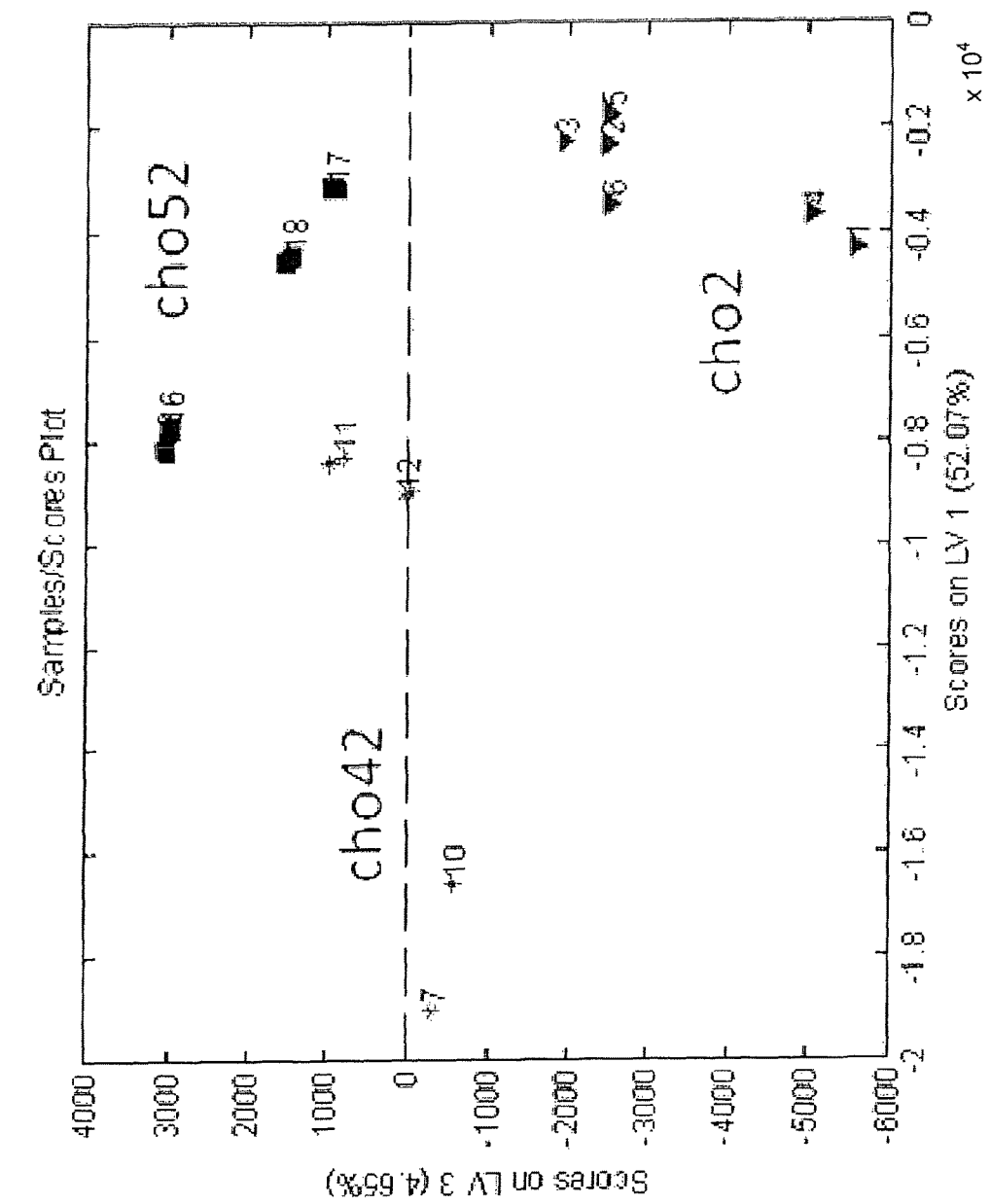
Figure 19B:
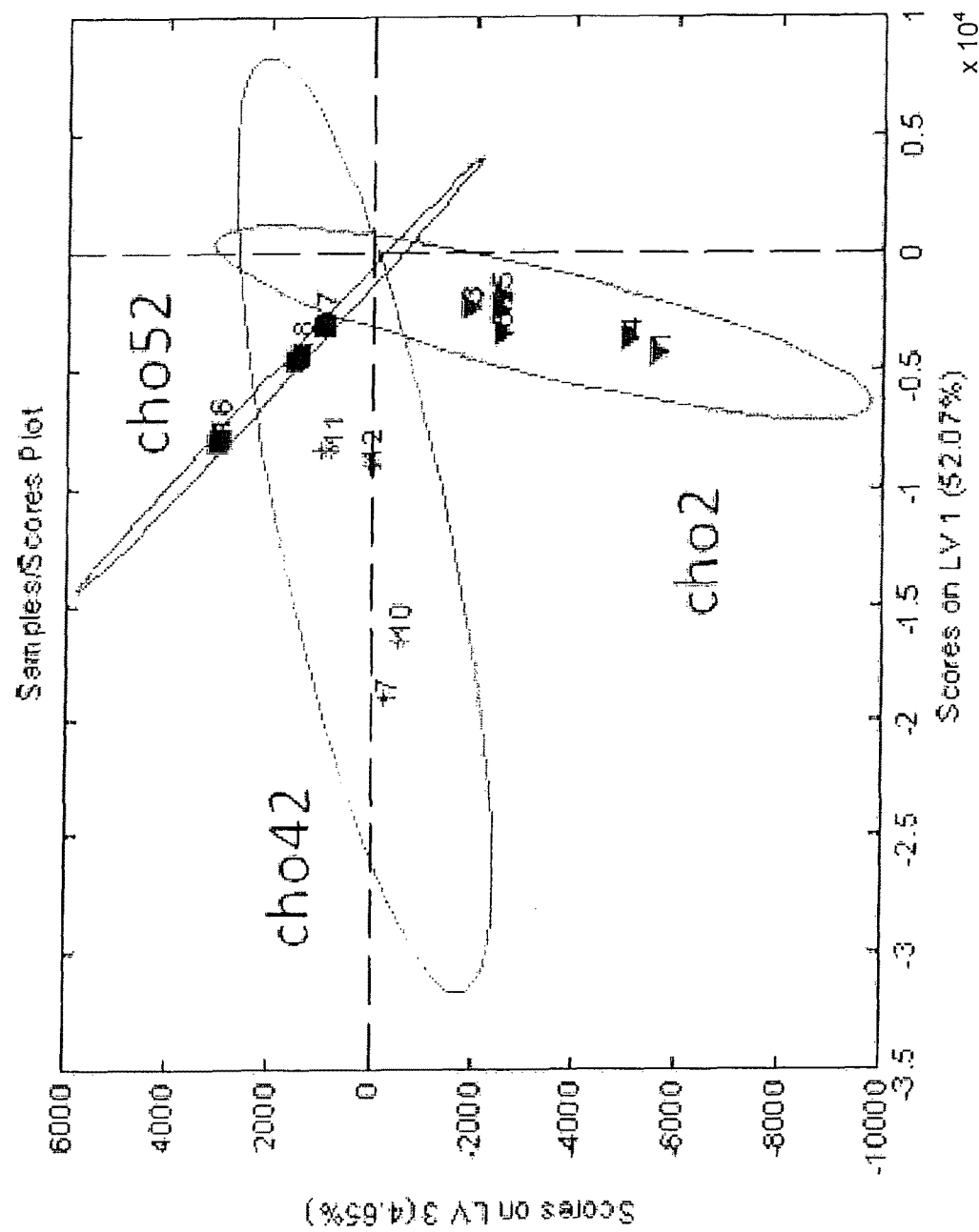

FIGS. 19a and 19b show PLSDA analysis comparing the LC-ESI-MS data from the antibody-producing cell lines CHO 2, 42 and 52.

Figure 20:
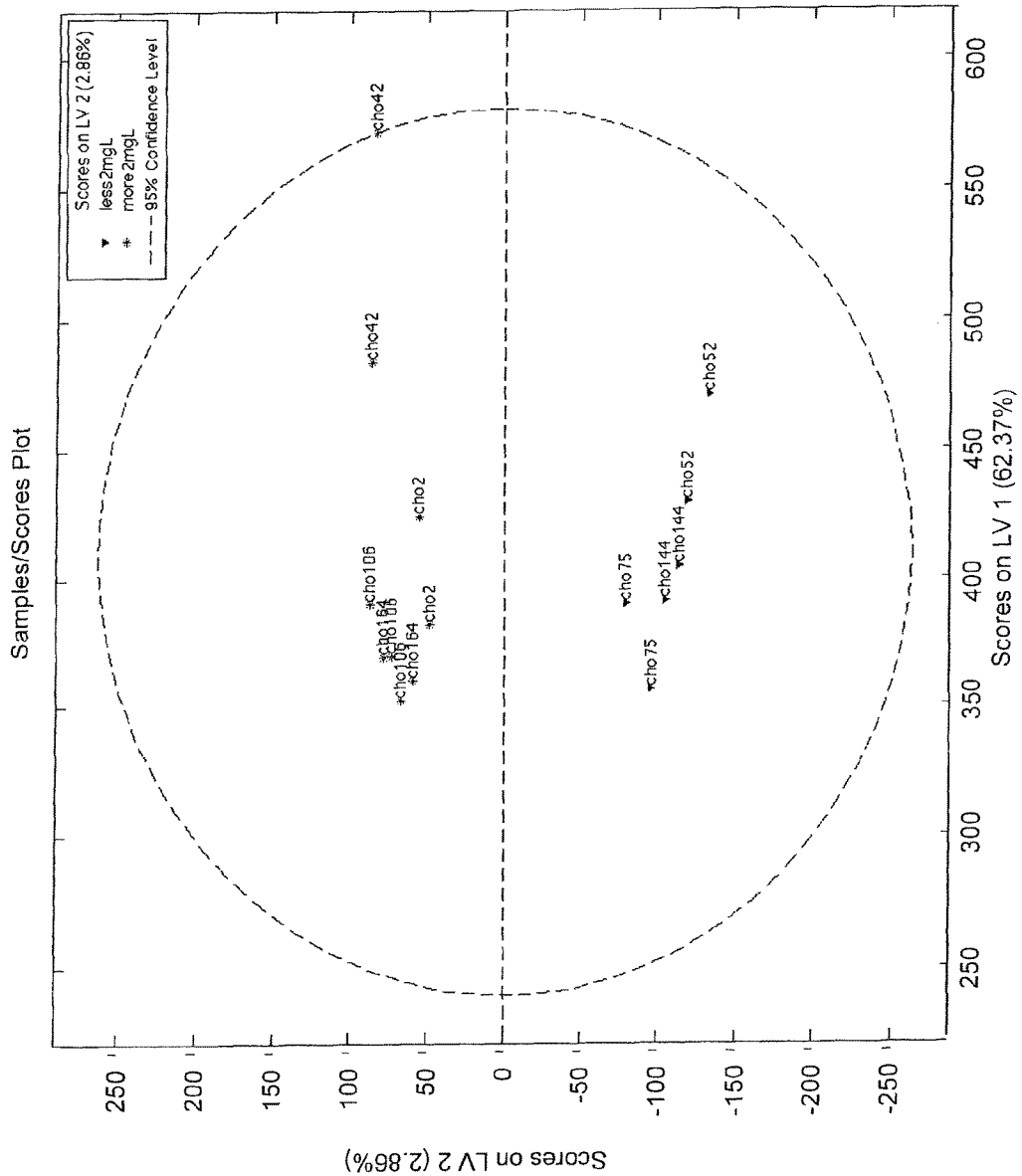

FIG. 20 shows PLSDA analysis comparing the LC-ESI-MS data from seven antibody-producing CHO cell lines (2, 42, 52, 75, 106, 144 and 164) with samples grouped into lower than 2 g/l and higher than 2 g/l.

Figure 21A:
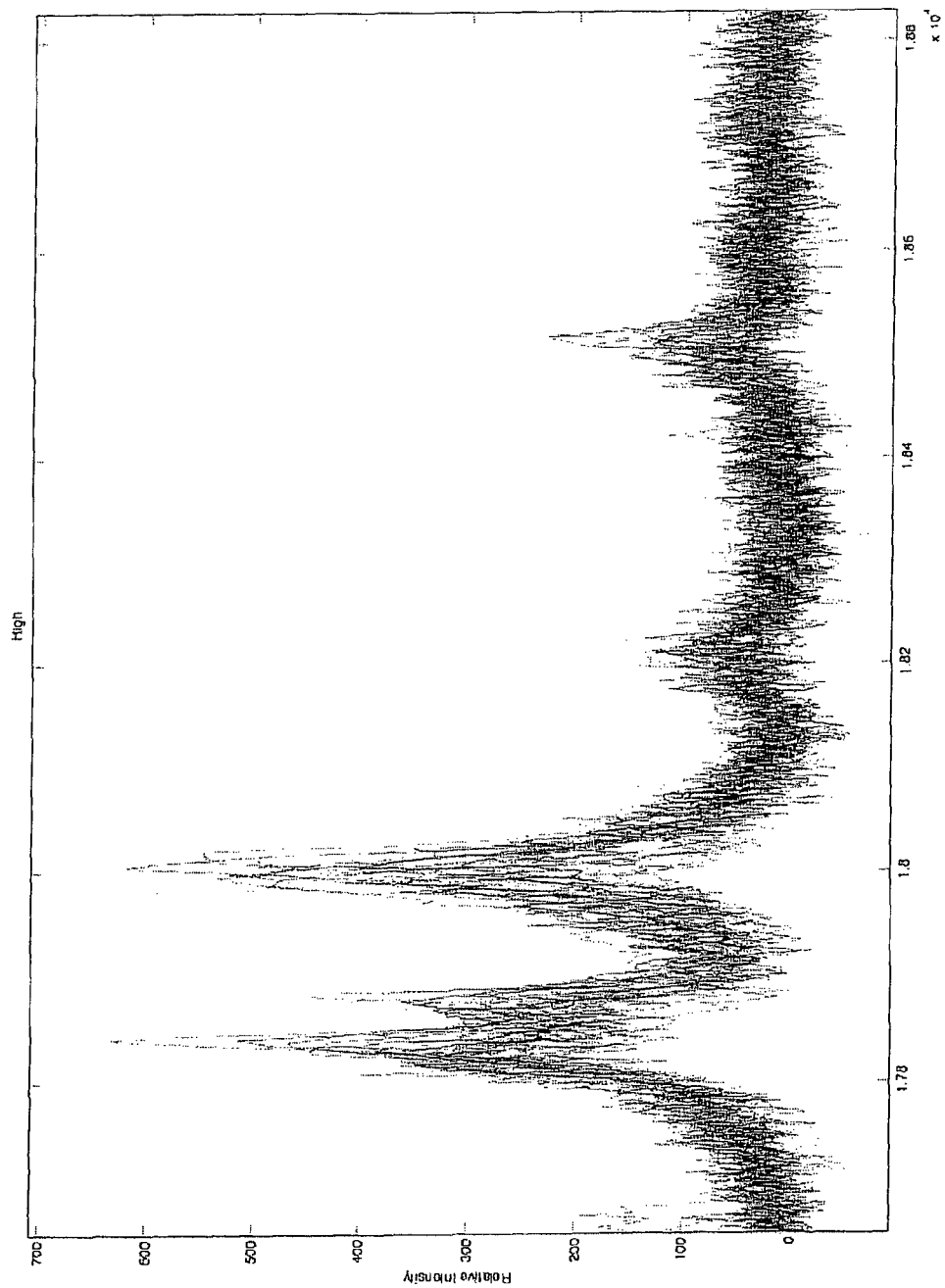
Figure 21B:
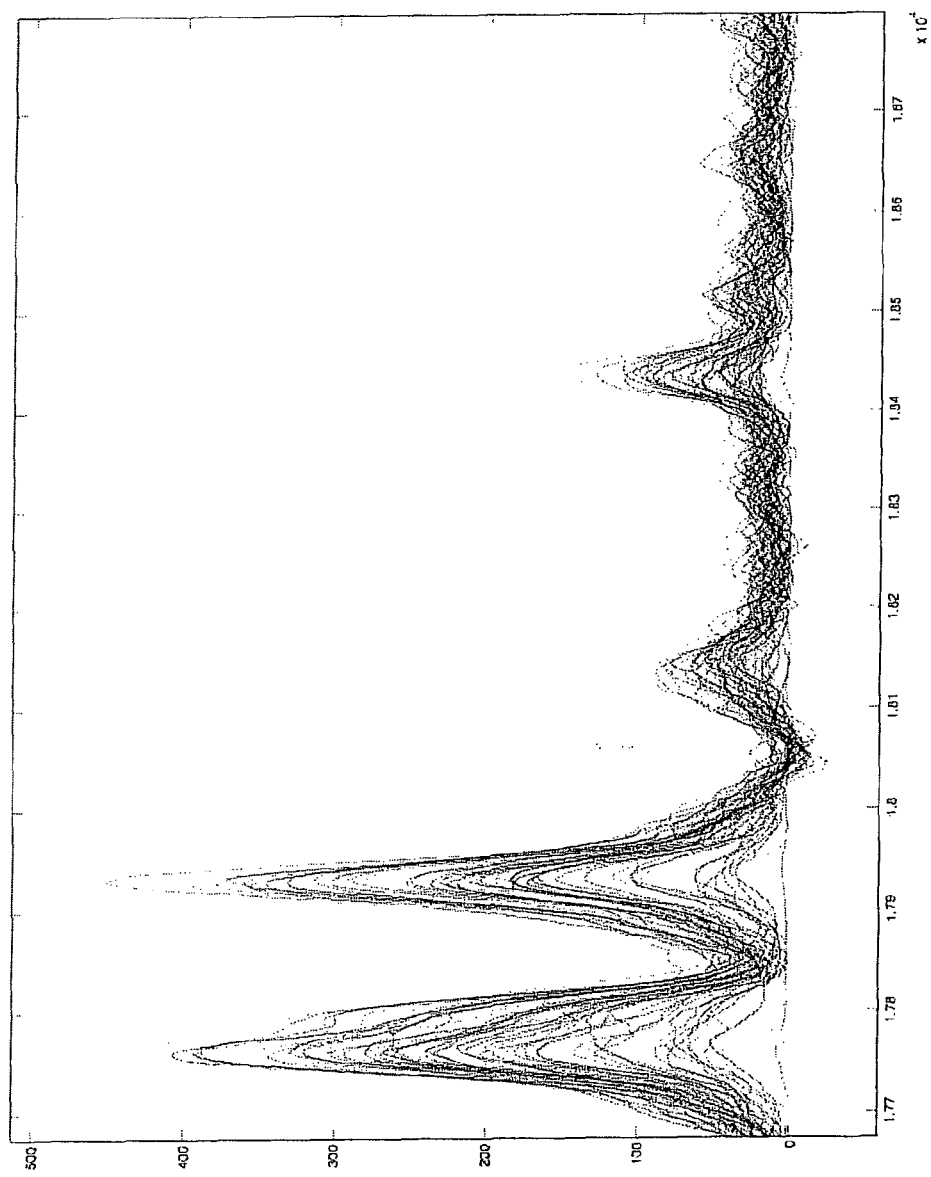

FIGS. 21a and 21b show MS profiles pre-treated with a MS signal processing method comprising baseline correction and normalisation (21a) and comprising resampling, baseline correction, filtering, alignment, visual analysing and normalisation (21b).

Figure 22:
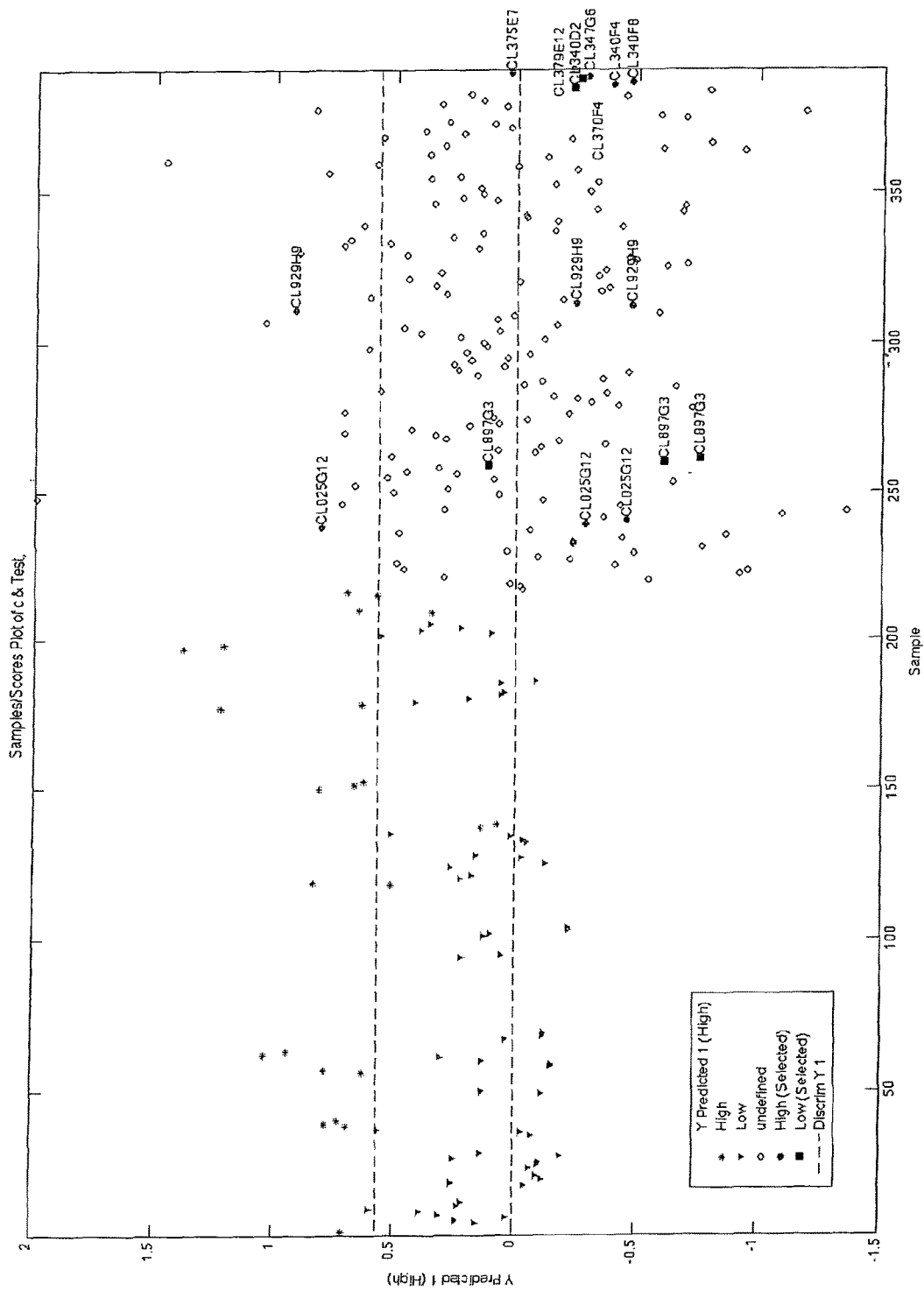

FIG. 22 shows a Y Predicted plot for cell lines Round 1 predictions using the pre-treatment of raw MS data according to the present invention, including resampling, baseline correction, filtering, alignment, visual analysing and normalisation of the raw MS data, and subsequent PLS-DA modelling.

Figure 23:
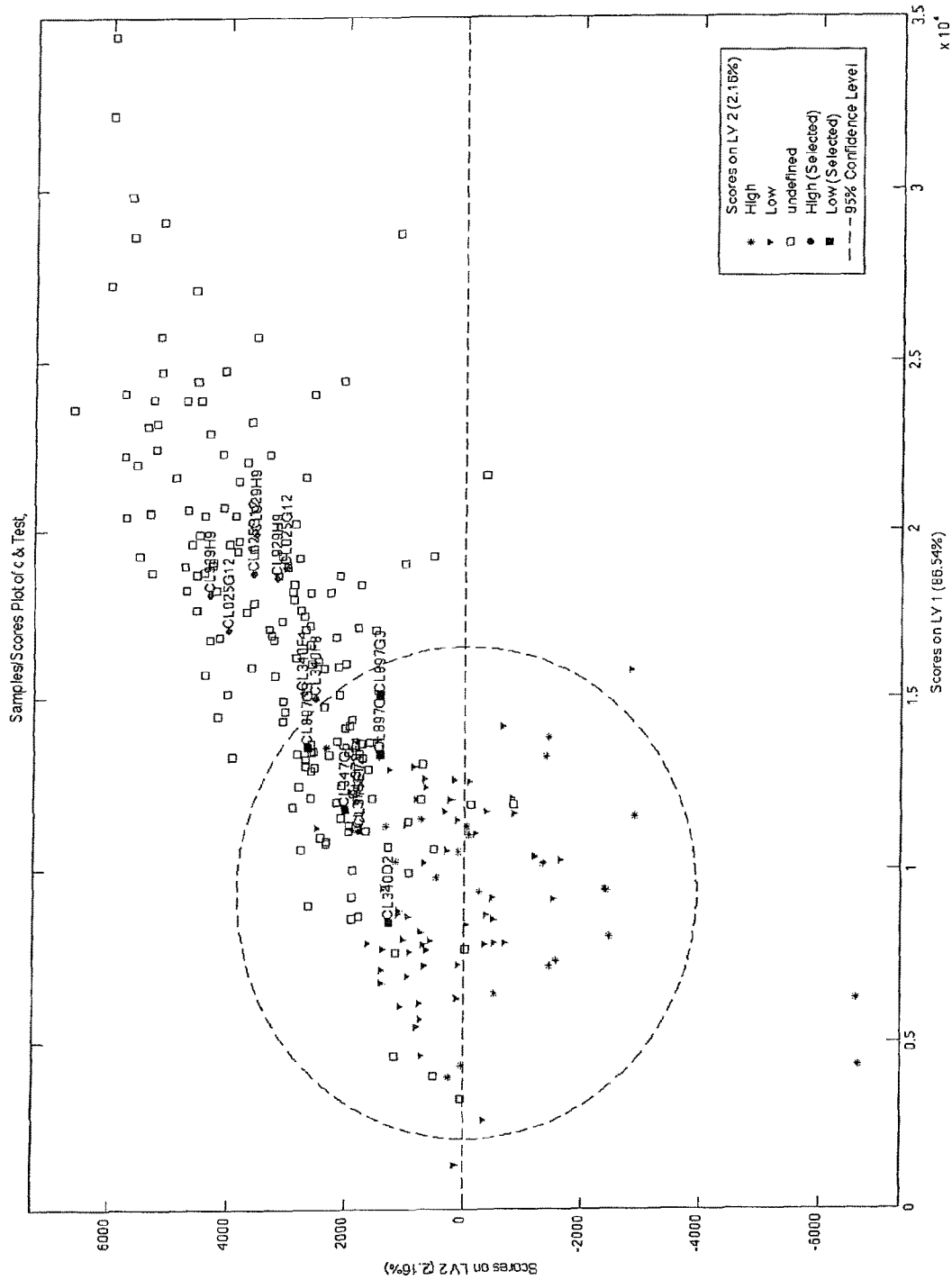

FIG. 23 shows a LV1 vs LV2 for cell lines Round 1 predictions using the pre-treatment according to the present invention.

Figure 24:
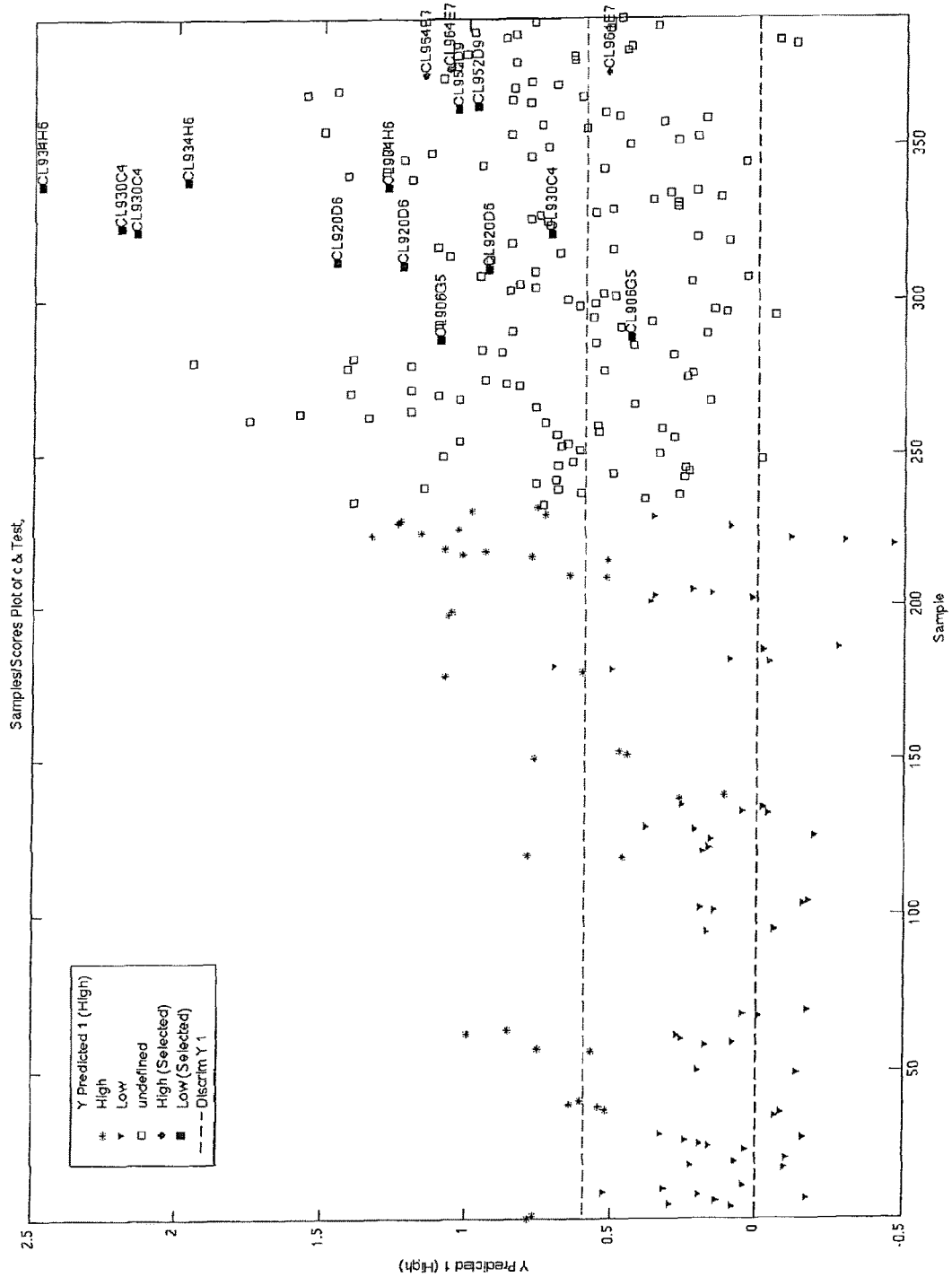

FIG. 24 shows a Y Predicted plot for cell lines Round 2 Predictions using the pre-treatment of raw MS data according to the present invention, including resampling, baseline correction, filtering, alignment, visual analysing and normalisation of the raw MS data, and subsequent PLS-DA modelling.

Figure 25:
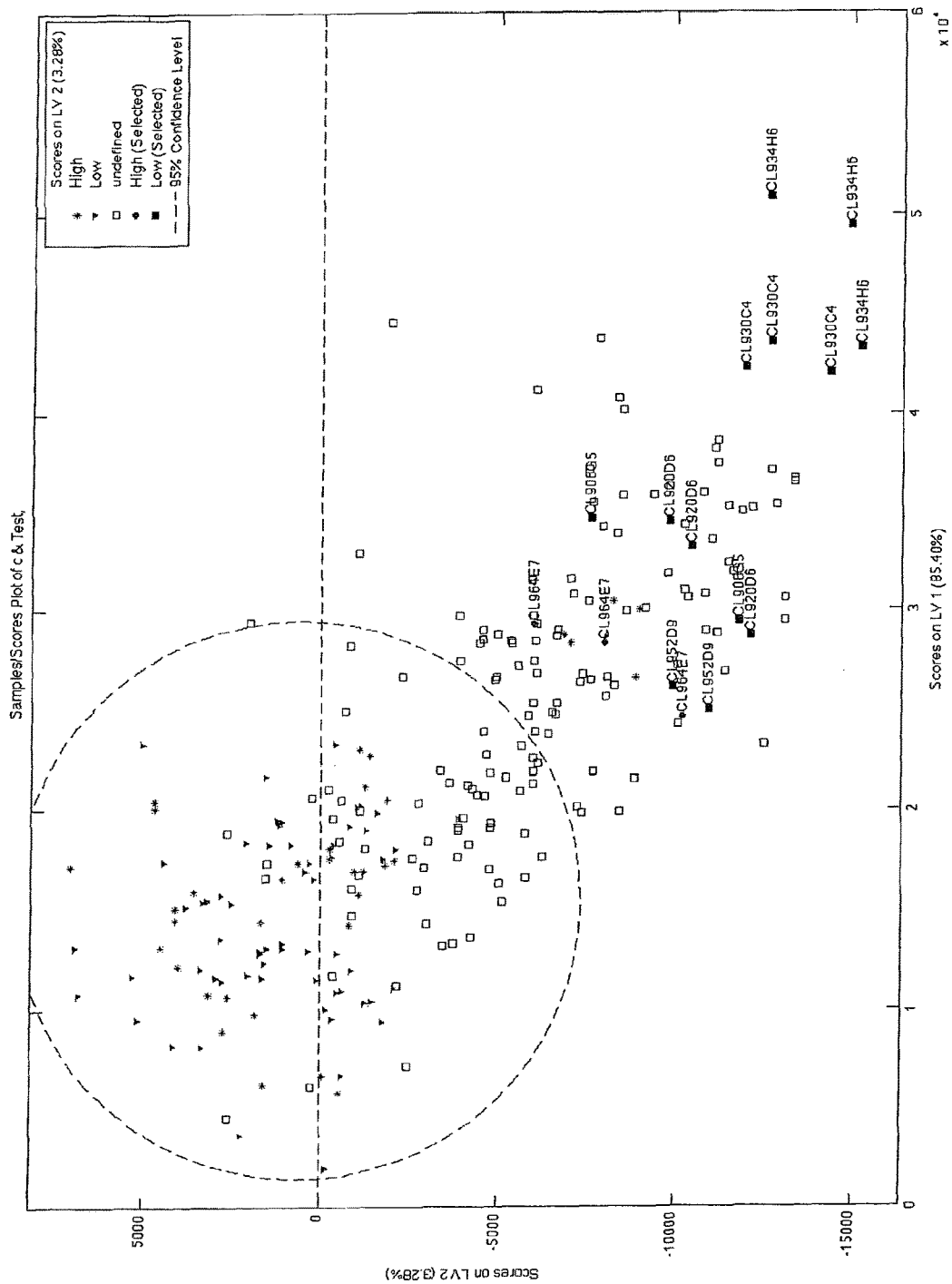

FIG. 25 shows a LV1 vs LV2 for cell lines Round 2 predictions using the pre-treatment according to the present invention.

Figure 26:
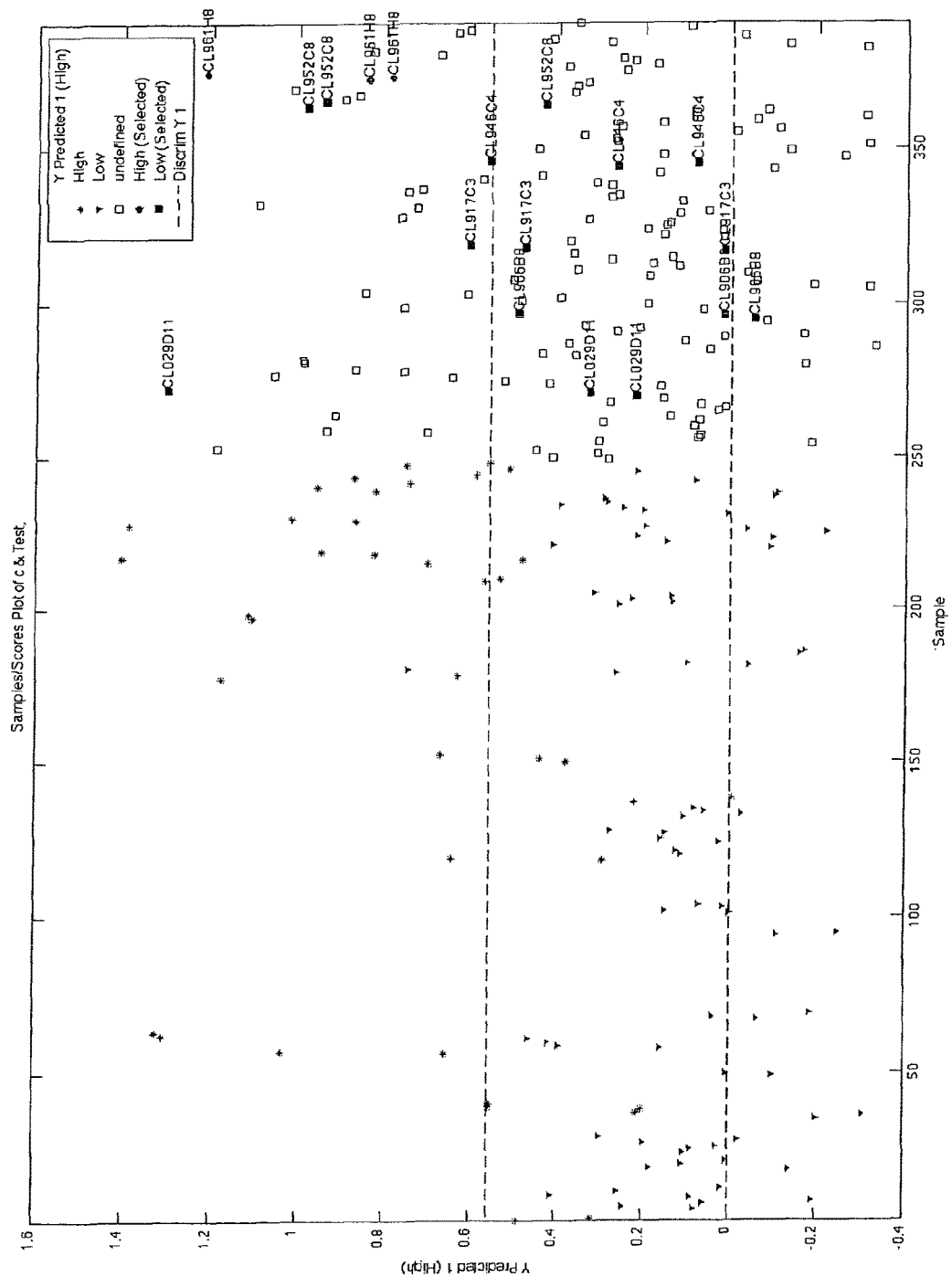

FIG. 26 shows a Y Predicted plot for cell lines Round 3 Predictions using the pre-treatment of raw MS data according to the present invention, including resampling, baseline correction, filtering, alignment, visual analysing and normalisation of the raw MS data, and subsequent PLS-DA modelling.

Figure 27:
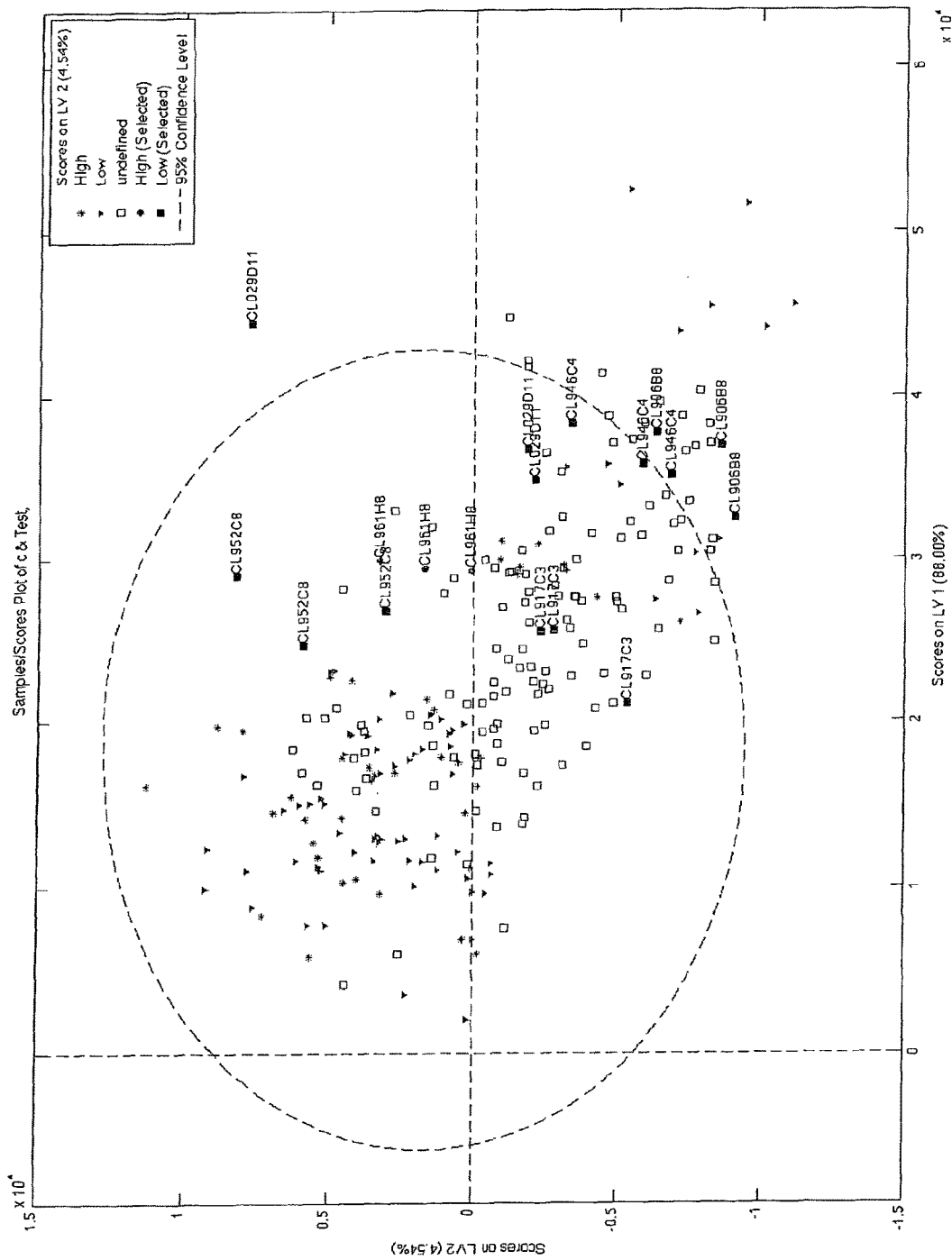

FIG. 27 shows a LV1 vs LV2 for cell lines Round 3 predictions using the pre-treatment according to the present invention.

Figure 28:
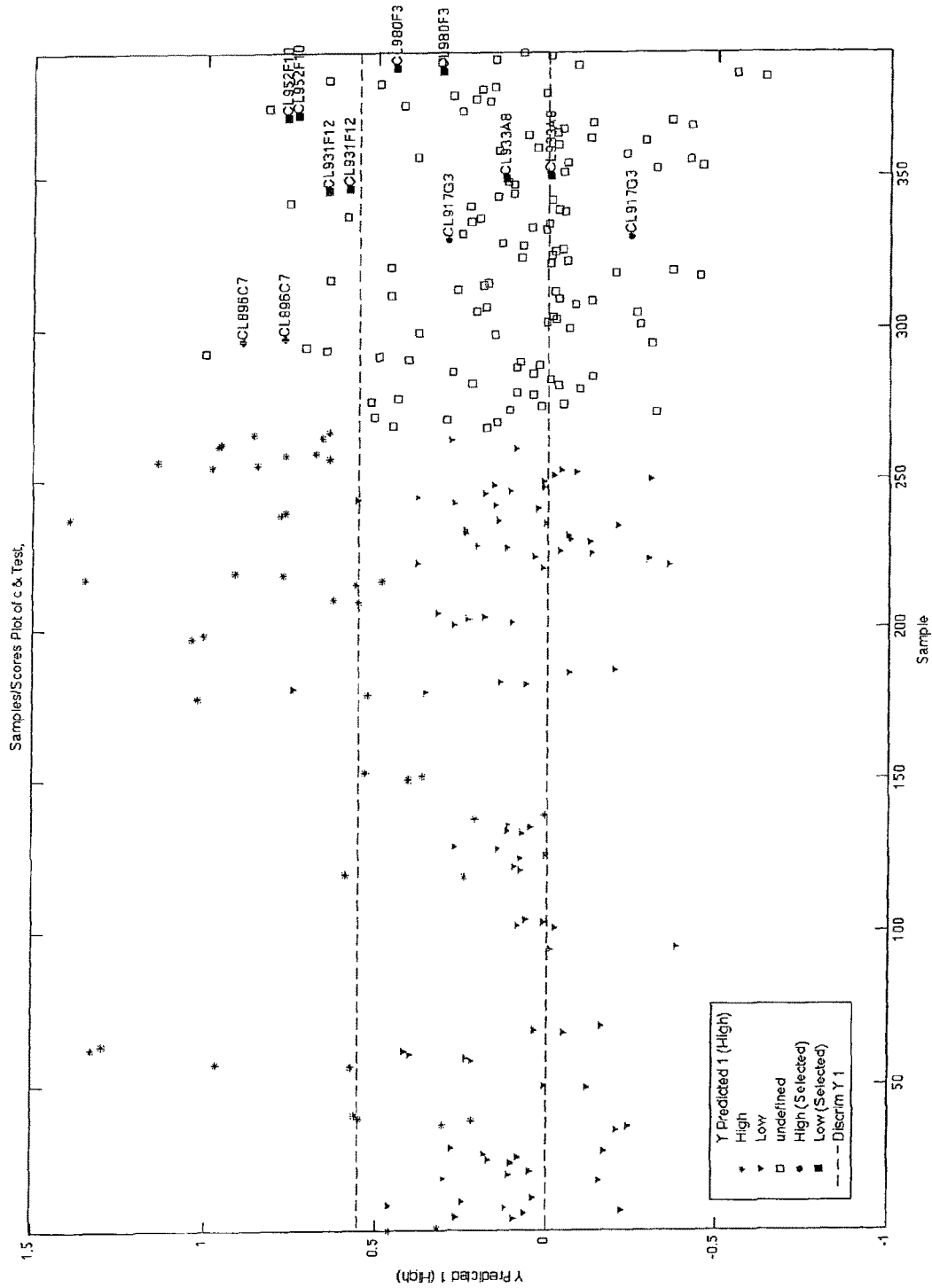

FIG. 28 shows a Y Predicted plot for cell lines Round 4 Predictions using the pre-treatment of raw MS data according to the present invention, including resampling, baseline correction, filtering, alignment, visual analysing and normalisation of the raw MS data, and subsequent PLS-DA modelling.

Figure 29:
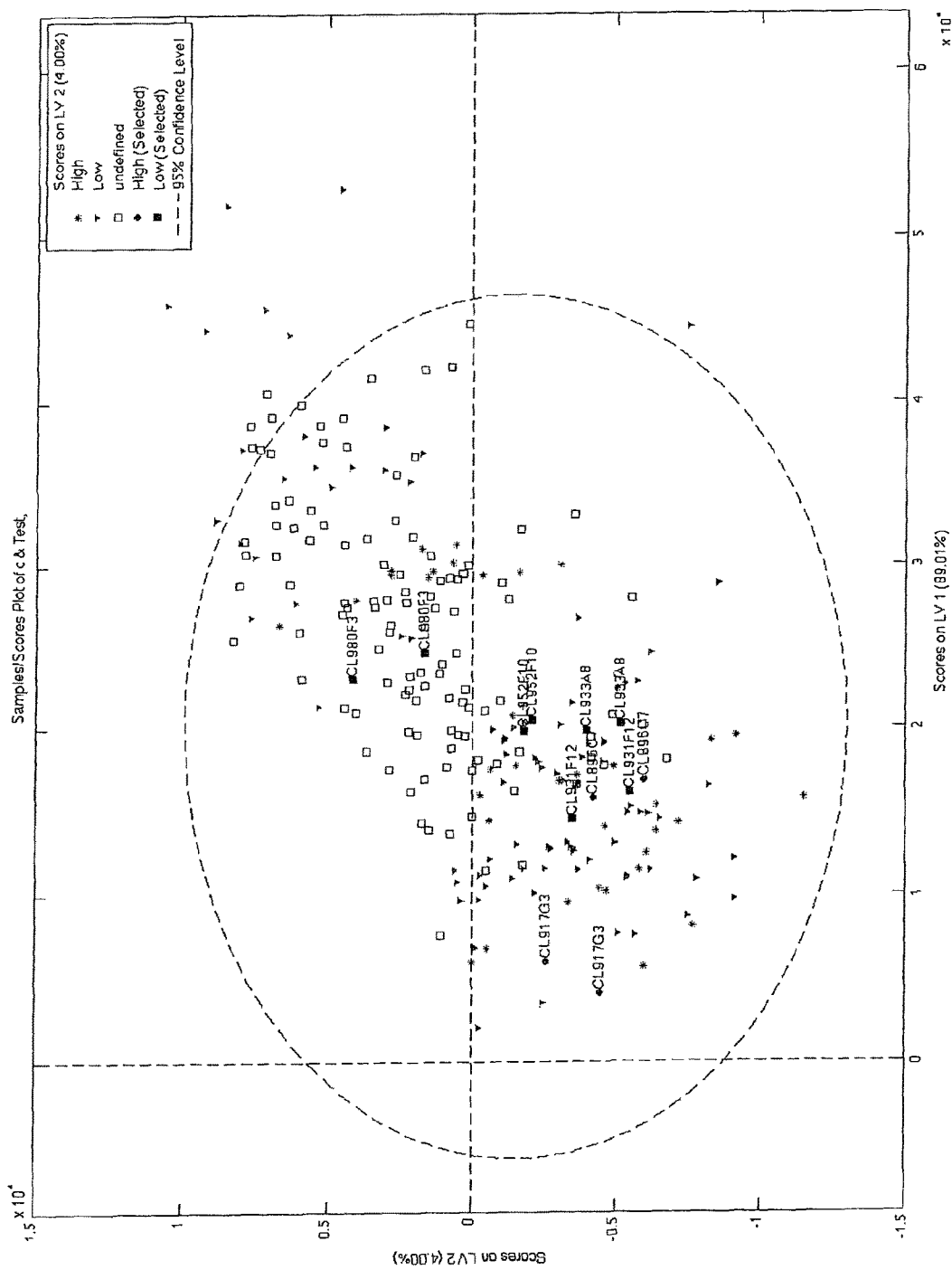

FIG. 29 shows a LV1 vs LV2 for cell lines Round 4 predictions using the pre-treatment according to the present invention.

Figure 30:
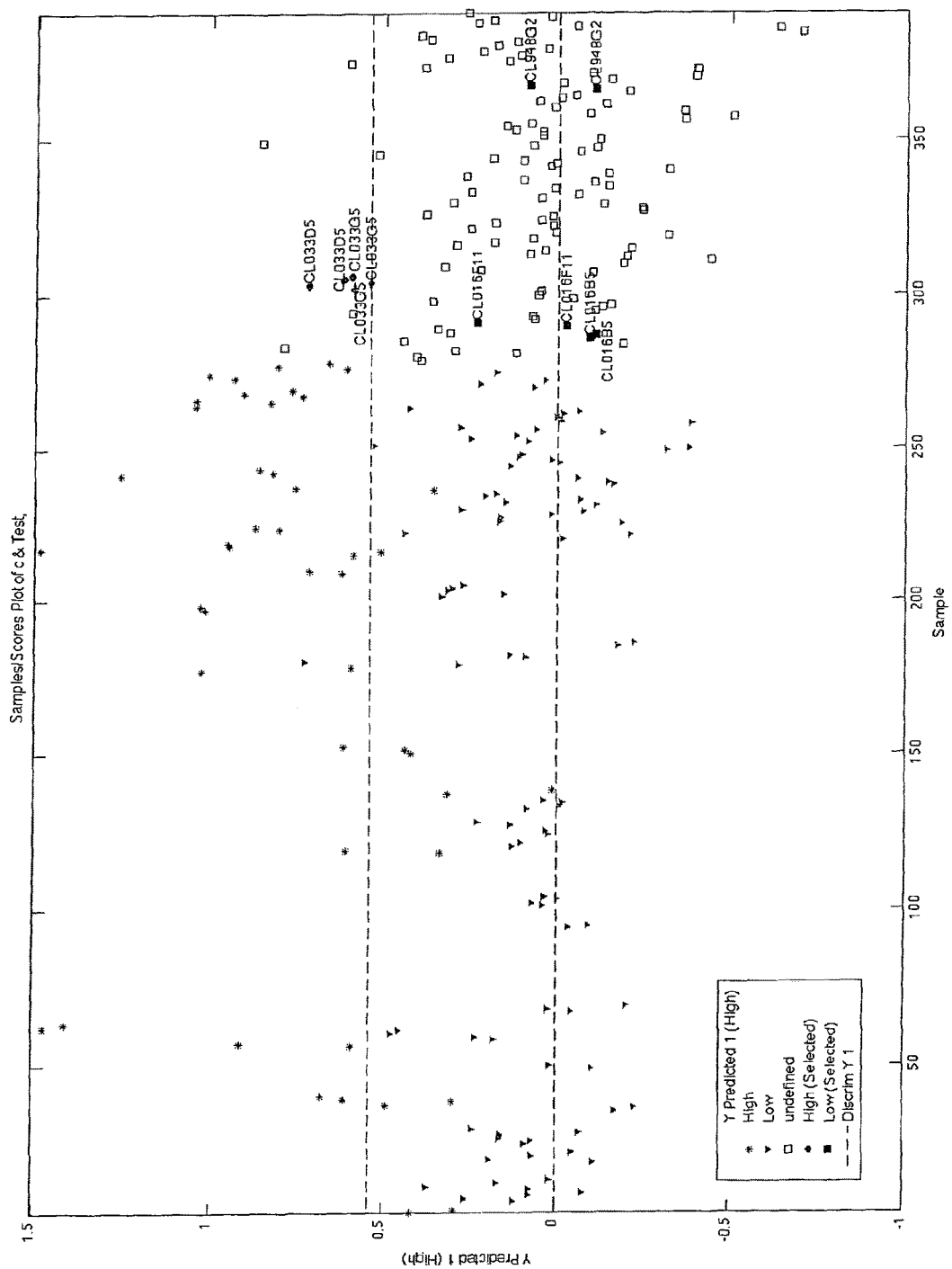

FIG. 30 shows a Y Predicted plot for cell lines Round 5 Predictions using the pre-treatment of raw MS data according to the present invention, including resampling, baseline correction, filtering, alignment, visual analysing and normalisation of the raw MS data, and subsequent PLS-DA modelling.

Figure 31:
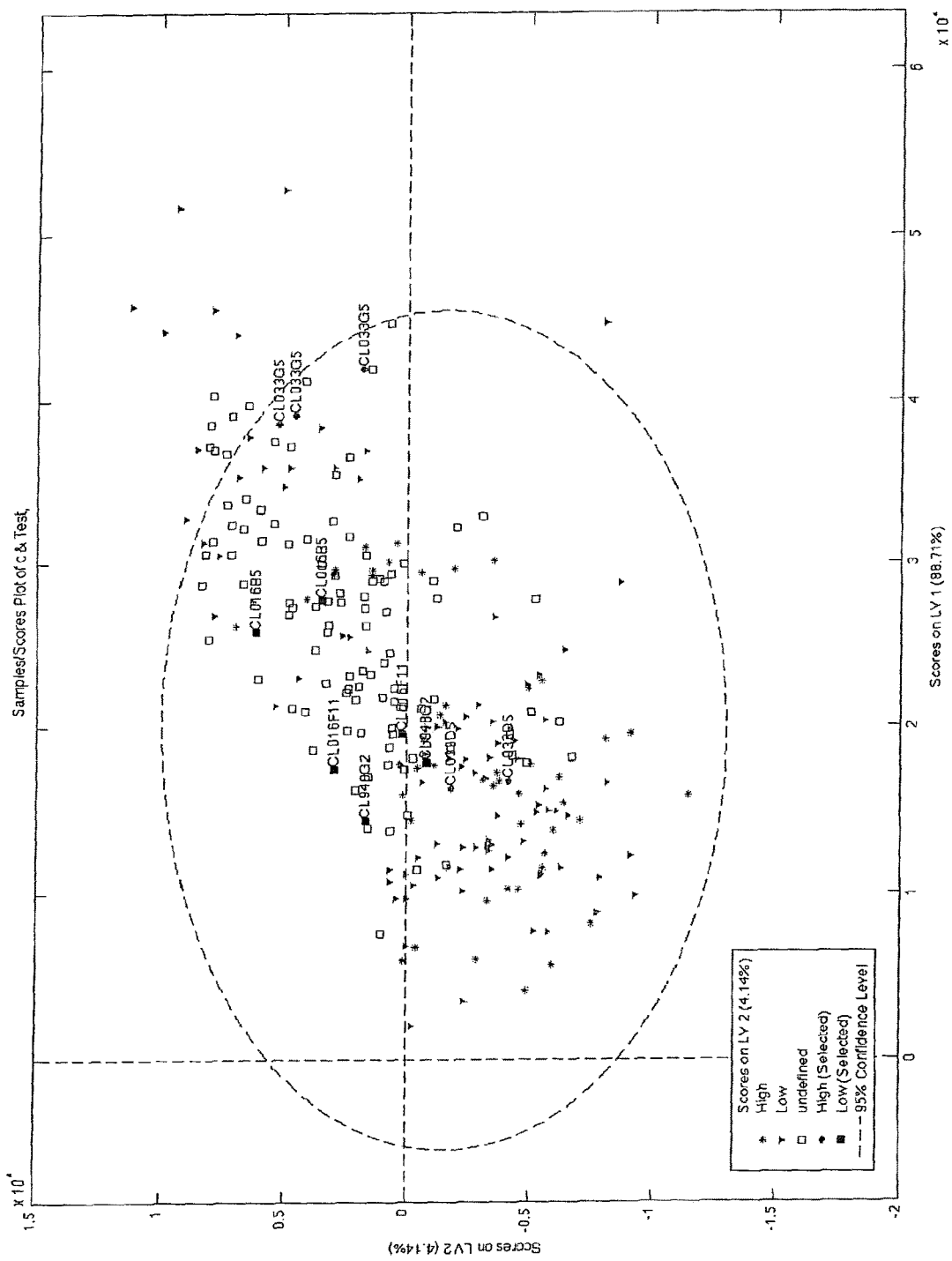

FIG. 31 shows a LV1 vs LV2 for cell lines Round 5 predictions using the pre-treatment according to the present invention.

Figure 32:
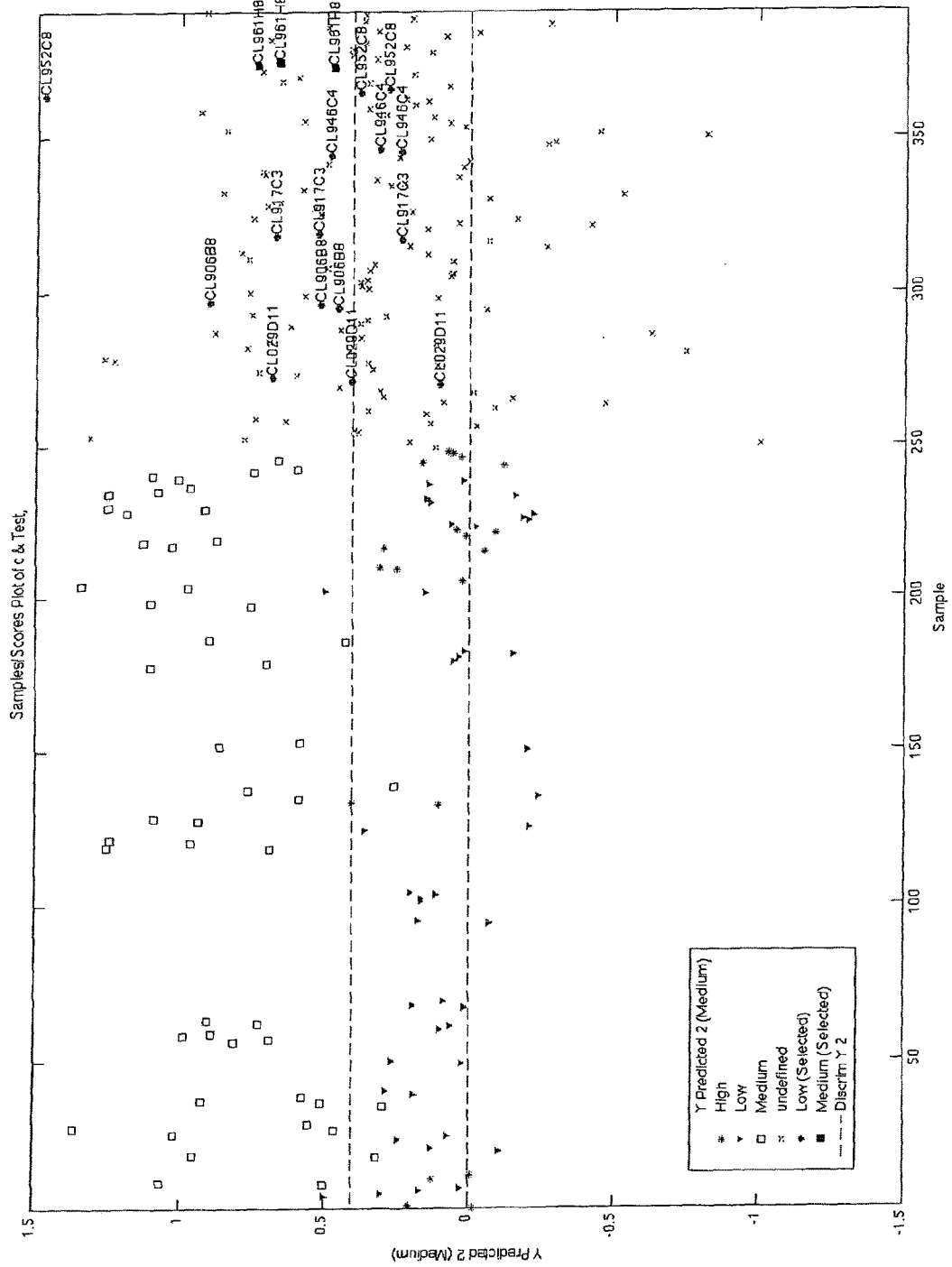

FIG. 32 shows an IVC Y Predicted plot for cell lines Round 3 Predictions using the pre-treatment of raw MS data according to the present invention, including resampling, baseline correction, filtering, alignment, visual analysing and normalisation of the raw MS data, and subsequent PLS-DA modelling.

Figure 33:
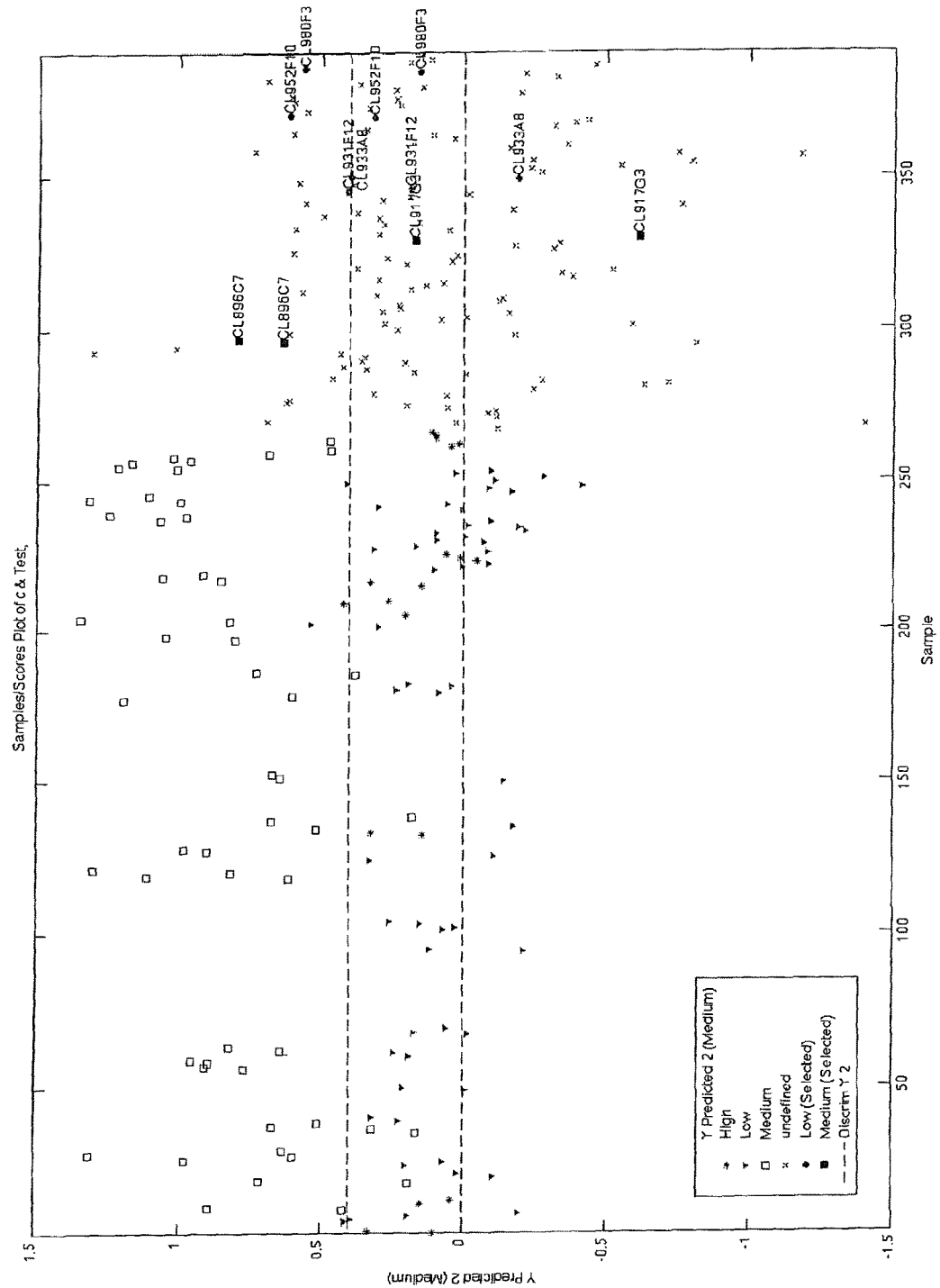
Figure 34:
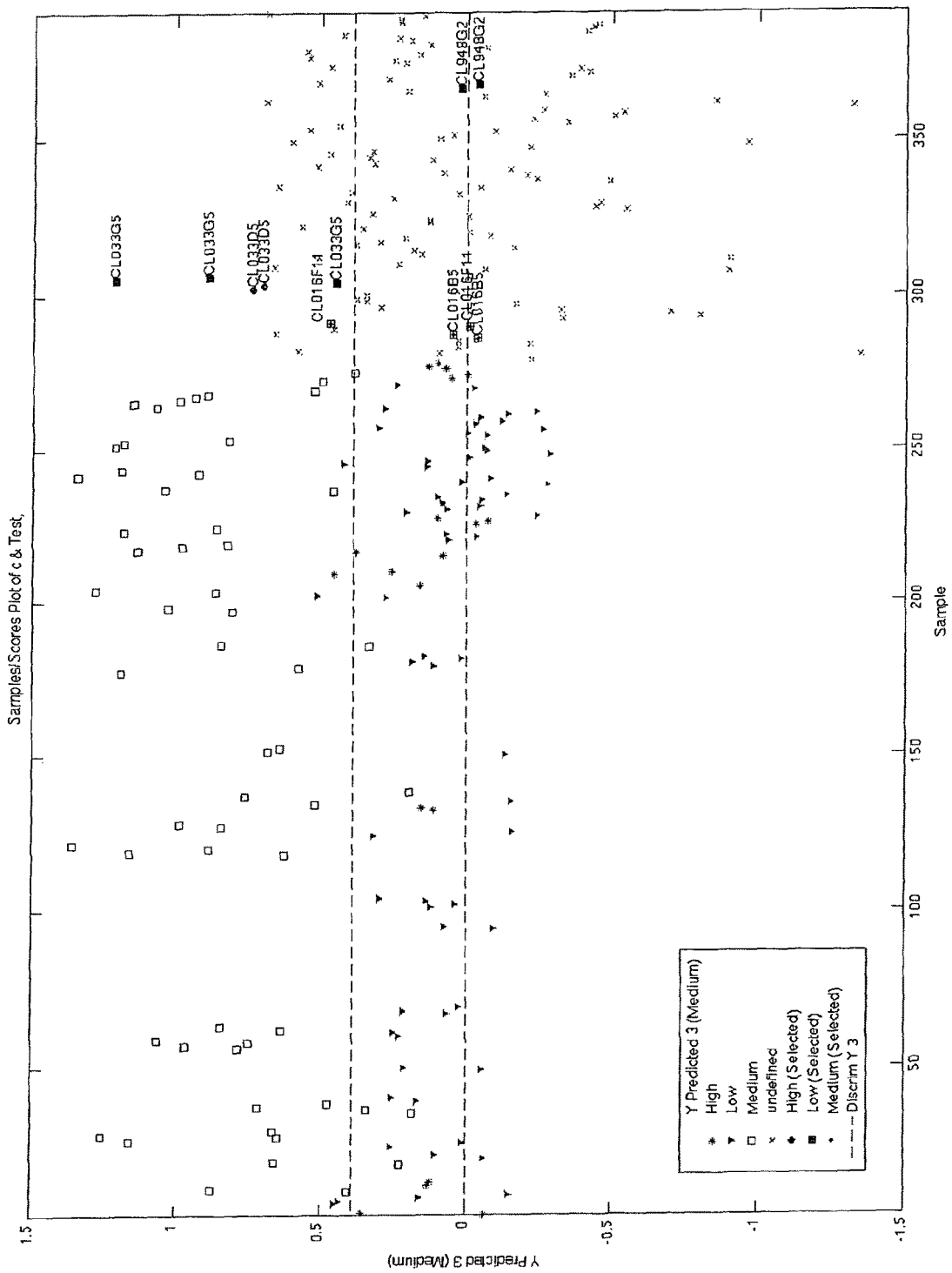

FIG. 33 shows an IVC Y Predicted plot for cell lines Round 4 Predictions using the pre-treatment of raw MS data FIG. 34 shows an IVC Y Predicted plot for cell lines Round 5 Predictions using the pre-treatment of raw MS data according to the present invention, including resampling, baseline correction, filtering, alignment, visual analysing and normalisation of the raw MS data, and subsequent PLS-DA modelling.

Figure 35:
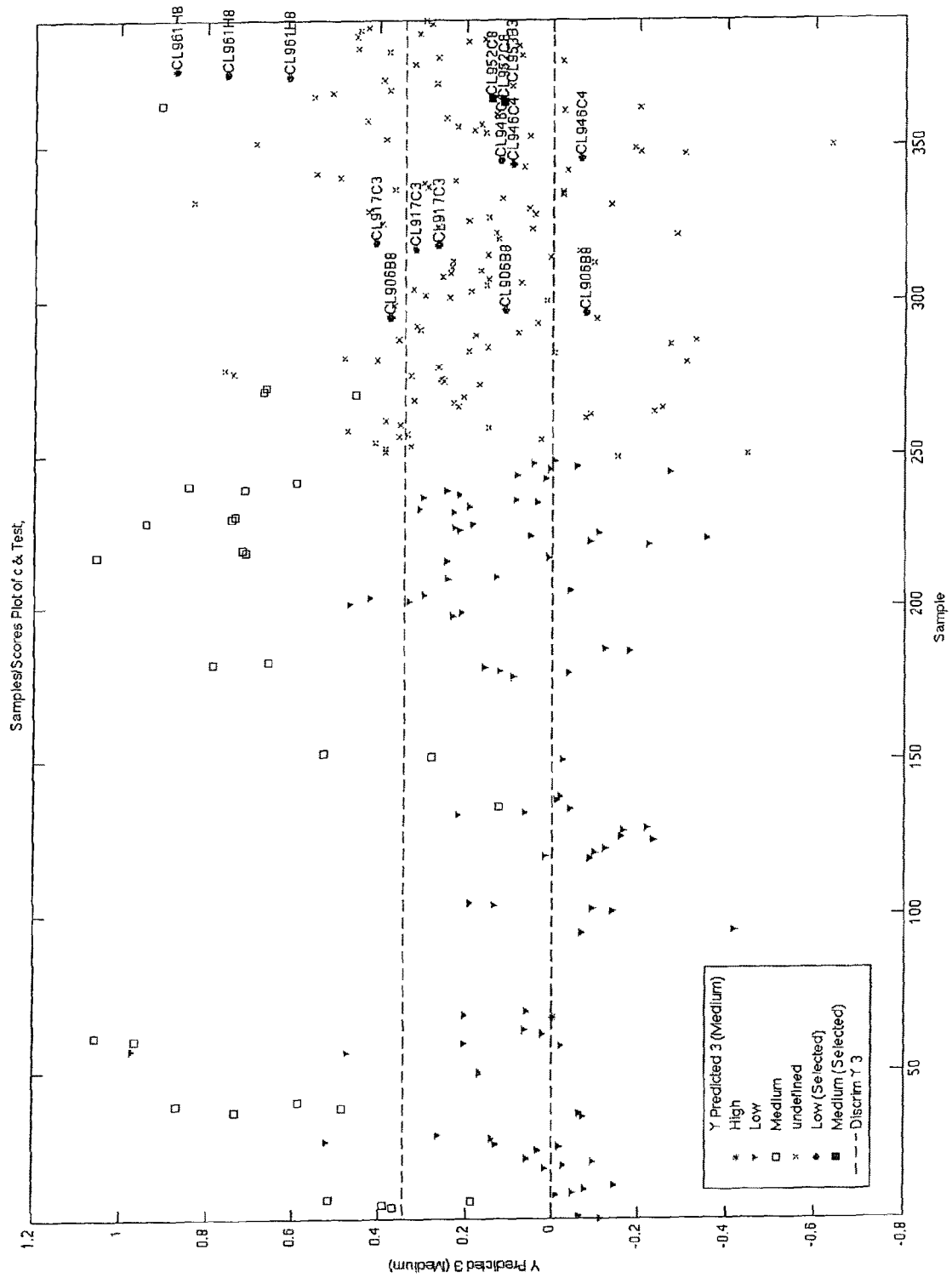

FIG. 35 shows a qP Y Predicted plot for cell lines Round 3 Predictions using the pre-treatment of raw MS data according to the present invention, including resampling, baseline correction, filtering, alignment, visual analysing and normalisation of the raw MS data, and subsequent PLS-DA modelling.

Figure 36:
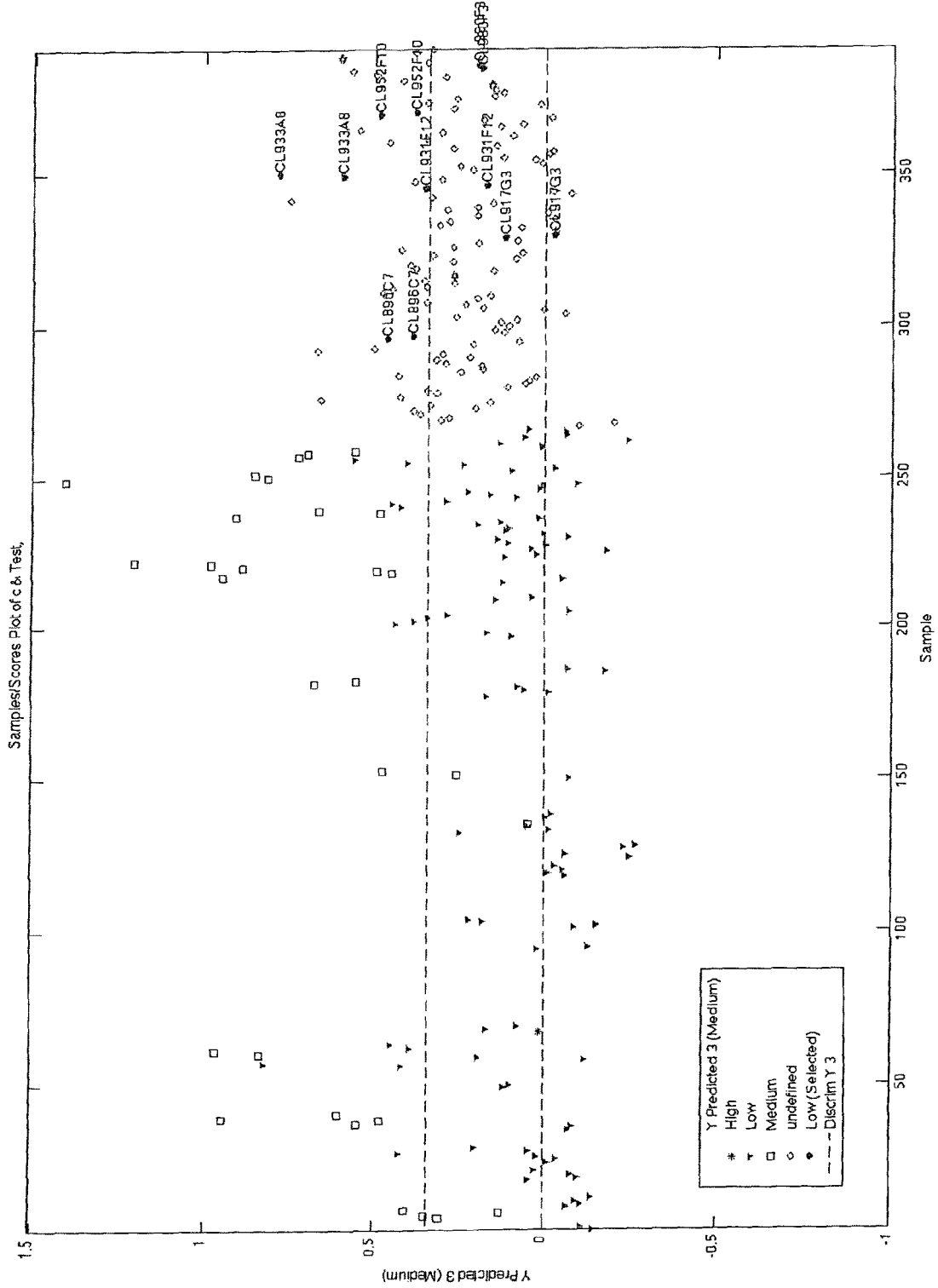

FIG. 36 shows a qP Y Predicted plot for cell lines Round 4 Predictions using the pre-treatment of raw MS data according to the present invention, including resampling, baseline correction, filtering, alignment, visual analysing and normalisation of the raw MS data, and subsequent PLS-DA modelling.

Figure 37:
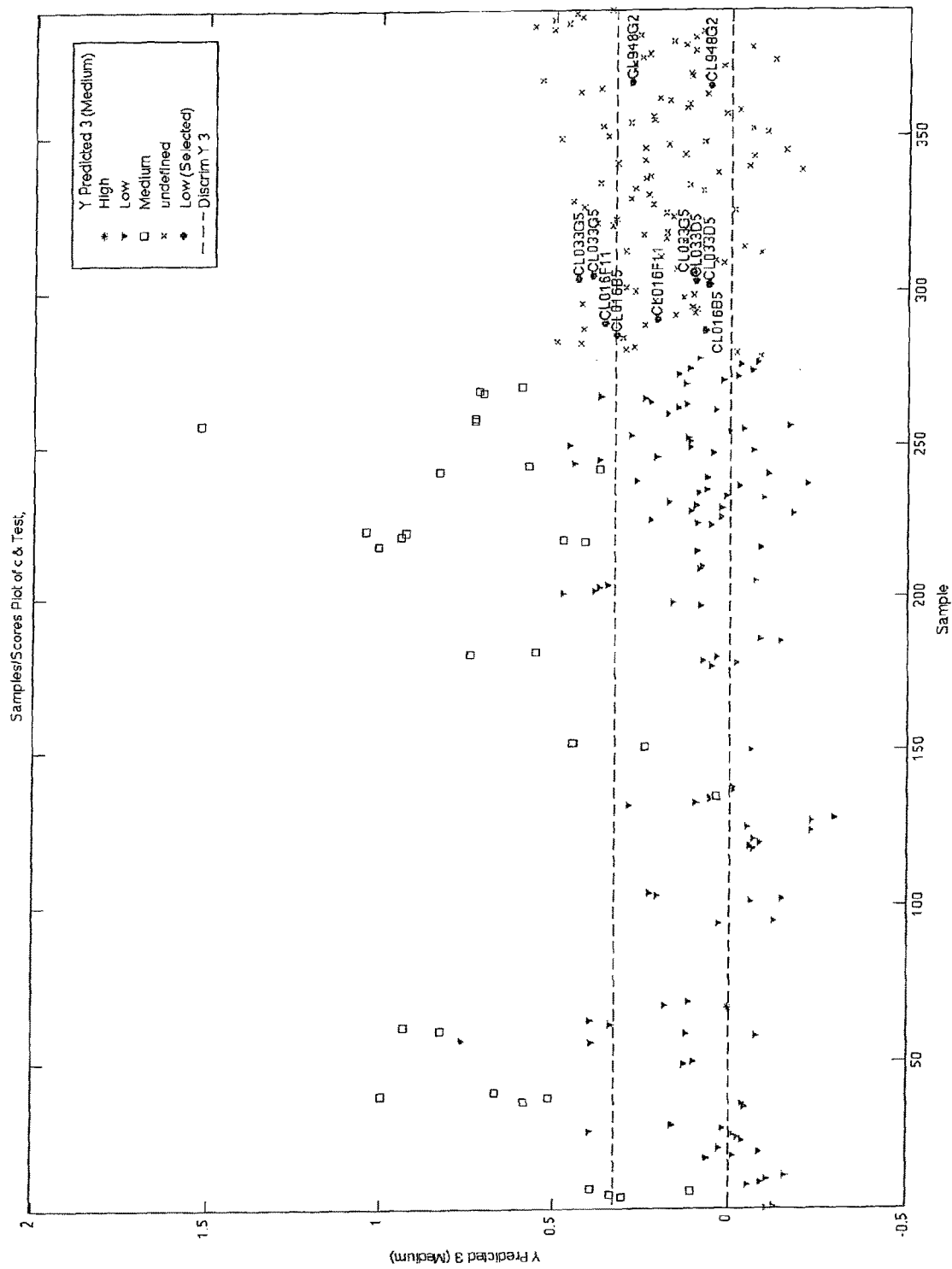

FIG. 37 shows a qP Y Predicted plot for cell lines Round 5 Predictions using the pre-treatment of raw MS data according to the present invention, including resampling, baseline correction, filtering, alignment, visual analysing and normalisation of the raw MS data, and subsequent PLS-DA modelling.

EXAMPLE 1

Cell Line Generation (According to the State of the Art)

A GS expression vector (Lonza) containing gene-optimised heavy and light chain genes for the expression of a model mouse-human chimeric IgG4 or IgG1 antibody (Kalwy et al., Mol. Biotechnol. 2006, 34, 151-156) was used to generate recombinant, antibody expressing GS-CHO cell lines. The vector was introduced into the host cell line, CHOK1SV (a derivative of CHO-K1; Lonza), using standard electroporation methods and the transfection mixture was distributed across eighty 96-well plates. Plates were incubated at 37° C. in a humidified, 10% $CO_2$ in air atmosphere. The following day, fresh medium was added to the cell suspension in the plates. The MSX (methionine sulphoxamine) concentration in the medium was such that the final MSX concentration in each well was 50 µM. Plates were first screened for glutamine-independent transfectants at approximately 3 weeks post transfection. Transfectant colonies isolated (each identified as originating from a well with a single colony) were progressed through all the assessment stages of a typical cell line construction strategy.

Cell concentration of the cultures was determined using a Vi-CELL™ automated cell viability analyser (Beckman Coulter). Cultures were established in 125 mL shake-flasks with a target cell concentration of $2.0 \times 10^5$ viable cells/mL and a final volume of typically 30 mL. Cell lines were serially subcultured on a 4 day regime. Once acceptable cell concentrations at subculture were reached and any large fluctuations in viable cell concentration between subcultures had ceased, the assessment stages performed in suspension culture commenced. The 'fed-batch' assessment was performed after the cell lines were ranked following the first suspension evaluation ('batch'). For the fed-batch assessment, the cell concentration of the cultures was determined on days 7 and 14 using a Vi-CELL™ automated cell viability analyser. A bolus addition of feed A was made on day 3 and bolus additions of feed B were made on days 8 and 11. Samples of culture supernatant were taken on different days for antibody concentration determination. Cell viability analysis could alternatively be done with MACSQuant® Analyzer.

EXAMPLE 2

Preparation of the Sample Cells for the MALDI-TOF Analysis

Unless otherwise specified, all experiments have been conducted under the same culture conditions as outlined under the example 1 (first paragraph). Before the sample probes (that means the samples) were subjected to the MS analysis the cells were counted and the required volume of culture to provide the appropriate number of cells calculated. Cells were removed from the incubator (96 well plate) immediately prior to processing. The required volume of each sample was transferred to an Eppendorf tube, centrifuged for 5 minutes at 960 rcf (3000 rpm) in an Eppendorf microfuge (model 5417c, rotor F-45-30-11) and the supernatant removed. The cells were then washed with 1 ml of PBS (phosphate buffered saline) by gently pipetting up and down then centrifuged as above. Where indicated, cells were subsequently washed with 1 ml of 0.35 M sucrose and the supernatant removed after centrifuging as described above. At that point cell pellets could be stored (−80° C.) for further handling in the future or immediately processed for MS analysis. In case of storage frozen cell pellets need to equilibrate to room temperature before used after thawing.

A 20 mg/ml solution of sinapinic acid was prepared in matrix buffer (40% acetonitrile, 60% 0.1% TFA) which results in a saturated solution. The sinapinic acid solution was then placed in a sonicating water bath for 15 minutes before centrifugation at 17900 rcf (13000 rpm) for 5 minutes in an Eppendorf microfuge (model 5417c, rotor F45-30-11).

Matrix solution (50 µl) was then added to each sample and the cells re-suspended by manually pipetting the solution up and down. After resuspension the cells were placed at 4° C. for up to several hours. On removal from 4° C., the cells were re-suspended by gently tapping the tube and then 1 µl of each sample was spotted onto a 384 MTP ground steel MALDI TOF plate (Bruker). Samples were allowed to air dry before the plate was put into the MALDI TOF machine (Bruker Ultraflex) and the samples analysed.

EXAMPLE 3

Preparation of Sample Cells for LC-ESI-MS Analysis Using Dunn Lysis Buffer

Sample collection: A range of CHO cell lines were grown in 250 ml suspension cell culture flasks. Cells were counted using a Vi-CELL™ and the cell number required ($1 \times 10^6$ to $0.015625 \times 10^6$) were pipetted into 1.5 ml Eppendorf tubes and centrifuged at 960 rcf in an Eppendorf microfuge (model 5417c, rotor F-45-30-11) for 5 mins and the supernatant removed. The pellets were stored at −80° C. until used.

Cell lysis: The pellets were thawed and resuspended in 400 µl of Dunn Lysis buffer (Ultra pure urea 9.5 M, CHAPS 2%, DTT 1%) vortexed thoroughly and incubated at room temperature (RT) for 1 h with a brief vortex at 30 min after the start of incubation. Samples were then centrifuged at 985.6 g, preferably 1700 rcf (relative centrifugal force), for 1 min to remove cell debris and the supernatant was pipetted into 2 ml Eppendorfs. 50 µl of sample was then used for acetone precipitation.

Acetone precipitation: A 4:1 dilution of 100% ice cold acetone to sample was incubated for 1 h at −20° C. The diluted sample was then centrifuged at 8870.4 g, preferably 17900 rcf (relative centrifugal force), for 10 min, the supernatant removed and the pellet left to dry at air briefly (not more than 5 min).

The 2D clean-up kit from GE healthcare (product code 80-6484-51) was used to clean up the samples before the solution tryptic digest. Procedure A from the manual supplied with the kit was followed.

Tryptic digest in solution: The pellet was re-suspended in 50 µl of 8 M urea, 0.4 M ammonium bicarbonate ($NH_4HCO_3$) by pipetting the sample up and down to initially dislodge the pellet followed by brief vortexing. The sample was reduced chemically by adding 2.5 µl of 100 mM dithiothreitol (DTT) in 50 mM $NH_4HCO_3$ for 1 h in a 37° C. incubator. The sample was then alkylated by adding 5 µl of 100 mM iodoacetamide in 50 mM $NH_4HCO_3$ for 15 min at RT in the dark. The urea concentration was diluted to <2 M by adding 192.5 µl of HPLC grade water followed by the addition of 10 µl of 0.25 µg/ul modified trypsin (Promega). Tryptic digestion was then left to proceed overnight in a 37° C. incubator. The sample was then dried down using a Savant speed vac (SC110A) on a low setting and resuspended in 20 µl of 0.1% formic acid, centrifuged for 8870.4 g for 1 min, the supernatant removed and any pellet resuspended and centrifuged again at 8870.4 g, preferably 17900 rcf (relative centrifugal force), for 1 min then pipetted into screw cap vials with inserts and frozen at −80° C. until analysed by LC-ESI-MS.

EXAMPLE 4

Analysis with LC-ESI-MS

A HPLC method used for the analysis with LC-ESI-MS (ESI-MS (Bruker or Waters) coupled with HPLC (Donex or Agilent)) is shown in Table 1 that resulted in appropriate MS spectra.

The files produced by the LC-ESI-MS were then converted from the proprietary file format (Bruker or Waters) to a universal standard (mzXML) (i.e. using CompassExport) and the resulting files and data subjected to a binning procedure. The binning approach, which is standard for the analysis of this type of MS data, allows the comparison of multiple ESI-MS datasets from different (or the same) samples by aligning them and involves dividing the retention time (elution time from LC system) and m/z range (mass to charge ratio of ions as detected in ESI-MS) into equally spaced intervals, for example, using a retention time bin of 60 seconds and a mass to charge bin of 1 m/z unit per bin.

TABLE 1

Example HPLC gradient run. A 35 min gradient with a flow rate of 0.3 µl/min throughout the run using a multistep gradient as displayed below with buffer A comprising 0.1% formic acid and buffer B comprising 80% acetonitrile (ACN) and 0.1% formic acid.

| Time | % of buffer B | Flow rate (µl/min) |
|---|---|---|
| 0 | 4 | 0.3 |
| 0 | 4 | 0.3 |
| 10 | 55 | 0.3 |

TABLE 1-continued

Example HPLC gradient run. A 35 min gradient with a flow rate of 0.3 µl/min throughout the run using a multistep gradient as displayed below with buffer A comprising 0.1% formic acid and buffer B comprising 80% acetonitrile (ACN) and 0.1% formic acid.

| Time | % of buffer B | Flow rate (µl/min) |
|---|---|---|
| 11 | 90 | 0.3 |
| 16 | 90 | 0.3 |
| 17 | 4 | 0.3 |
| 35 | 4 | 0.3 |

EXAMPLE 5

Data Analysis Protocol Method 2

5.1 Data Processing and Software Development

In the present example for MS based cell line screening and generation, a software tool—run via a Windows interface—which allows the fast and across scale prediction of cell line productivity is used. It is compiled in MATLAB (release 2008b, reference) using the MATLAB Bioinformatics and Statistics toolboxes as well as the PLS_Toolbox (www.eigenvector.com).

The software application starts with the availability of MS profiles from sample and standard cell lines having been grown under different culture conditions and scales. The signal processing tools have been applied to the MS profiles to extract unique MS data patterns indicative of different levels of product producing cell lines.

5.2 Re-Sampling MS Profiles

Figure 1A:
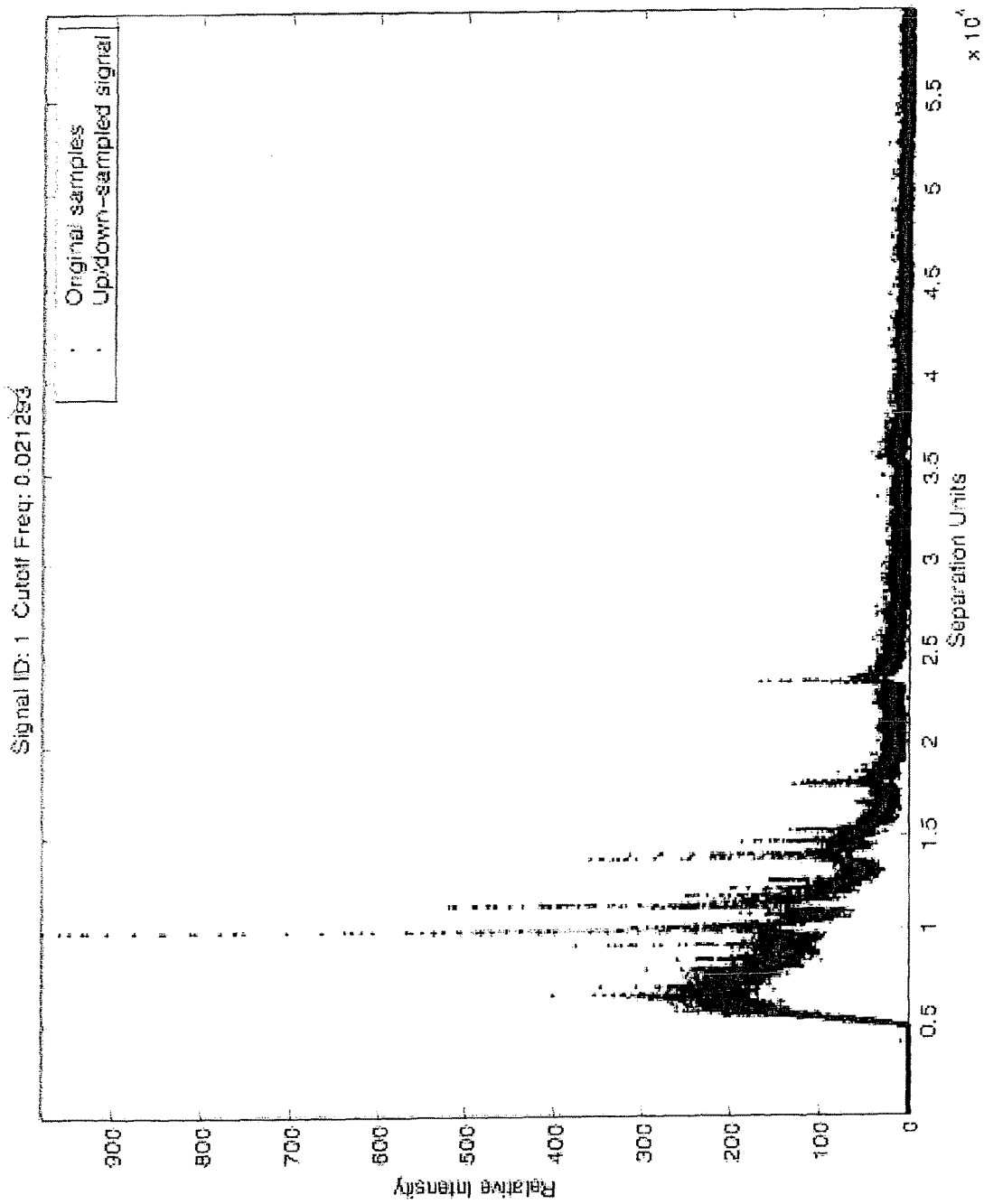
FIGS. 1a and 1b show a typical MS profile before and after resampling to 1000 data points.
Figure 1B:
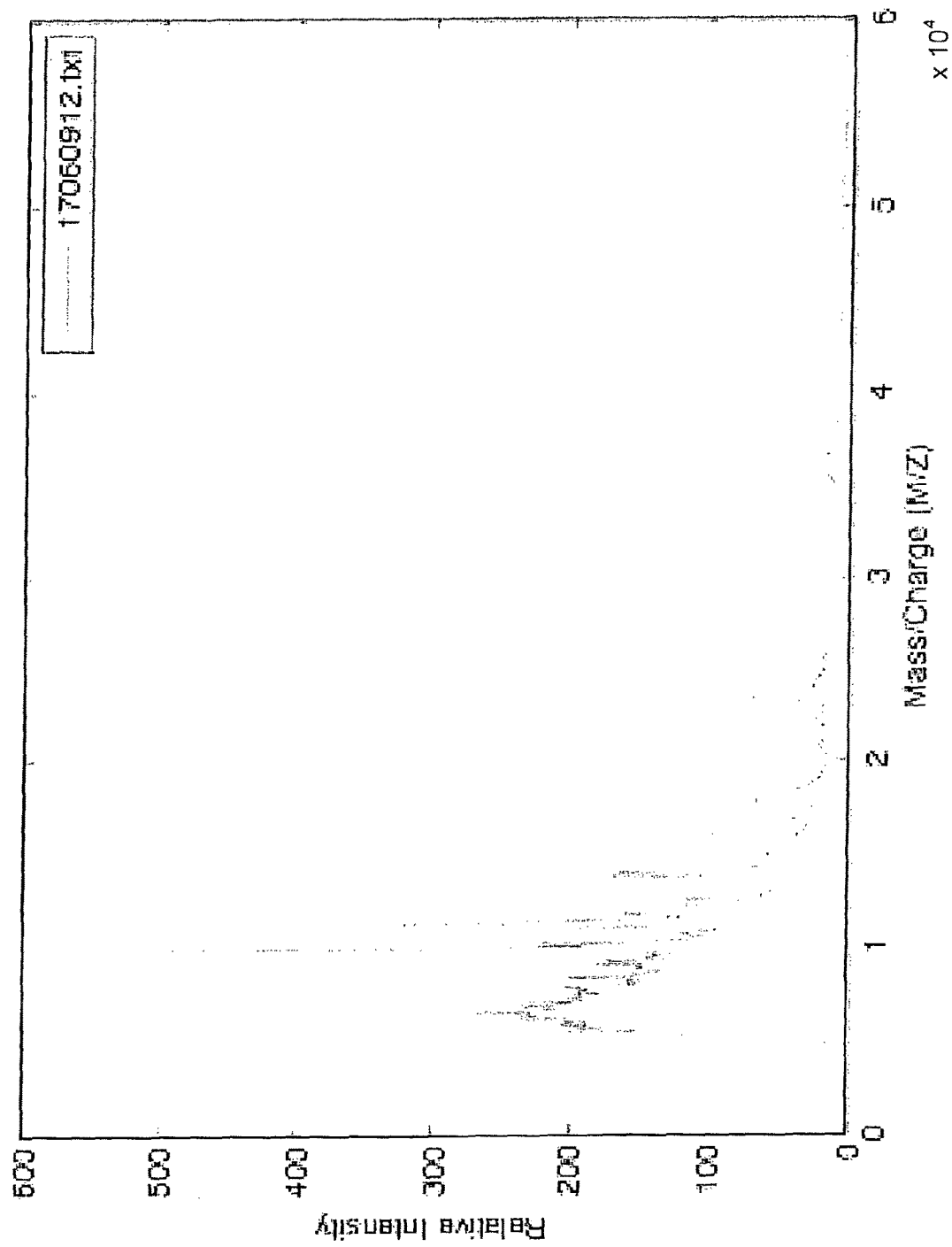

Re-sampling of MS profiles is performed using the 'msresample' function from the MATLAB Bioinformatics Toolbox (http://tinyurl.com/msresample). This allows the up-sampling and down-sampling of the original signal, whilst preserving the information contained within the spectra. FIGS. 1a and 1b show a typical 96 DWP spectrum before and after application of re-sampling.

Typically re-sampling is utilised in situations where the original high resolution MS signal would be considered impractical to work with due to computational constraints such as lack of computer memory. Re-sampling can also be used to create a consistent m/z range, which facilitates lining up multiple spectra. Care must be taken when re-sampling MS profiles so as not to set the number of re-sampled units too low. This will cause the signals to lose resolution and can result in a loss of features.

5.3 Baseline Correction of MS Profiles

Figure 2A:
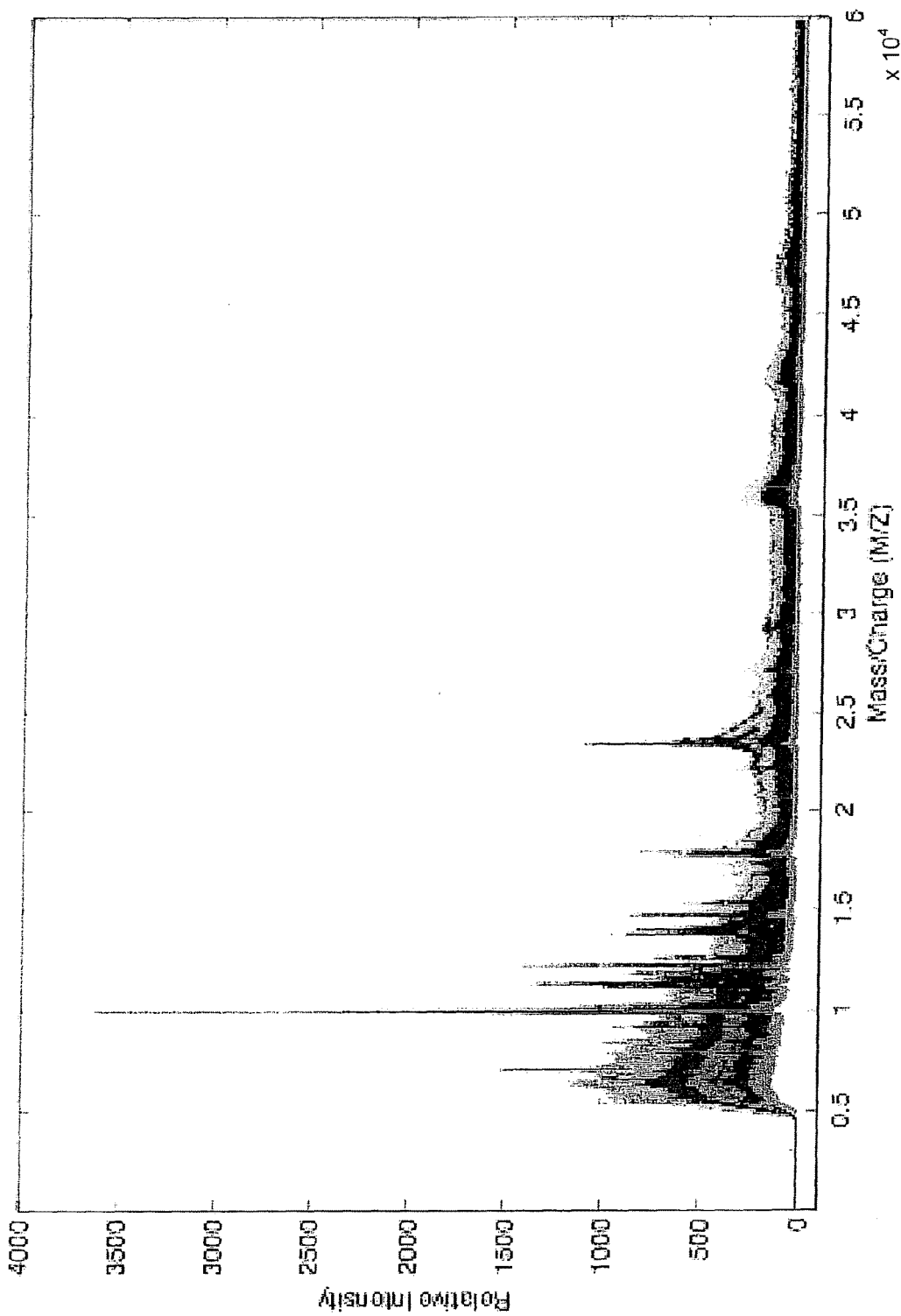
FIGS. 2a and 2b show typical MS profiles before and after baseline correction.
Figure 2B:
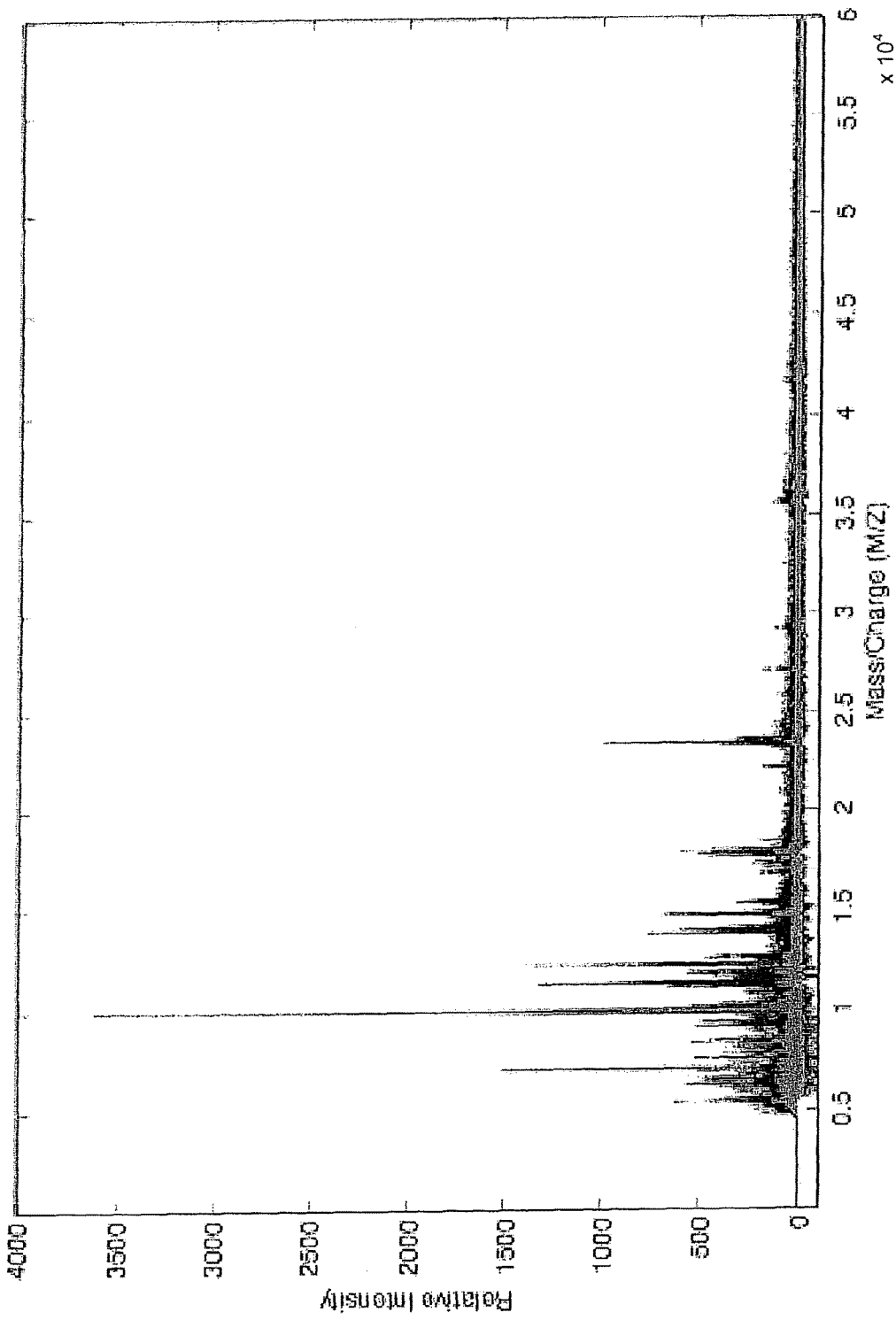

MS data profiles typically exhibit a varied baseline due to issues such as chemical noise in the MALDI matrix and ion overloading. This can be undesirable when using data analysis techniques to compare MS profiles as they utilise distance metrics to measure the similarity between profiles. It is therefore preferred to remove these effects prior to any form of comparative analysis of the signals. This is performed using the 'msbackadj' function in the MATLAB Bioinformatics Toolbox (http://tinyurl.com/msbackadj). FIGS. 2a and 2b show a selection of typical 96 DWP spectra before and after application of baseline correction.

When applying a number of spectral pre-treatments in series, baseline correction should be used after down-sampling and prior to correcting the calibration, as the noise present will impact on the result.

5.4 Normalisation

Figure 3A:
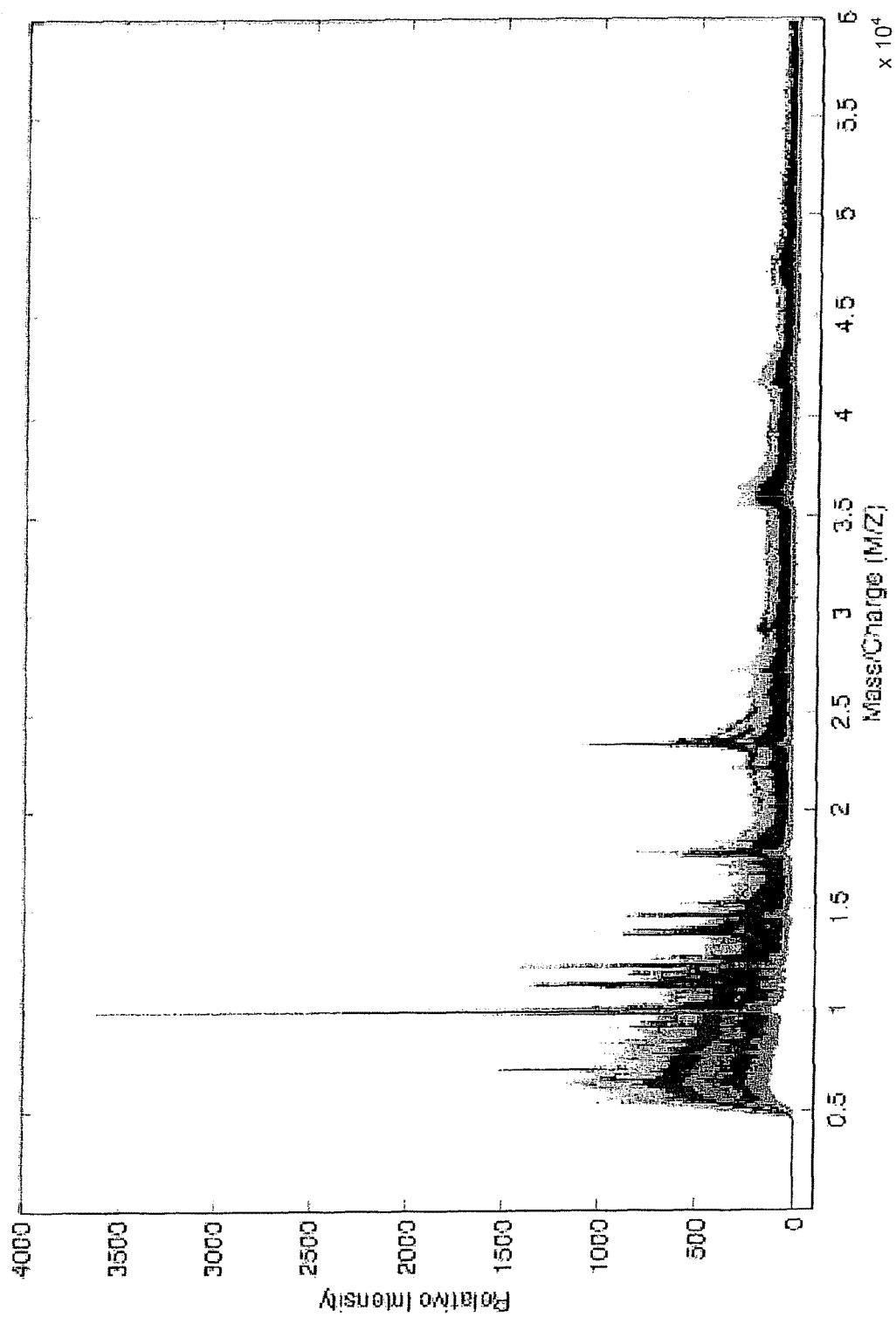
FIGS. 3a and 3b show typical MS profiles before and after normalisation.
Figure 3B:
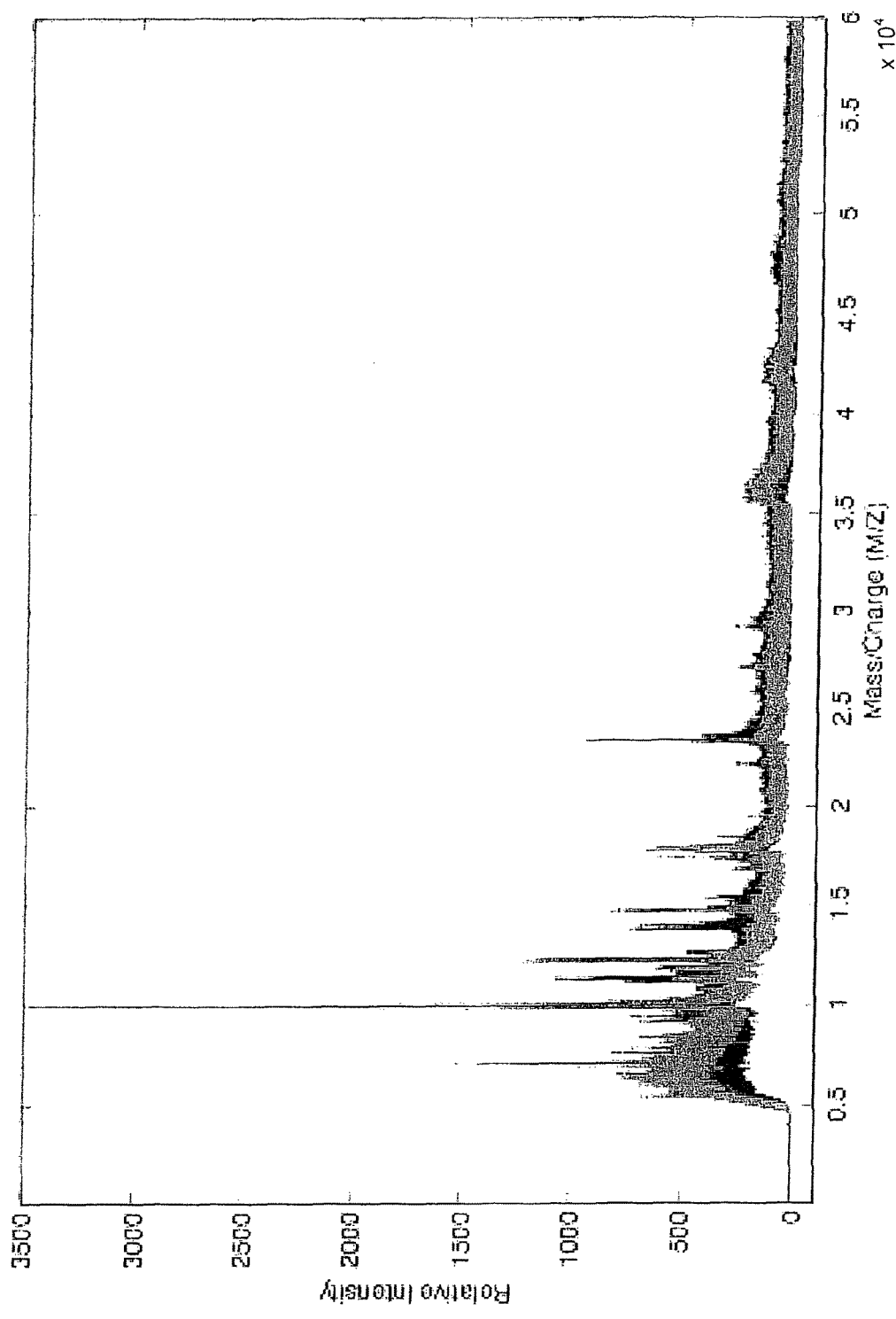

Another commonly observed phenomenon with MS profiles is a variation in the amplitude of the ion intensities. This can be caused by a number of factors, such as variation in the sample preparation or changes in the sensitivity of the instrument. The standard procedure to account for this variation is to normalise the area under the MS curves to that of the group average (typically the mean or median is used). This is performed using the 'msnorm' function from the MATLAB Bioinformatics Toolbox (http://tinyurl.com/msnormal). FIGS. 3a and 3b show a selection of typical 96 DWP spectra before and after normalisation of the area under the curve.

When applying a number of spectral pre-treatments in series, normalisation of the samples should be performed after subtracting the baseline as the noise element introduced by the crystallisation matrix can impact on the results.

5.5 MS Alignment

Peak alignment is used to correct variation between the observed m/z value and true time of flight. These errors usually occur as a result of calibration errors and can be observed as a systematic shift between peaks. Correction of these inconsistencies can be performed using the 'msalign' function from the MATLAB Bioinformatics Toolbox (http://tinyurl.com/msalign).

One method to align spectra is to spike the samples with a substance with a known spectral profile, and align the samples based on this. However, in situations where the samples have not been spiked, samples can be aligned relative to reference spectra such as the mean profile.

5.6 Filtering of MS Profiles

Figure 4A:
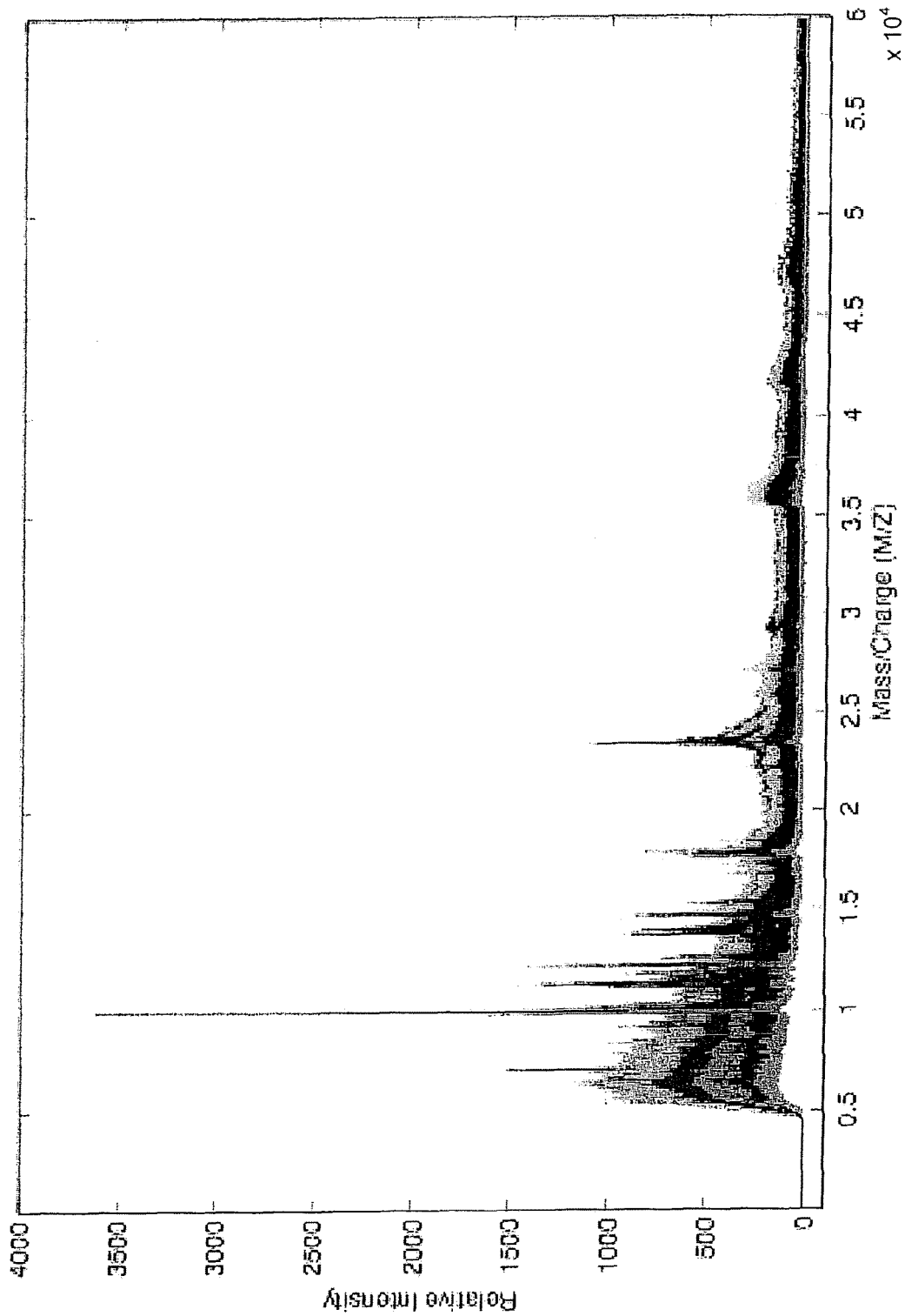
FIGS. 4a and 4b show typical MS profiles before and after Savitzky-Golay smoothing.
Figure 4B:
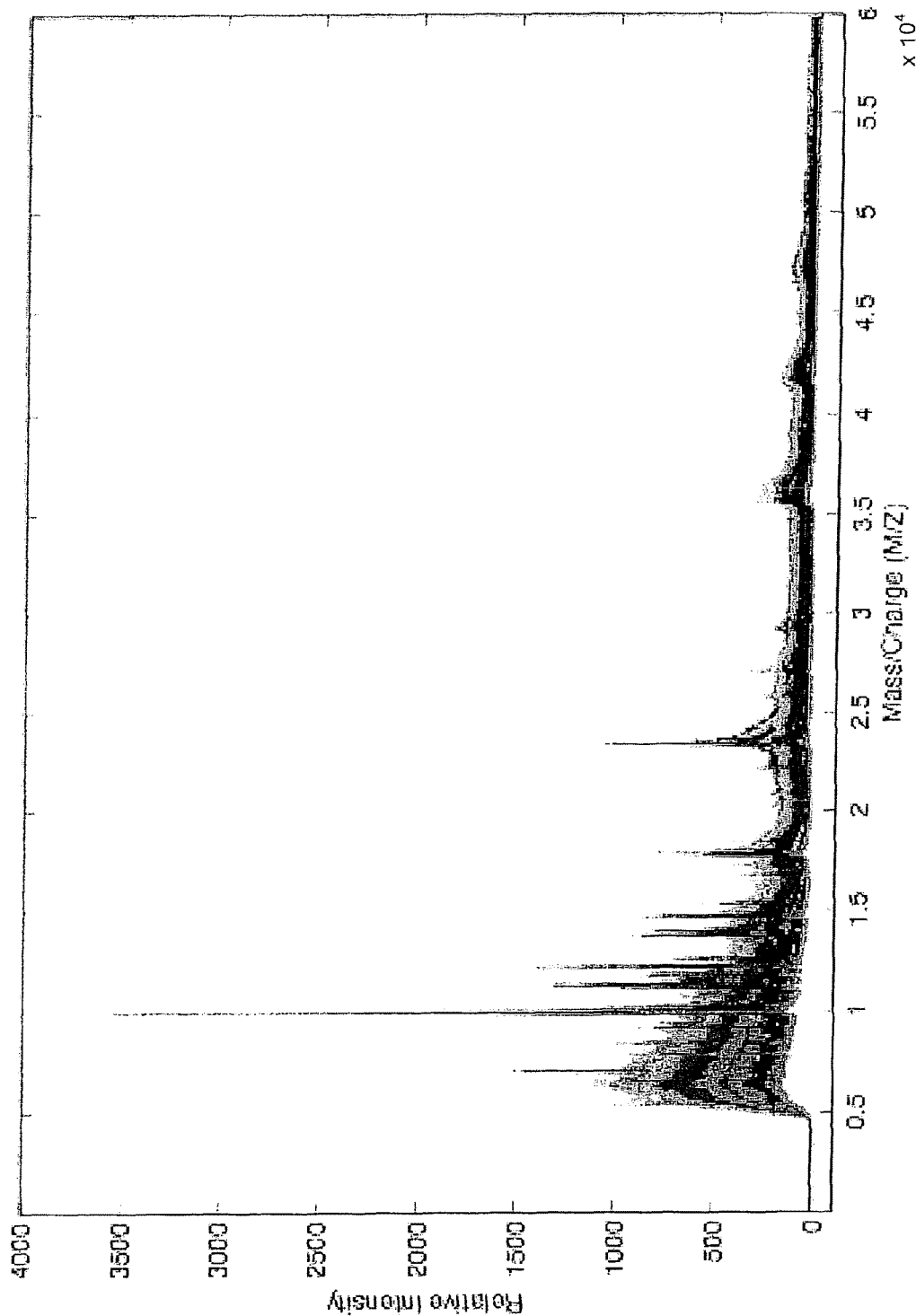

A typical MS profile contains a mixture of both signal and noise. Smoothing of the signal by use of a Savitzky-Golay filter can help to reduce the impact of the noise component of the signal during subsequent processing. Savitzky-Golay filters are typically applied to MS signals as they use high order polynomials to fit the curves. This results in greater preservation of the features in the signal, such as the peak heights. This process is performed using the 'mssgolay' function from the MATLAB Bioinformatics Toolbox (http://tinyurl.com/mssgolay). FIGS. 4a and 4b show a selection of typical 96 DWP spectra before and after application of Savitzky-Golay filtering.

5.7 Cropping of MS Profiles

Figure 5A:
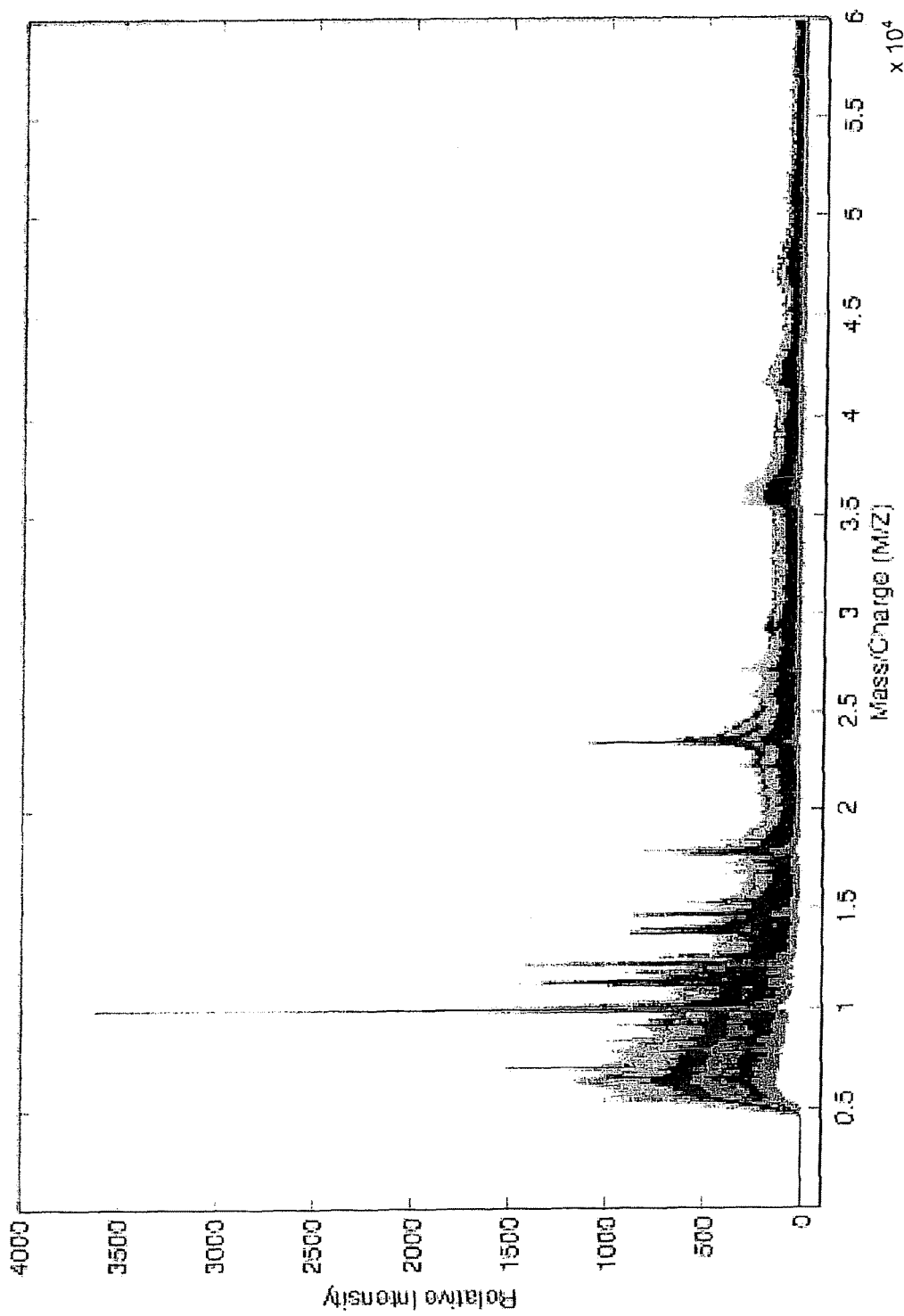
FIGS. 5a and 5b show typical MS profiles before and after cropping regions of the spectra with little or no information.
Figure 5B:
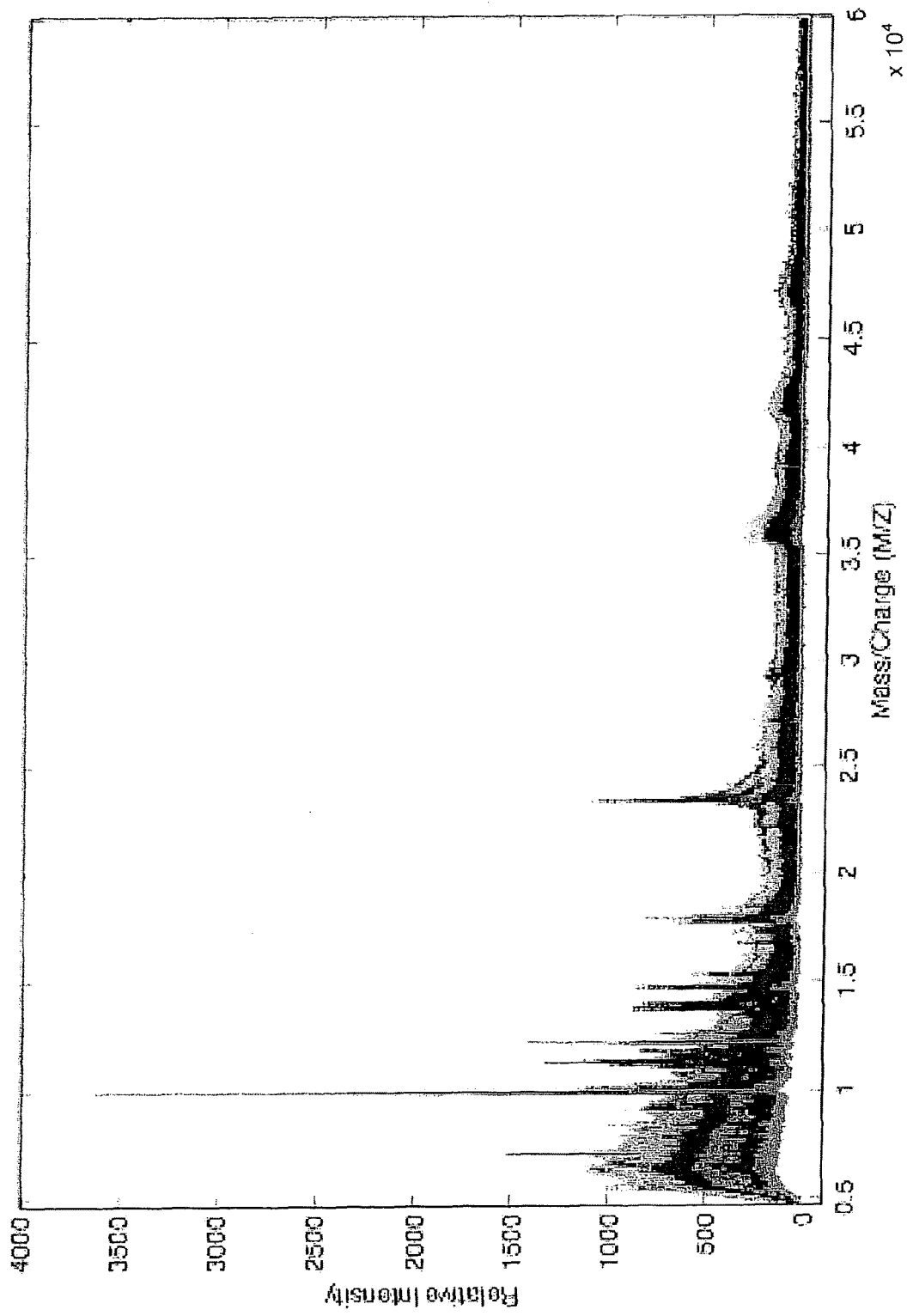

Cropping of the MS profiles is performed to remove parts of the signal containing little or no information. It also allows the spectra to be divided into subsections. This enables specific regions of the MS profiles to be analysed rather than the whole spectra. FIGS. 5a and 5b show a selection of typical 96 DWP spectra before and after cropping of the signal in the range of from 0 to 500 m/z.

5.8 Comparing the Effects of Pre-Treatment

Figure 6A:
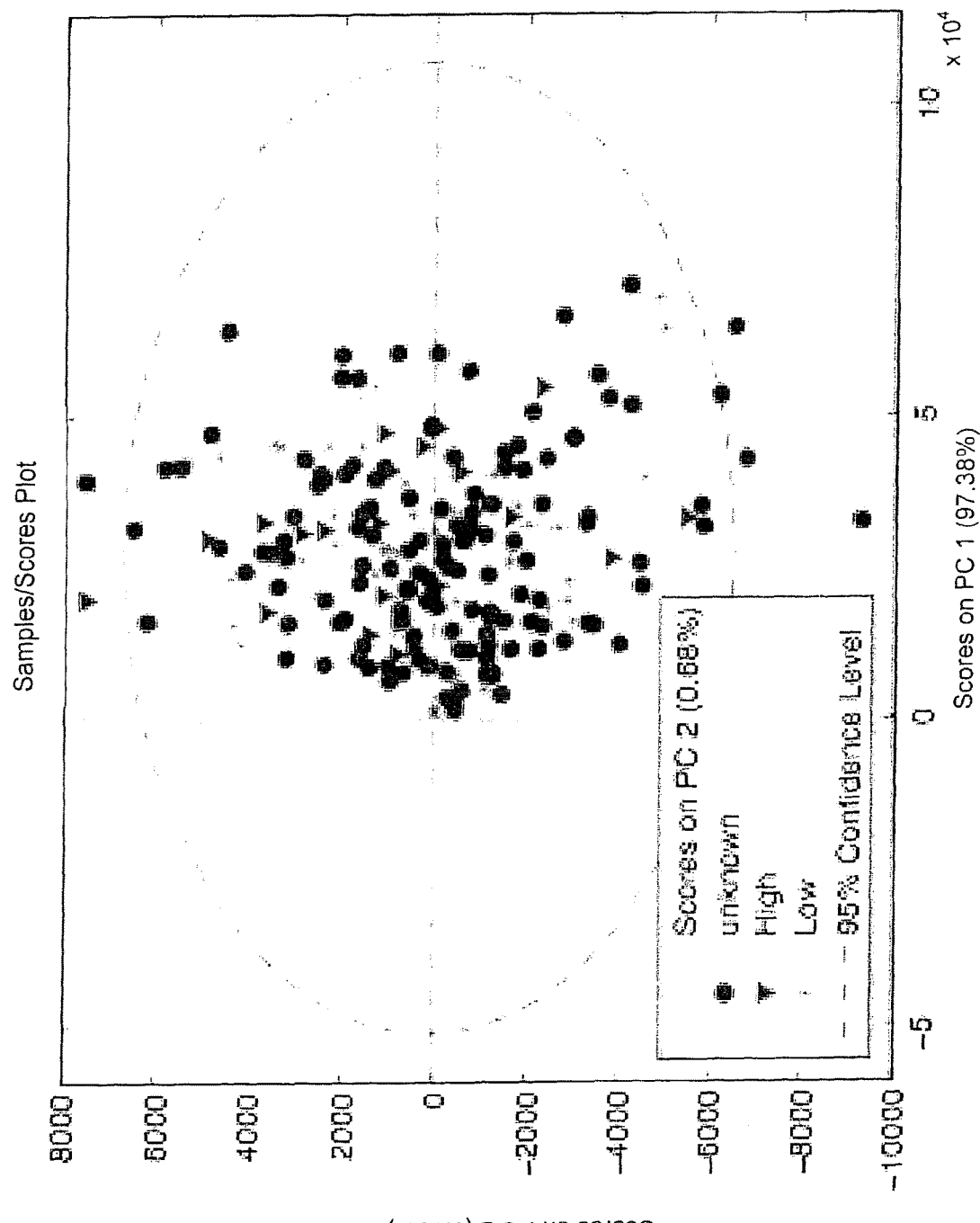
FIGS. 6a, 6b and 38 show a score plot of PC1 versus PC2 using raw MS profiles (6a, 38) and with a typical associated MS profile (6b).
Figure 6B:
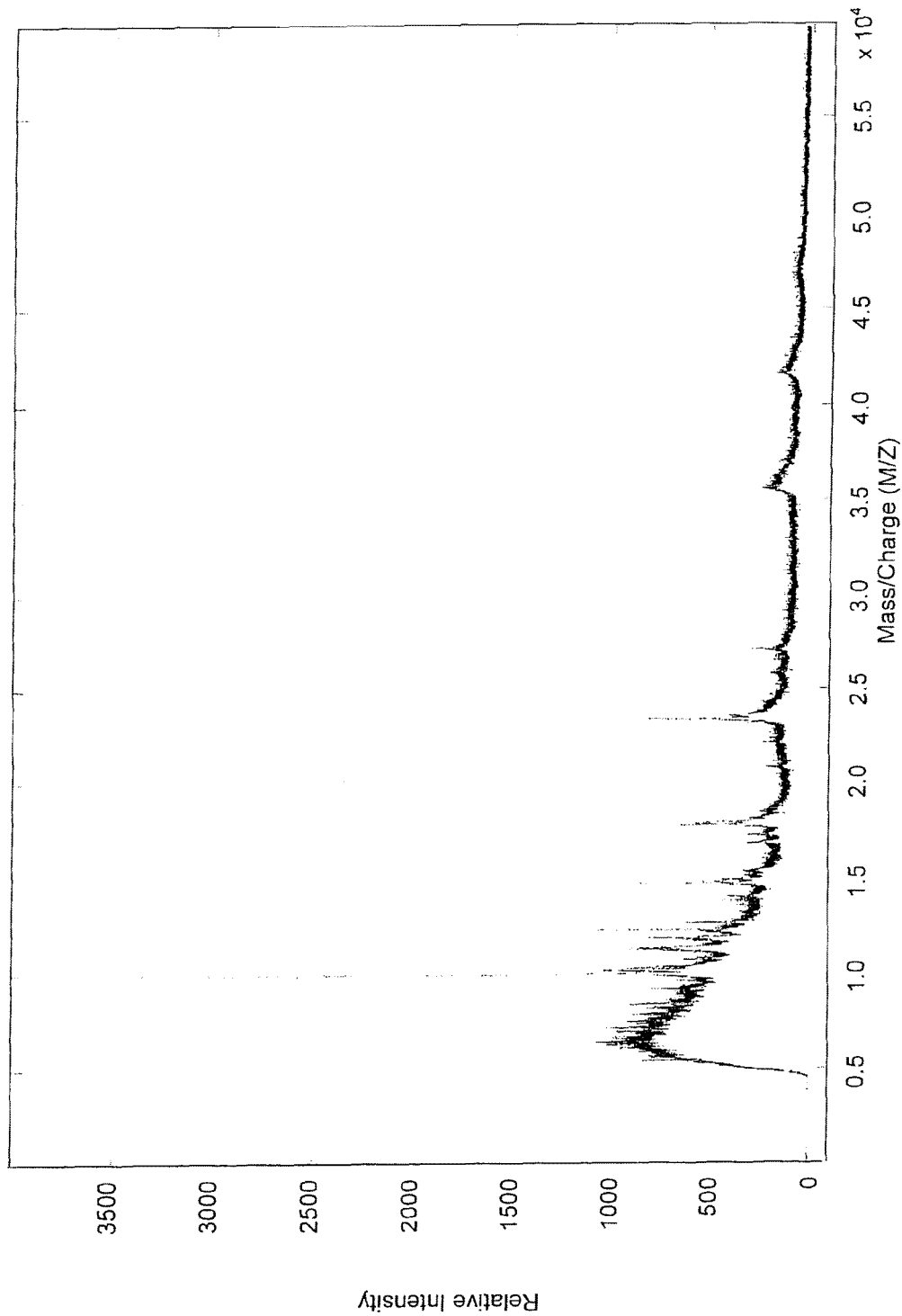
Figure 38:
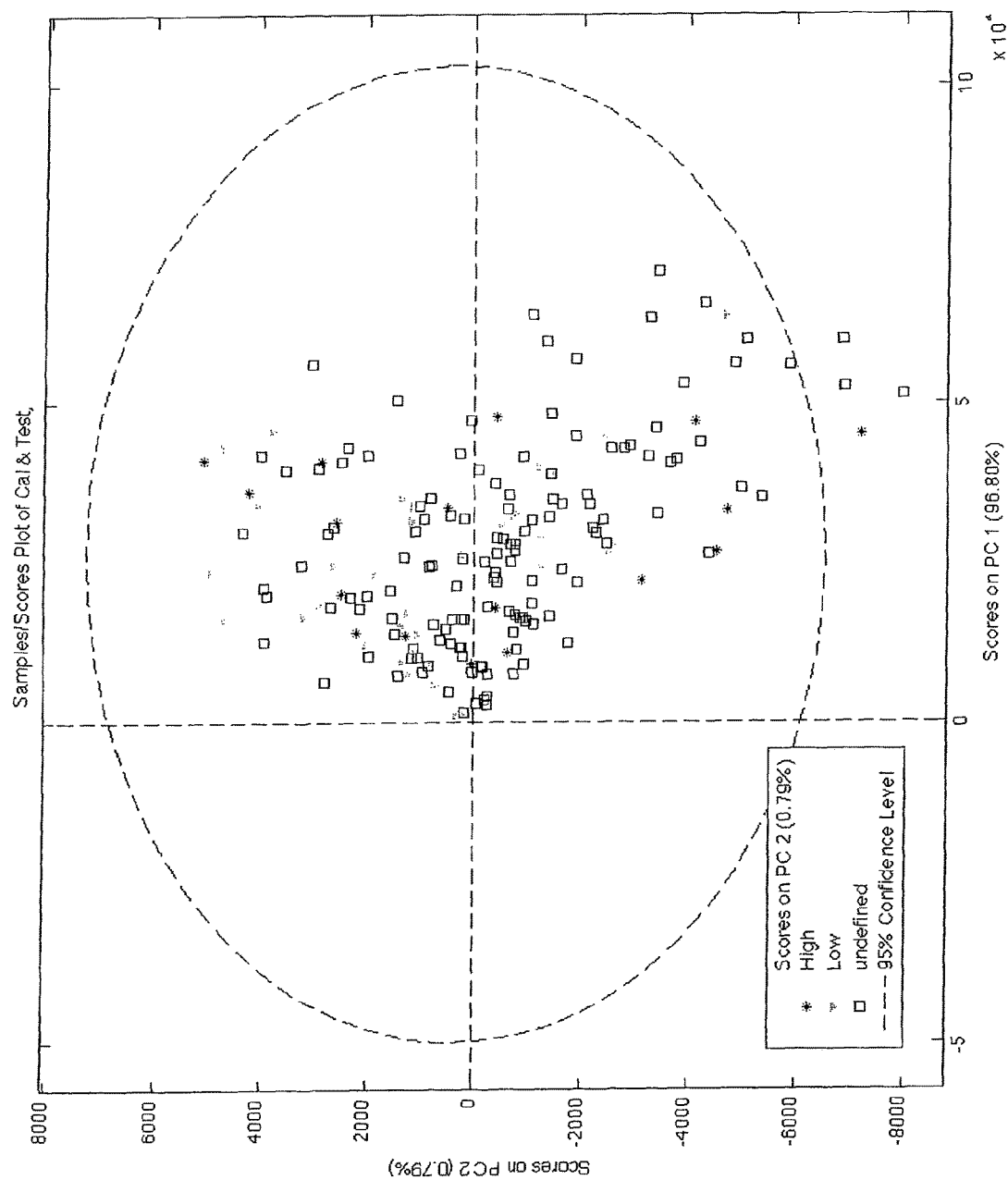

To demonstrate the effect of applying signal processing techniques to MS data, a group of 118 cell lines (measured in duplicate) were analysed using Principal Component Analysis (PCA). FIGS. 6a, 6b and 38 show the principal component scores plot of PC1 vs. PC2. This plot describes the two major sources of variation in the data set.

Figure 7A:
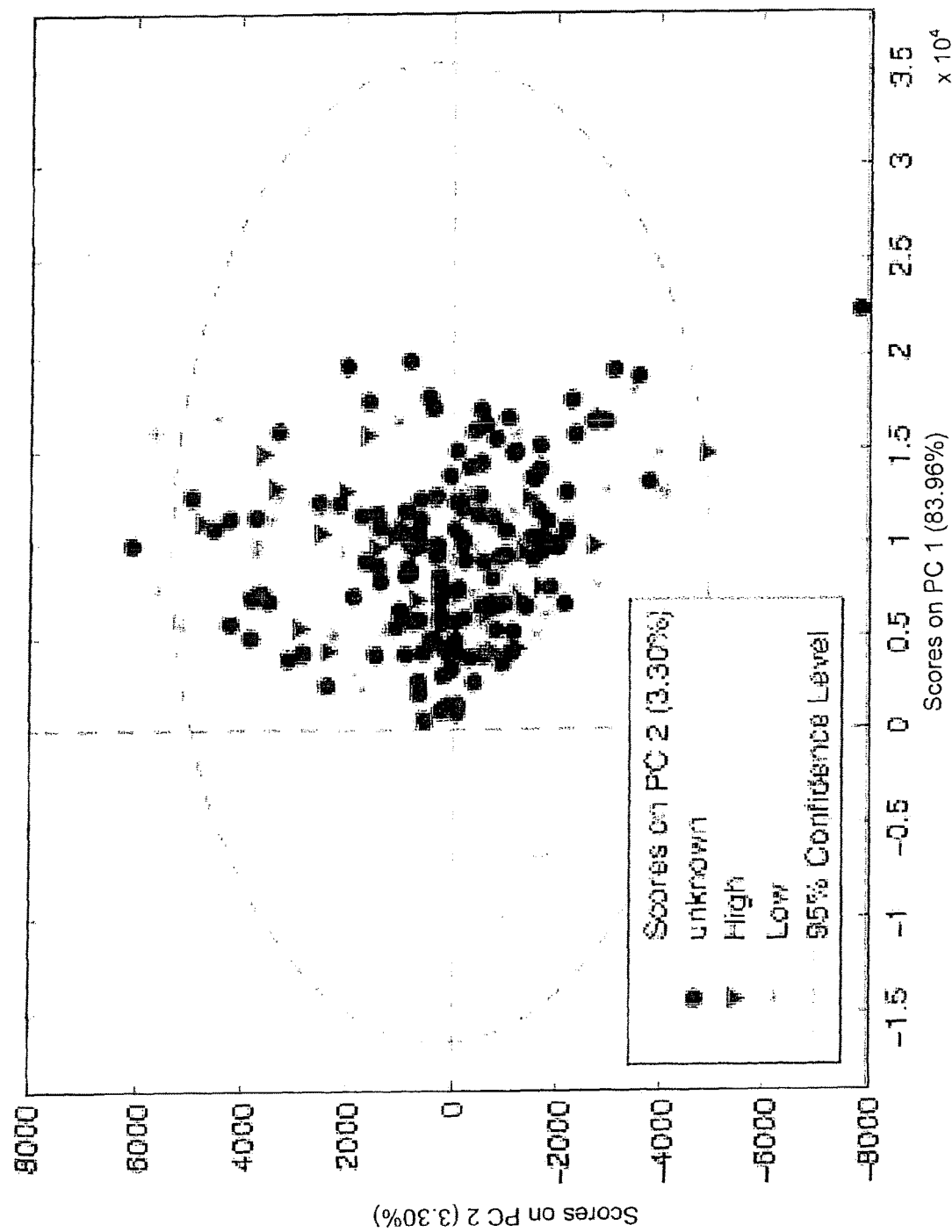
FIGS. 7a, 7b and 39 show a score plot of PC1 versus PC2 using MS profiles subjected to baseline correction (7a, 39) with a typical associated MS profile (7b).
Figure 7B:
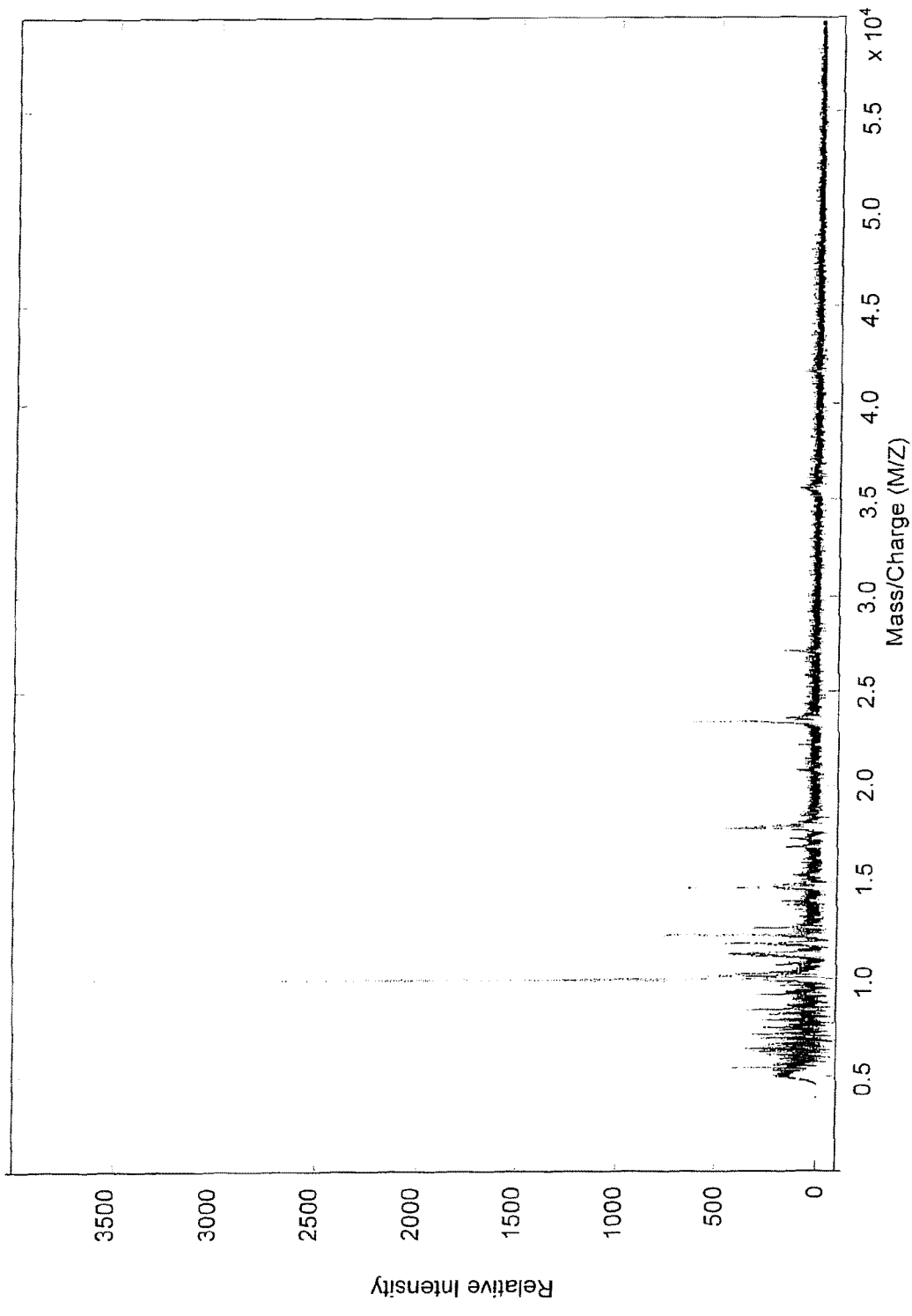
Figure 39:
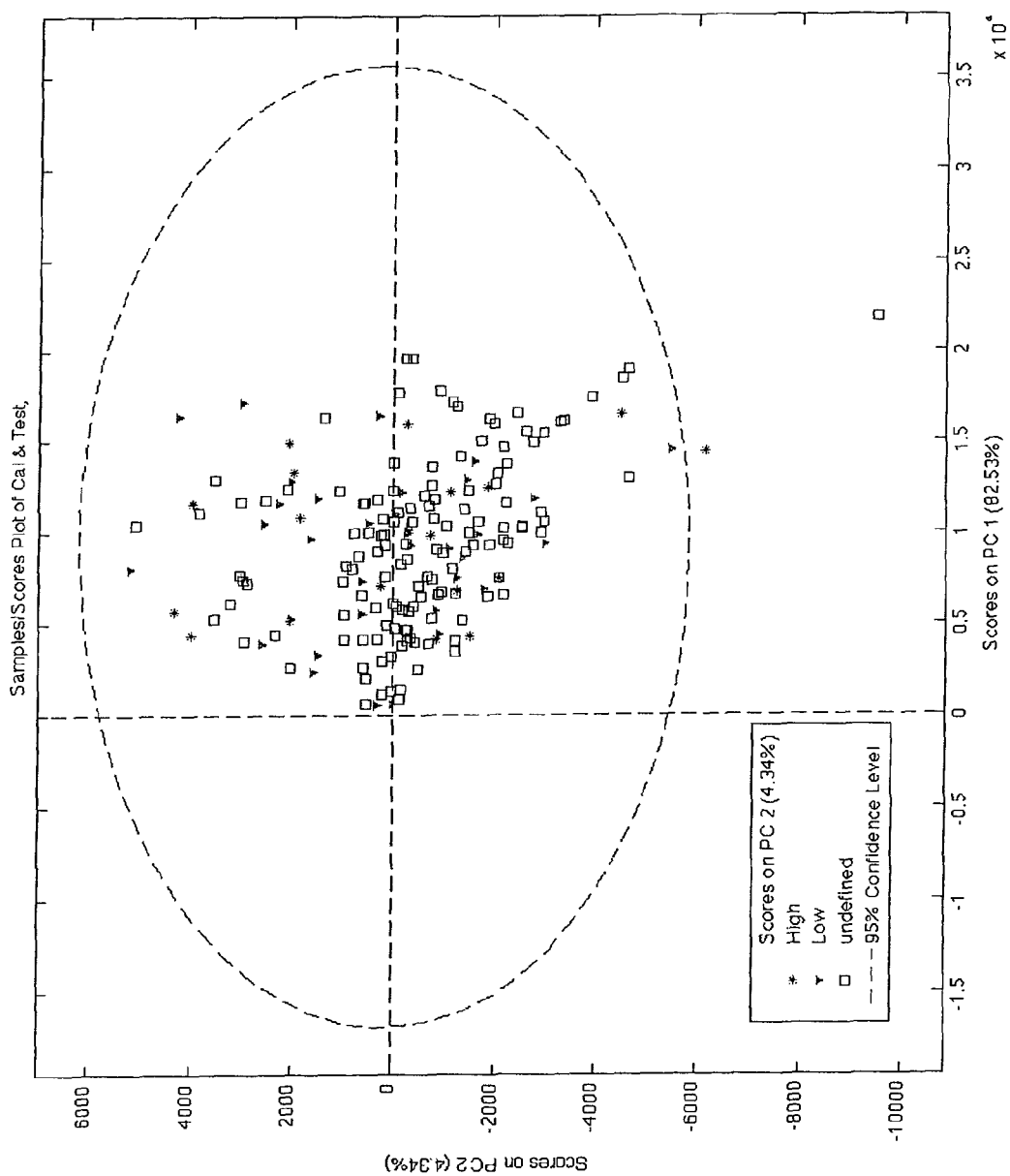

Application of baseline correction to the raw MS profiles results in a reduction of the amount of scatter observed in the first and second principal components. This can be observed in FIGS. 7a, 7b and 39.

Figure 8A:
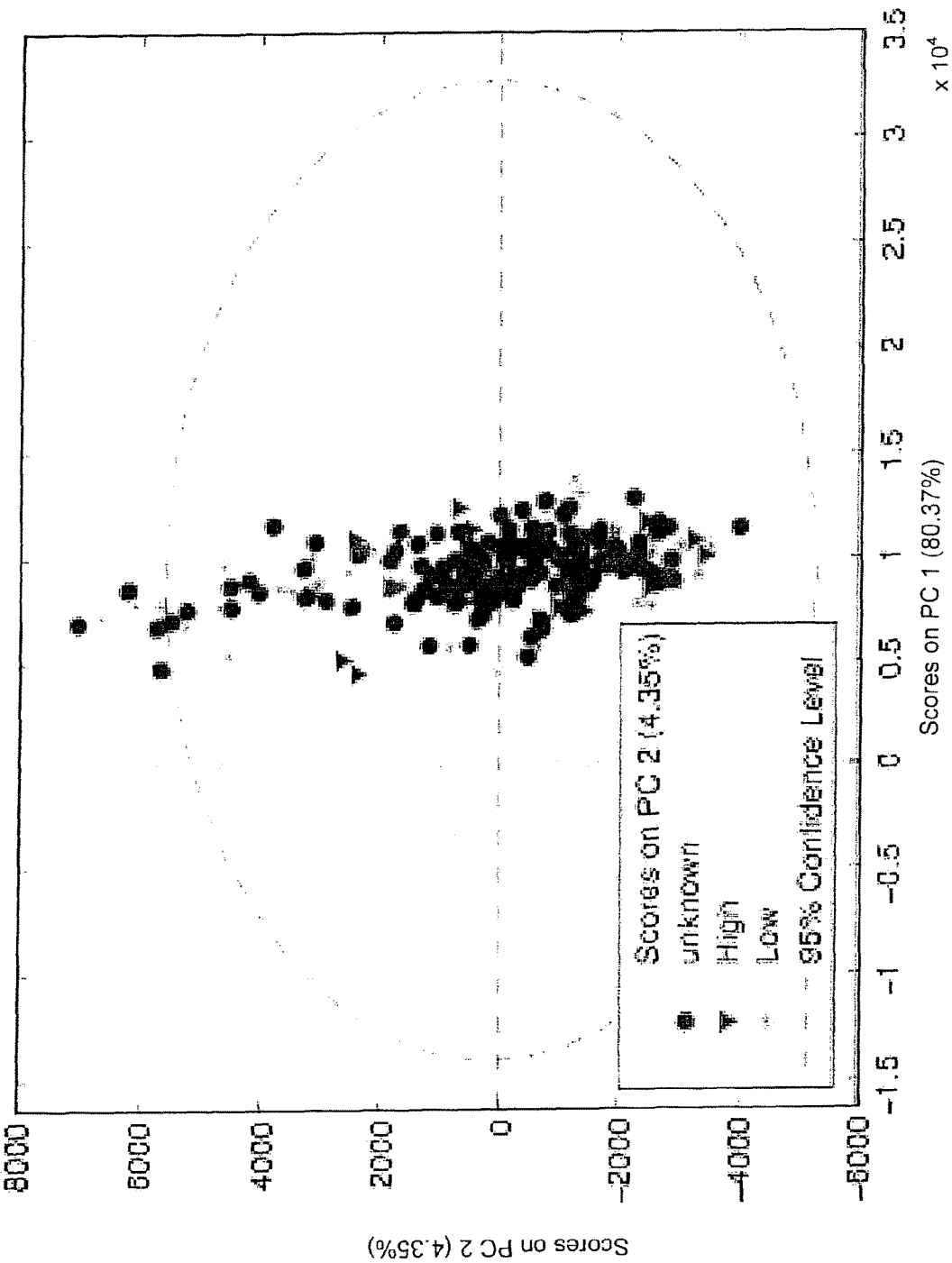
FIGS. 8a, 8b and 40 show a score plot of PC1 versus PC2 using MS profile subjected to baseline correction and normalisation (8a, 40) with a typical associated MS profile (8b).
Figure 8B:
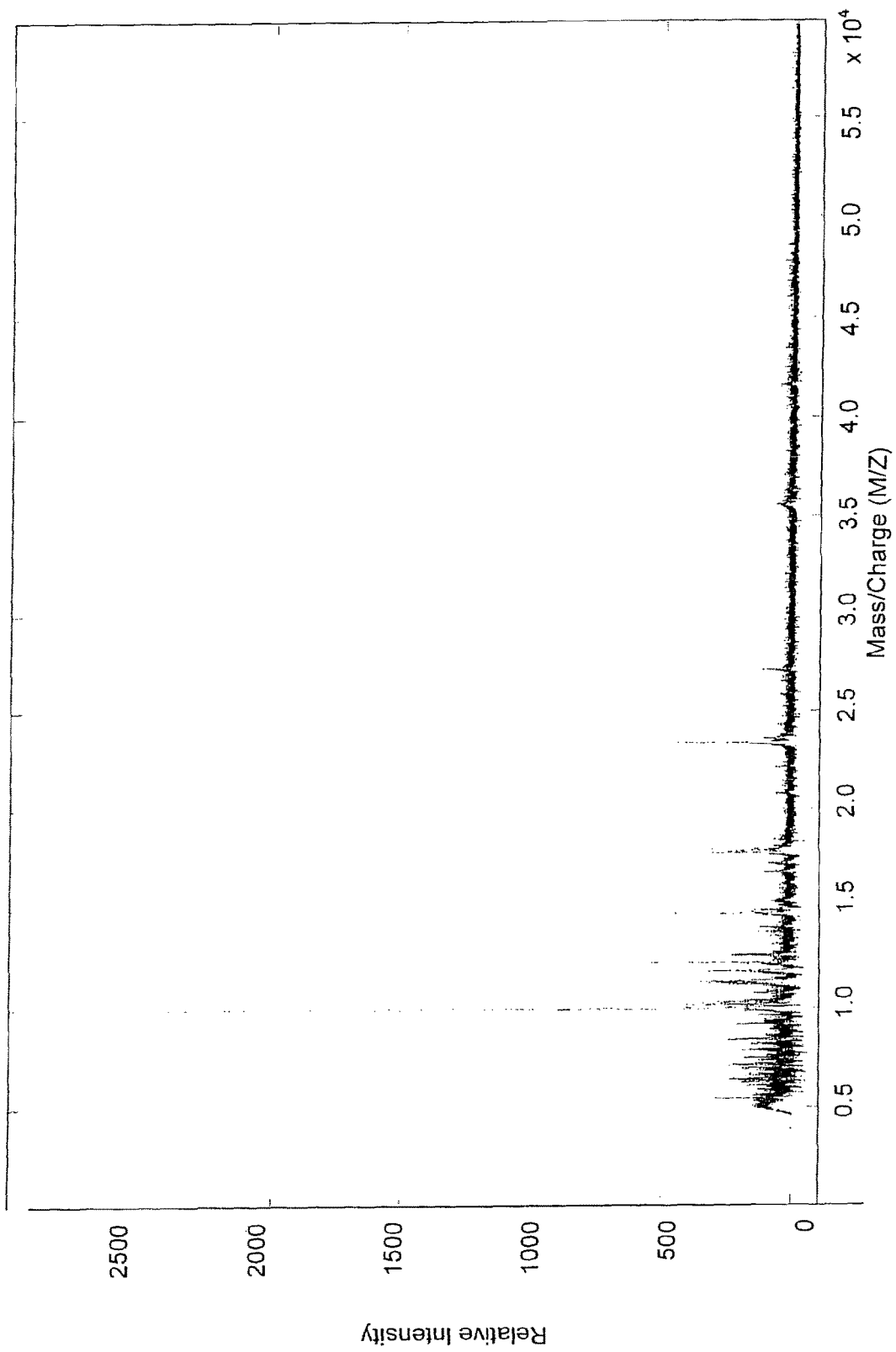
Figure 40:
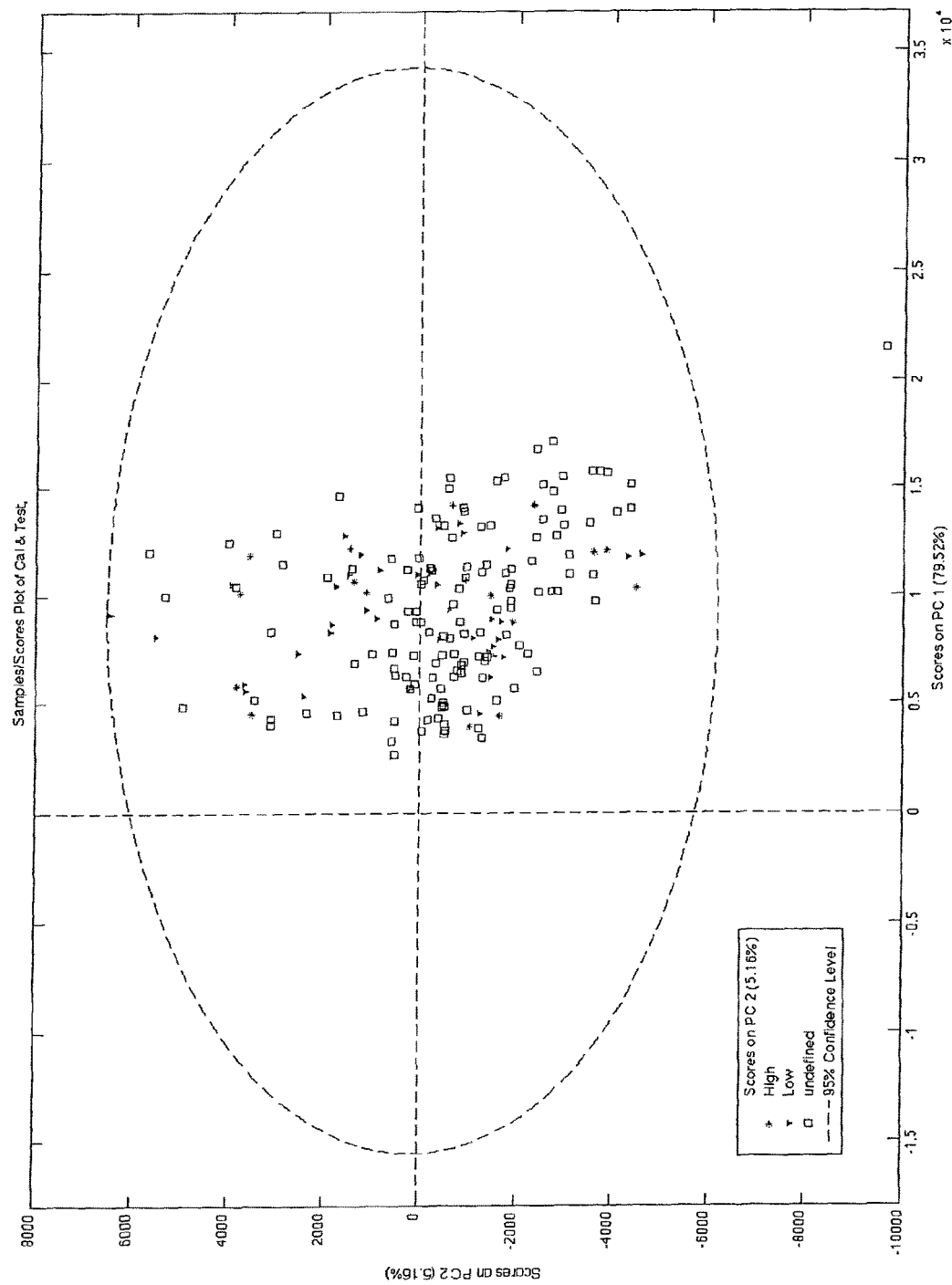

Baseline correction only accounts for the noise in the signal due to the MALDI matrix. It is preferred that the variation in the amplitudes of the signal be removed using normalisation. FIGS. 8a, 8b and 40 show the effect of applying normalisation on the group of spectra. It clearly shows a reduction in the variation observed in PC1, the major source of variation.

Figure 9A:
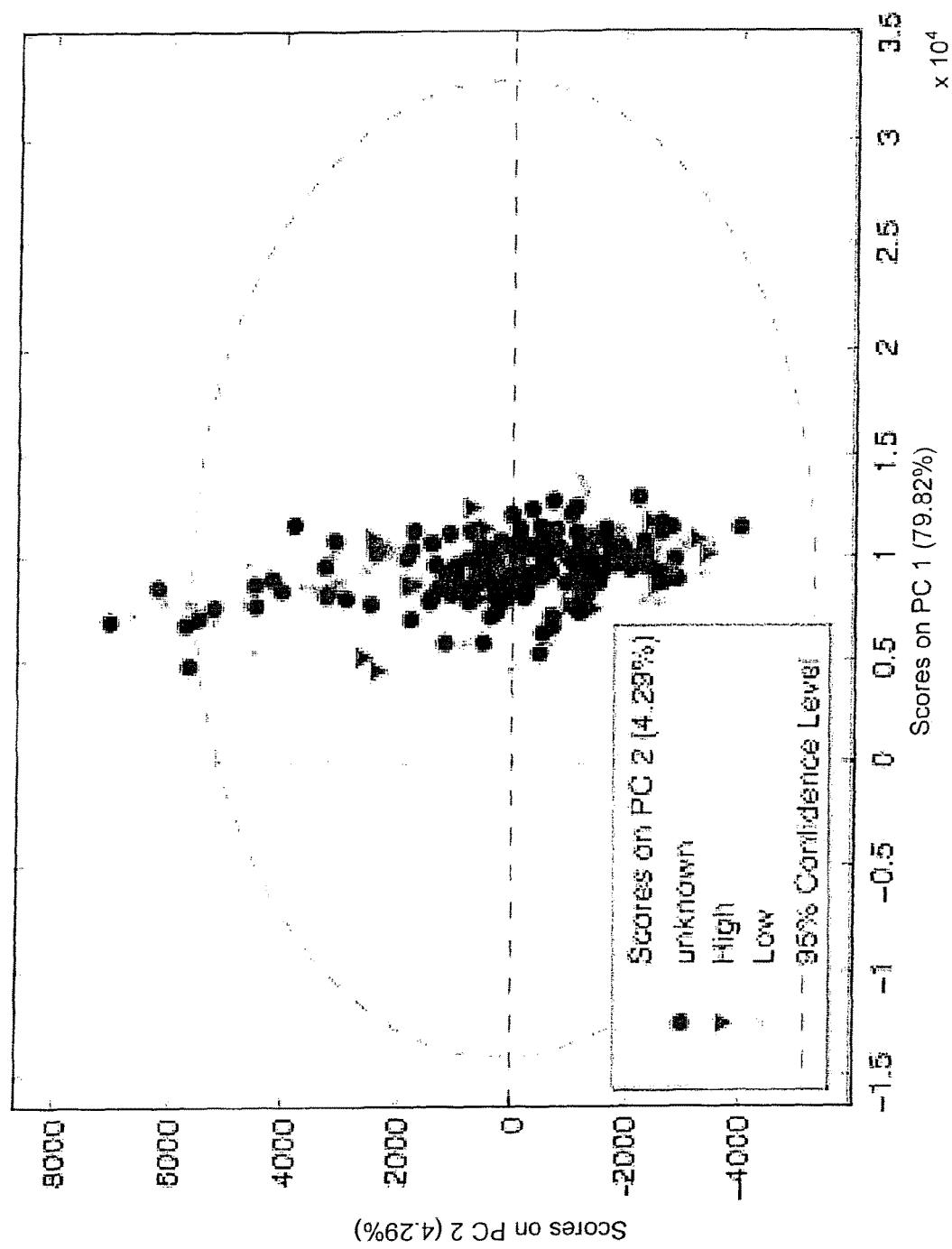
FIGS. 9a, 9b and 41 show a score plot of PC1 versus PC2 using MS profiles subjected to baseline correction, normalisation and cropping (9a, 41) with a typical associated MS profile (9b).
Figure 9B:
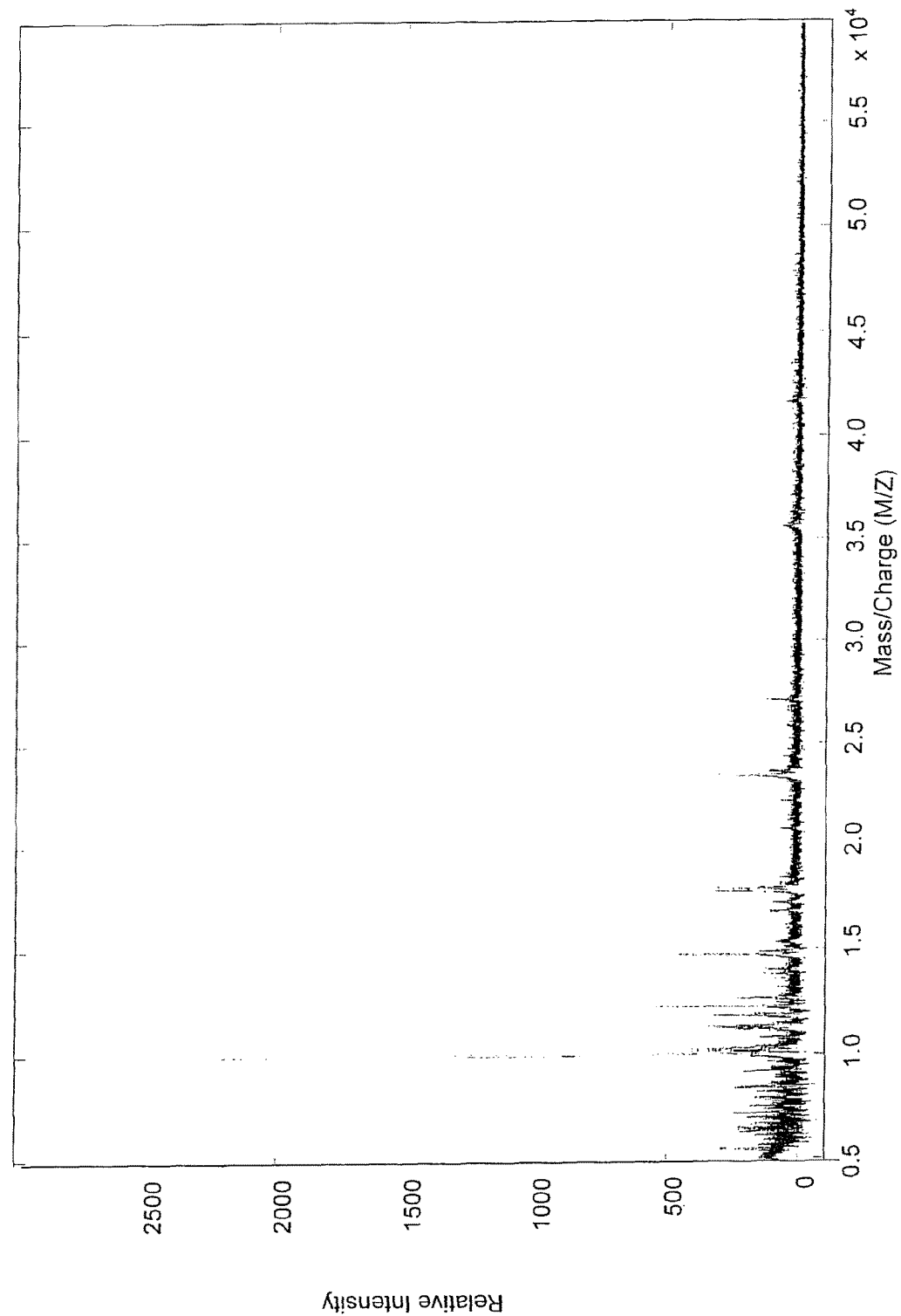
Figure 41:
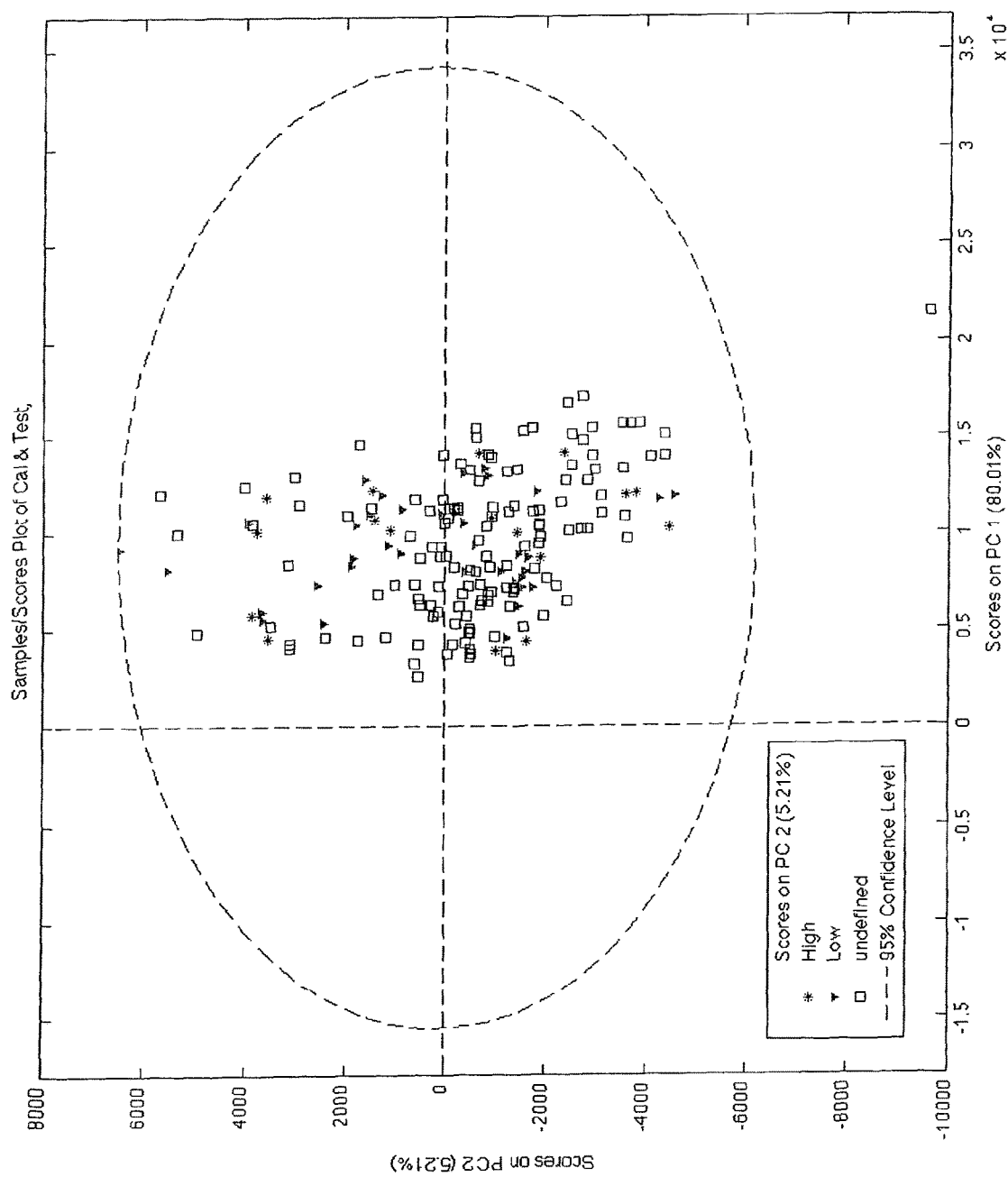
Figure 42:
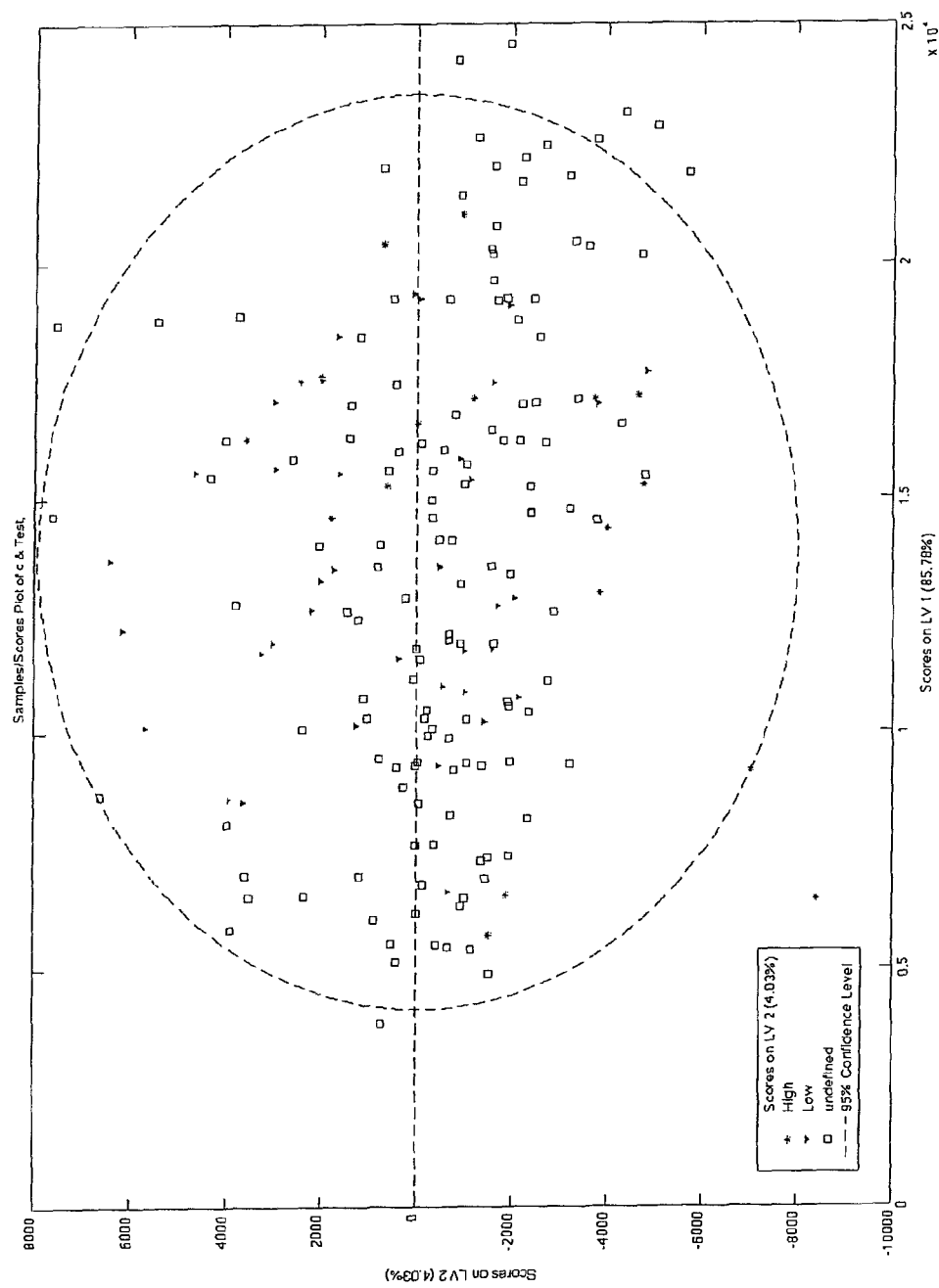
Figure 43:
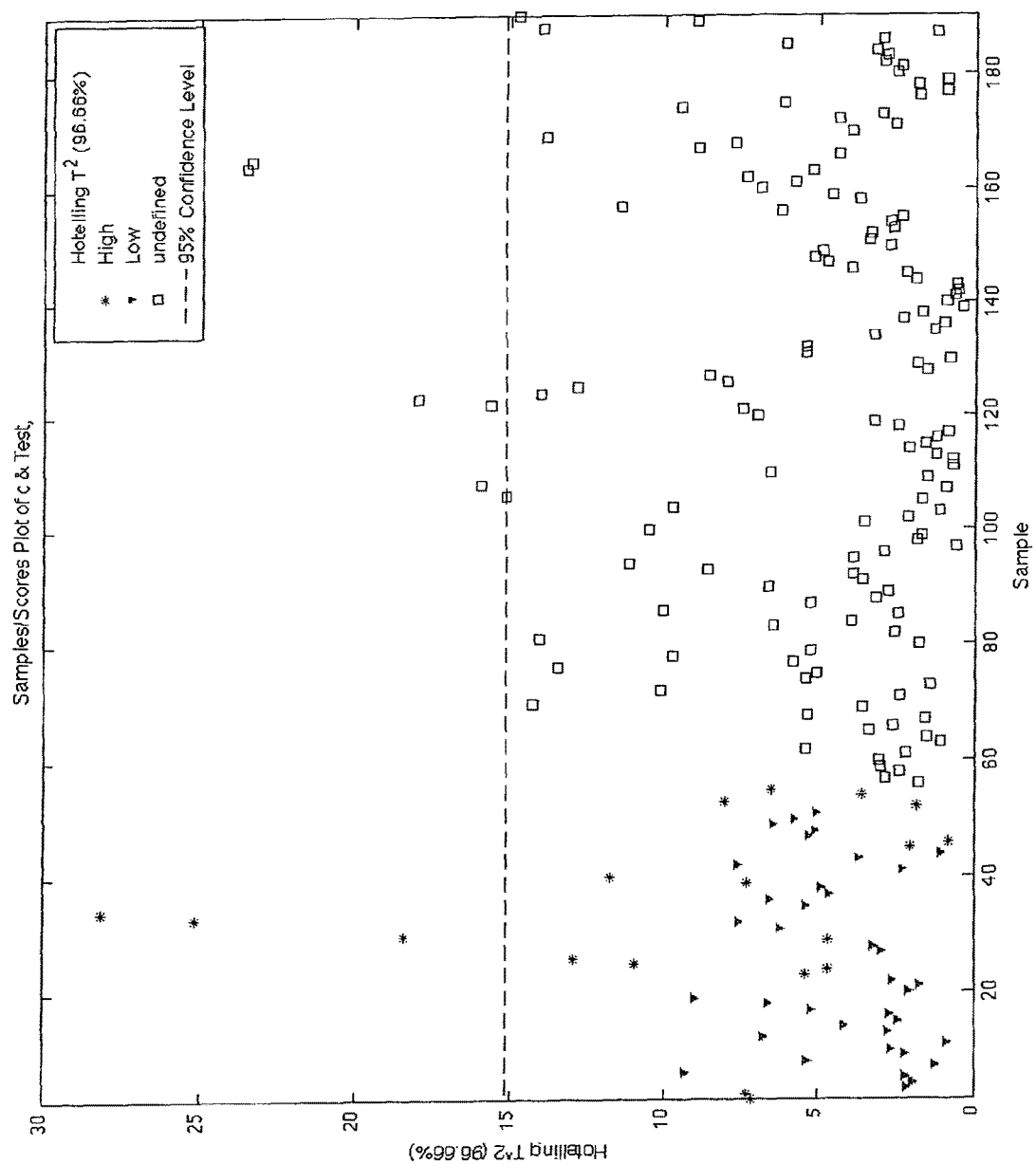
Figure 44:
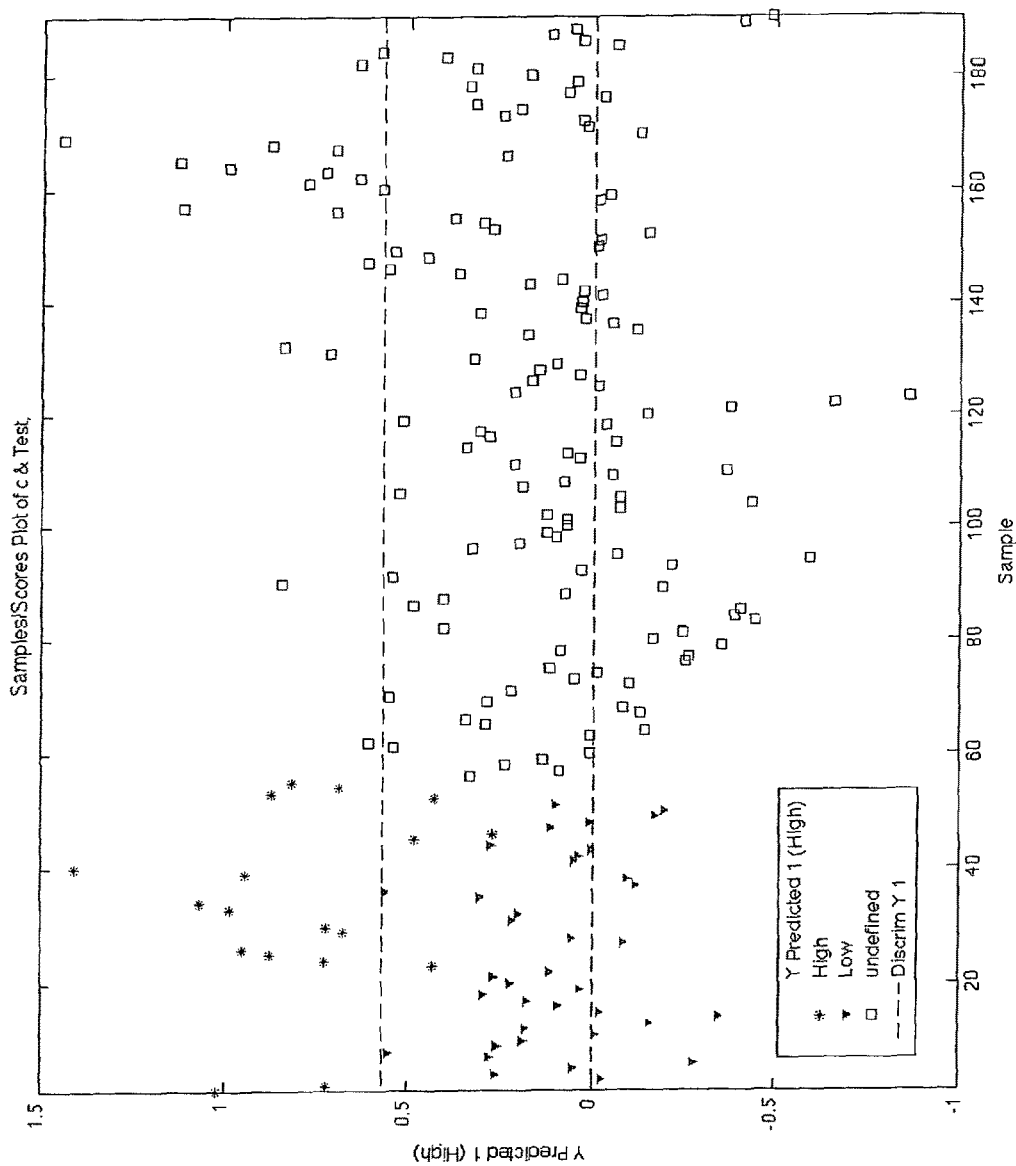
Figure 45:
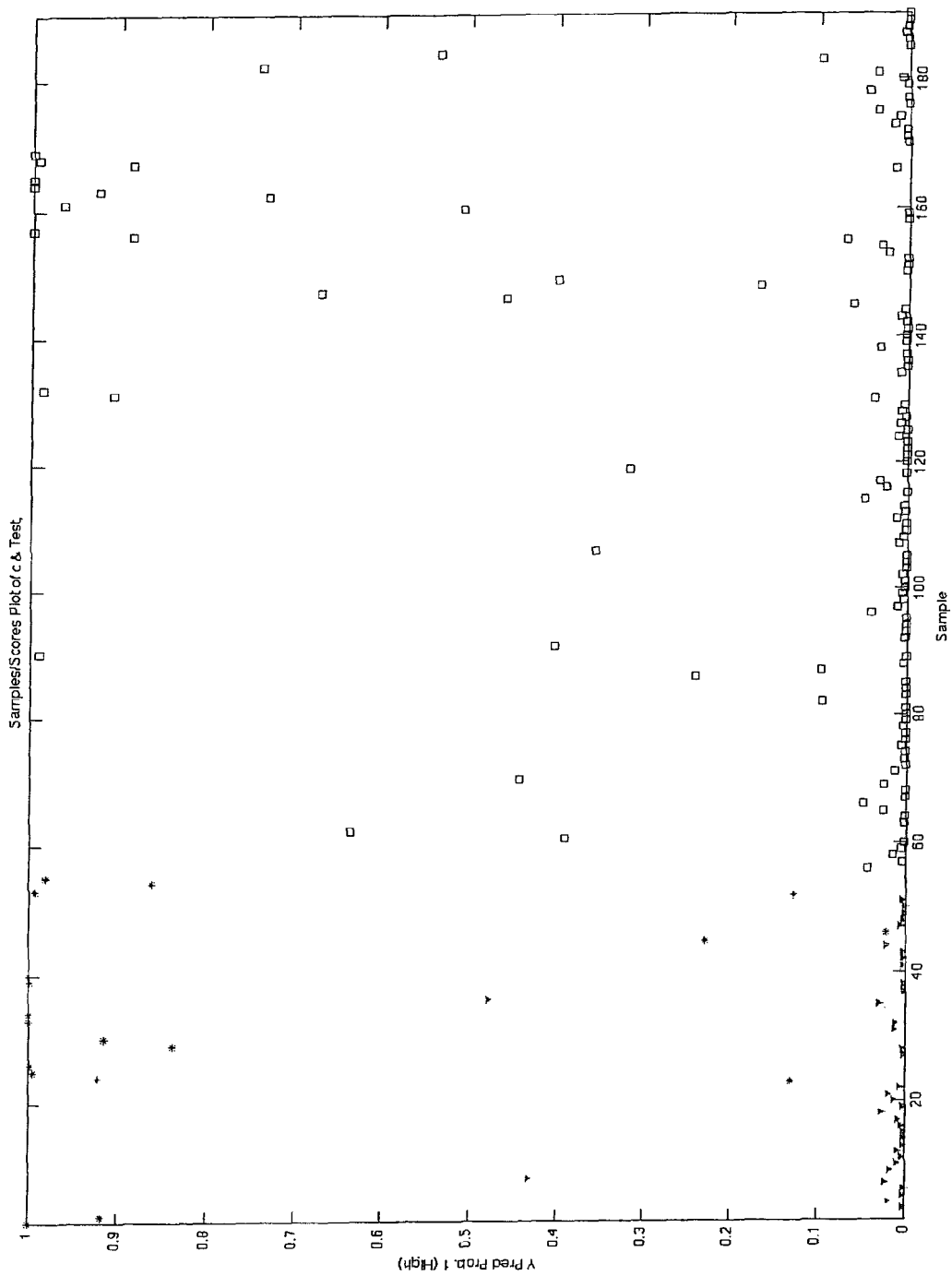
Figure 46:
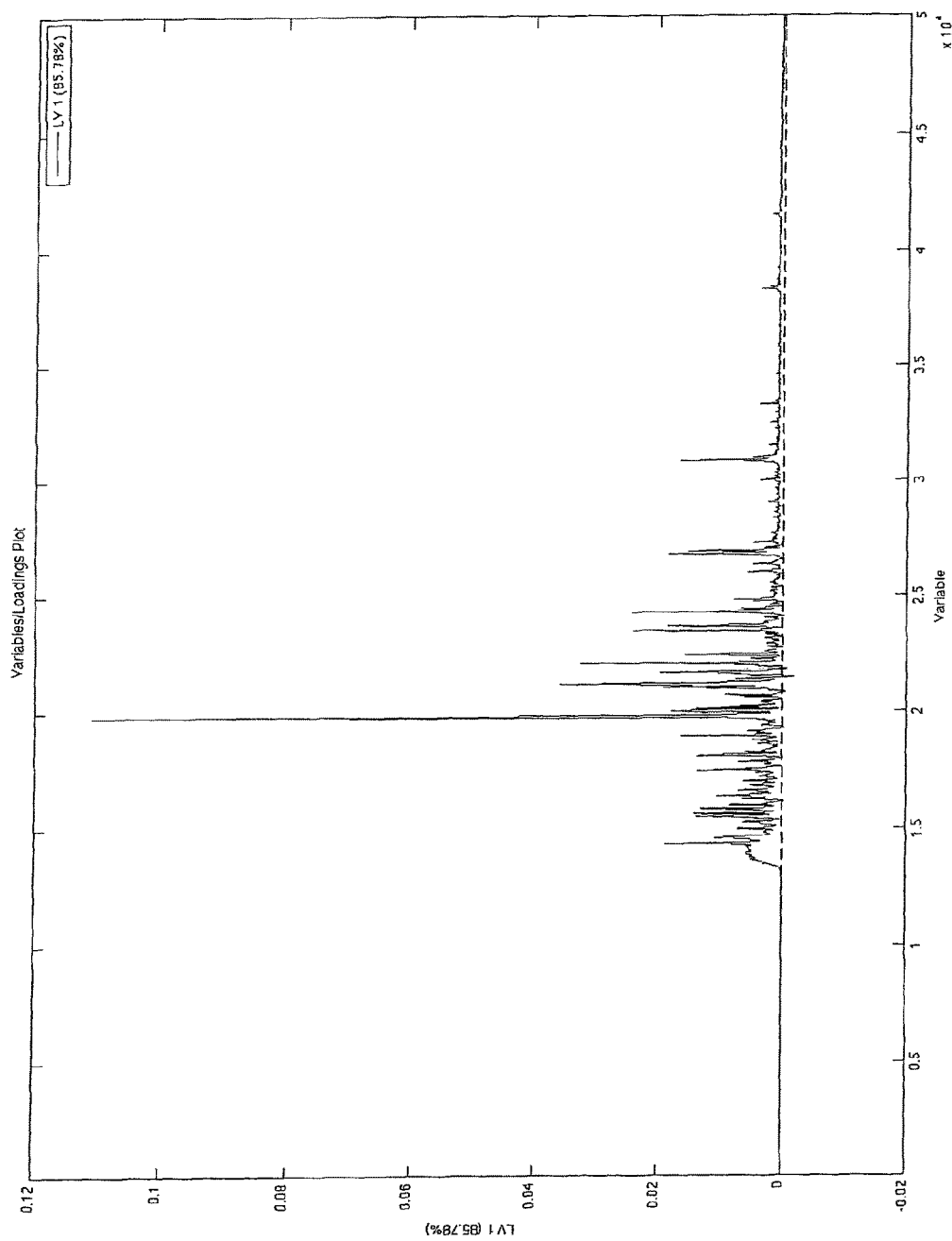
Figure 47:
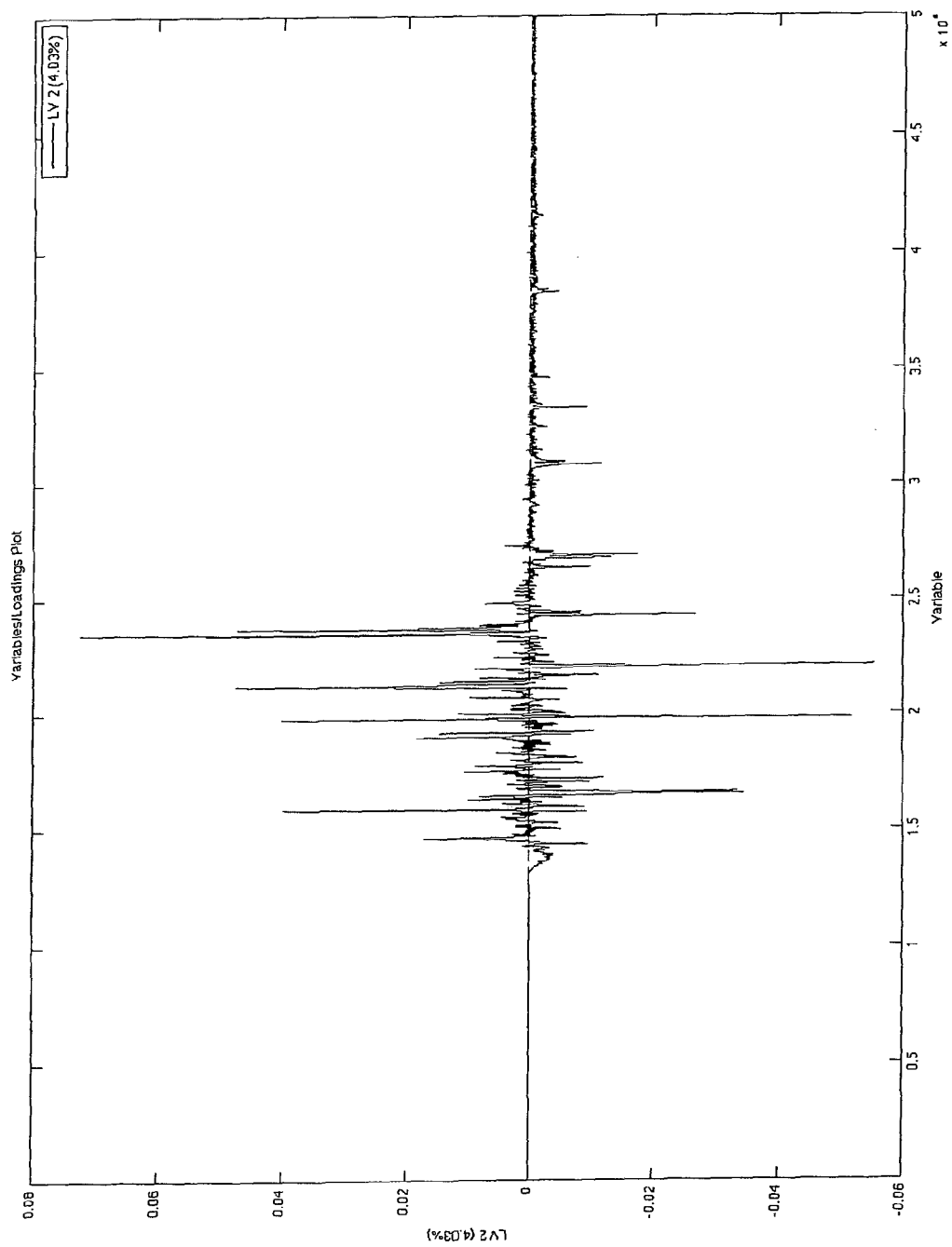

The final signal processing step performed is to remove parts of the signal known to contain no useful information. FIGS. 9a, 9b and 41 show the effect of removing the data points in the MS profile over the range from 0 to 500 m/z units, as the MALDI was set not to record intensities in this range. It is clear from the scores plot that no effect is observed by removing this data, as the scores plot is identical to that observed in FIGS. 8a 8b and 40.

Using in step c) a first signal processing method comprising the following steps of resampling, baseline correction, filtering, alignment, visual analysing and normalisation of the raw standard and/or sample MS data, the standard and sample MS profiles appear smoother and the peaks align more consistently across cell lines compared to MS profiles pretreated solely with the method steps of baseline correaction and normalisation (FIGS. 21a and 21b). Said method also results in more consistent MS profiles for biological replicates where 2 or 3 cell pellets were prepared for subjecting to MS analysis from the same sample. Preferably, these improvements do come at the cost of an increase in the time required to process the samples (approx. 2 h for approx. 400 spectra), however this is not preferably prohibitive in terms of a modelling approach and time required to predict/select those cell lines of interest during a cell line construction process.

EXAMPLE 6

Signal Processing Method 2

6.1 PLSDA Modelling of Productivity Metrics

PLSDA is an application of multivariate least squares modelling specifically formulated for predictive classification. The developed MS fingerprinting approach utilised in the example employs the PLS_Toolbox implementation of PLSDA, published by Eigenvector Research, Inc. (EVRI) (www.eigenvector.com).

6.2 Training a PLSDA Model

To train a PLSDA model, two different sets of information are required; the x-block and the y-block. In the outlined approach to performing a new cell line construction, the x-block contains the information from within the spectral profiles generated at the 96 DWP stage of the process. Each profile is treated as a sample, with the signal intensities recorded over a specific range of m/z values being treated as the variables. The y-block contains information assigning each of the training samples to a class variable. In this example the y-block contains information relating to specific cell culture data of productivity of a cell line at the bioreactor scale, i.e. product concentration, specific productivity or integral of viable cell count.

Using the x-block data, a PLS mapping of the original variables into the latent variable space is performed. This has the effect of reducing the dimensionality of the problem, whilst describing as much of the variability in the original data as possible. The PLSDA algorithm then utilises the information in the y-block to fit the linear discrimination boundary that best separates the x-block data based on the class information stored in the y-block. If there are only two classes described in the y-block, a single discrimination boundary is sufficient; in cases where three or more classes are present, the within class samples should be compared to the out of class samples for each available class.

6.3 Analysis Flowchart

Figure 10:
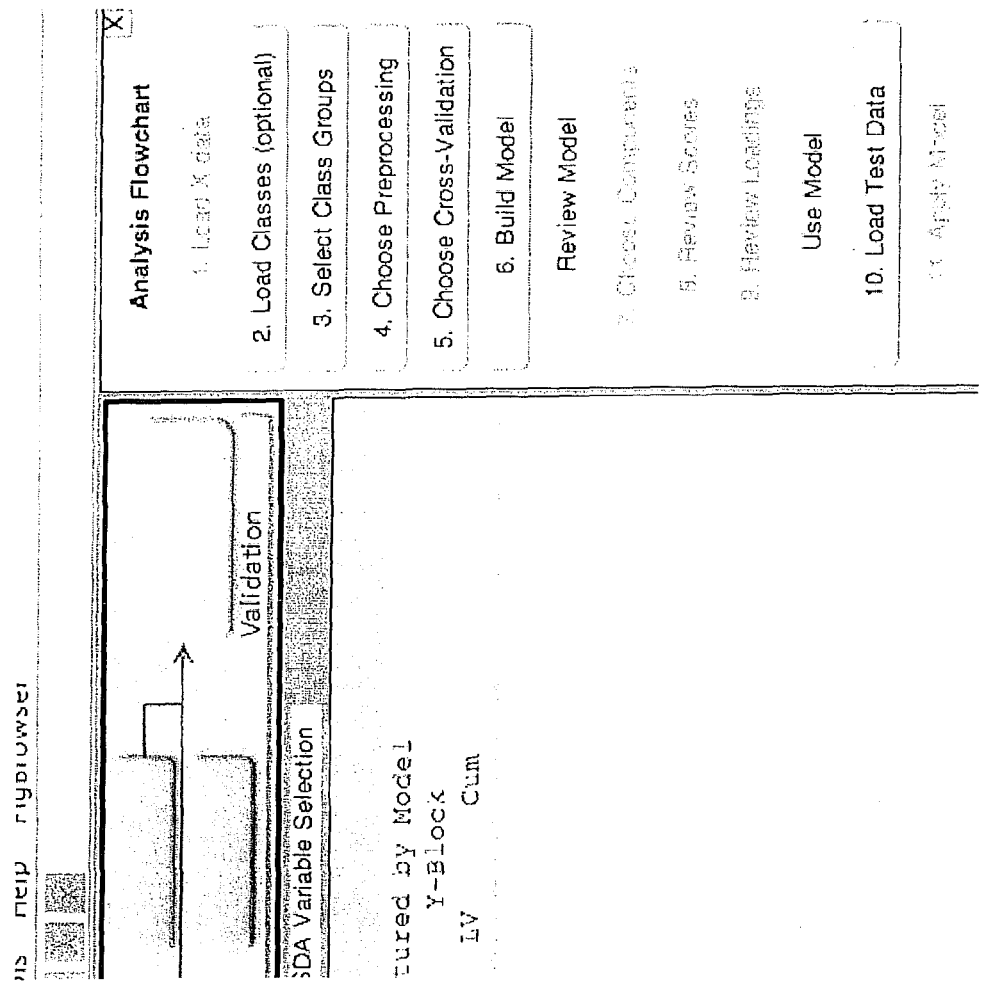
FIG. 10 shows the PLSDA analysis flow chart in the PLS_Toolbox.

FIG. 10 shows the flowchart of operations required to build a PLSDA model using the graphical implementation of the algorithm found in the MATLAB PLS_Toolbox.

Figure 11B:
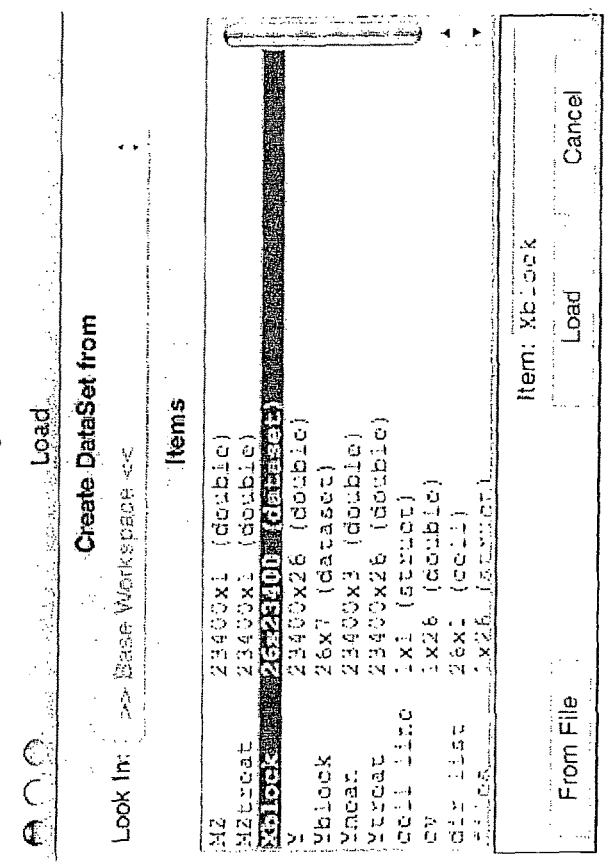
FIGS. 11a and 11b show the PLSDA import dialogue box in the PLS_Toolbox.
Figure 11A:
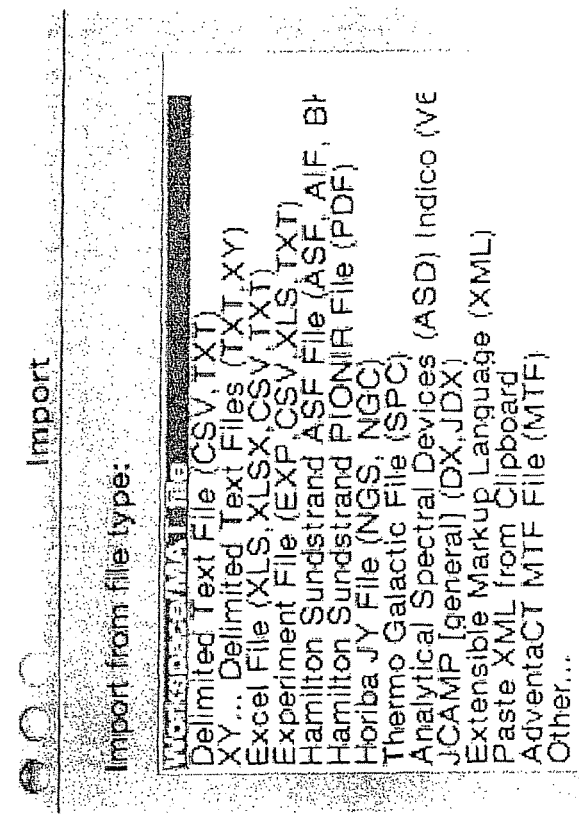
Figure 12:
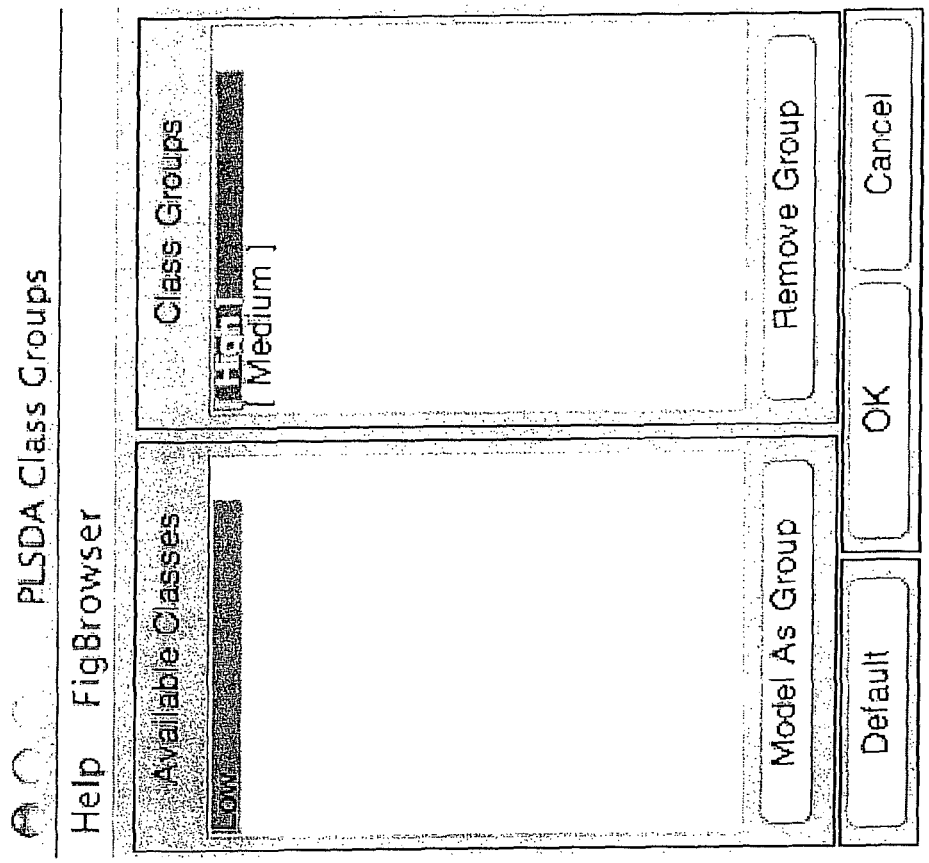
FIG. 12 shows PLSDA class group selection dialogue box in the PLS_Toolbox.
Figure 13:
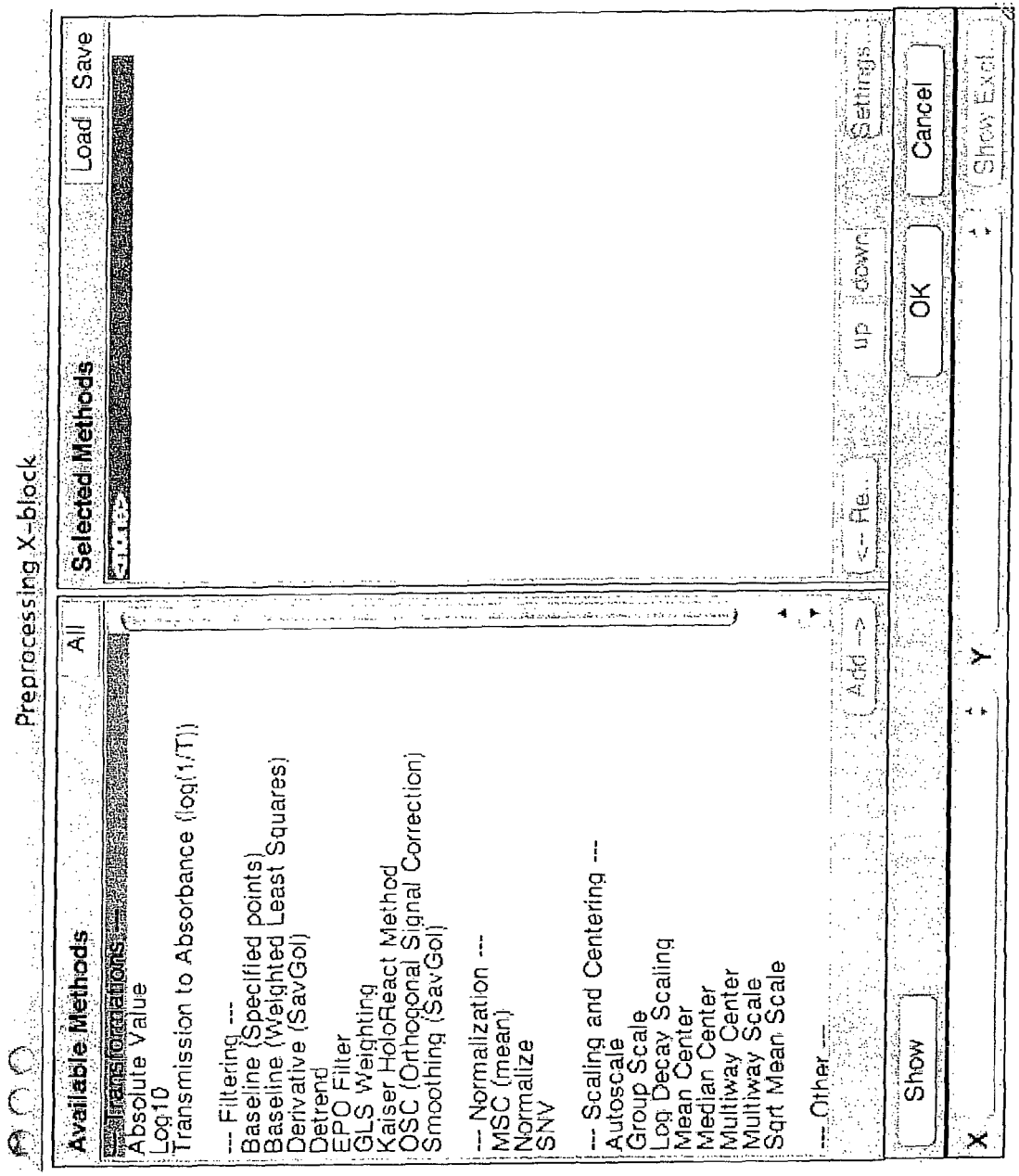
FIG. 13 shows PLSDA data re-processing options in the PLS_Toolbox.
Figure 14:
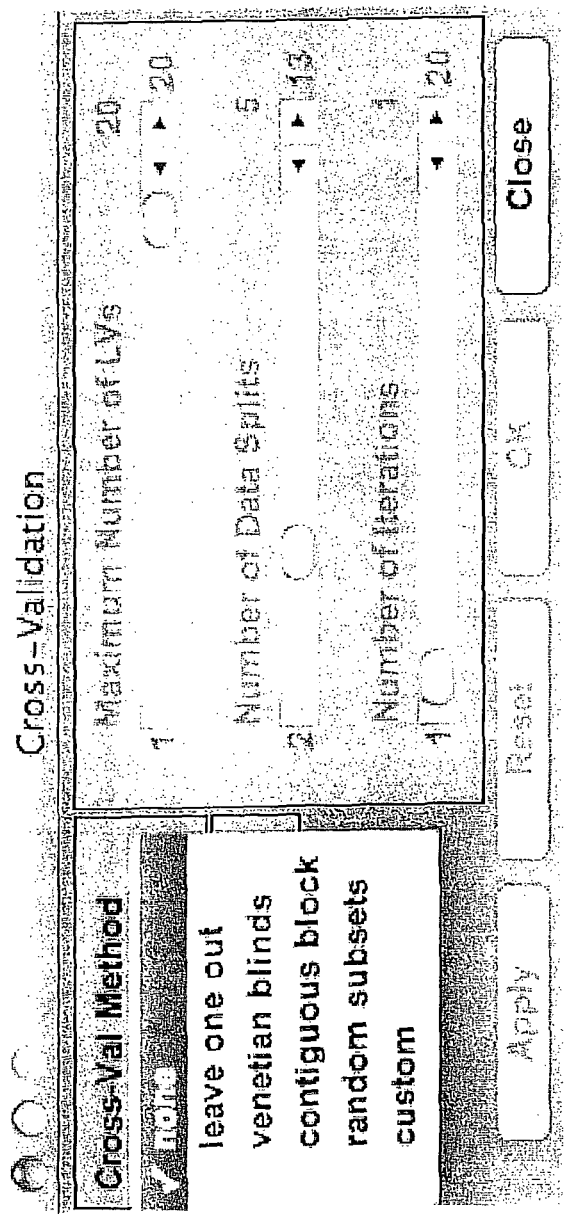
FIG. 14 shows PLSDA cross validation dialogue box in the PLS_Toolbox.
Figure 15A:
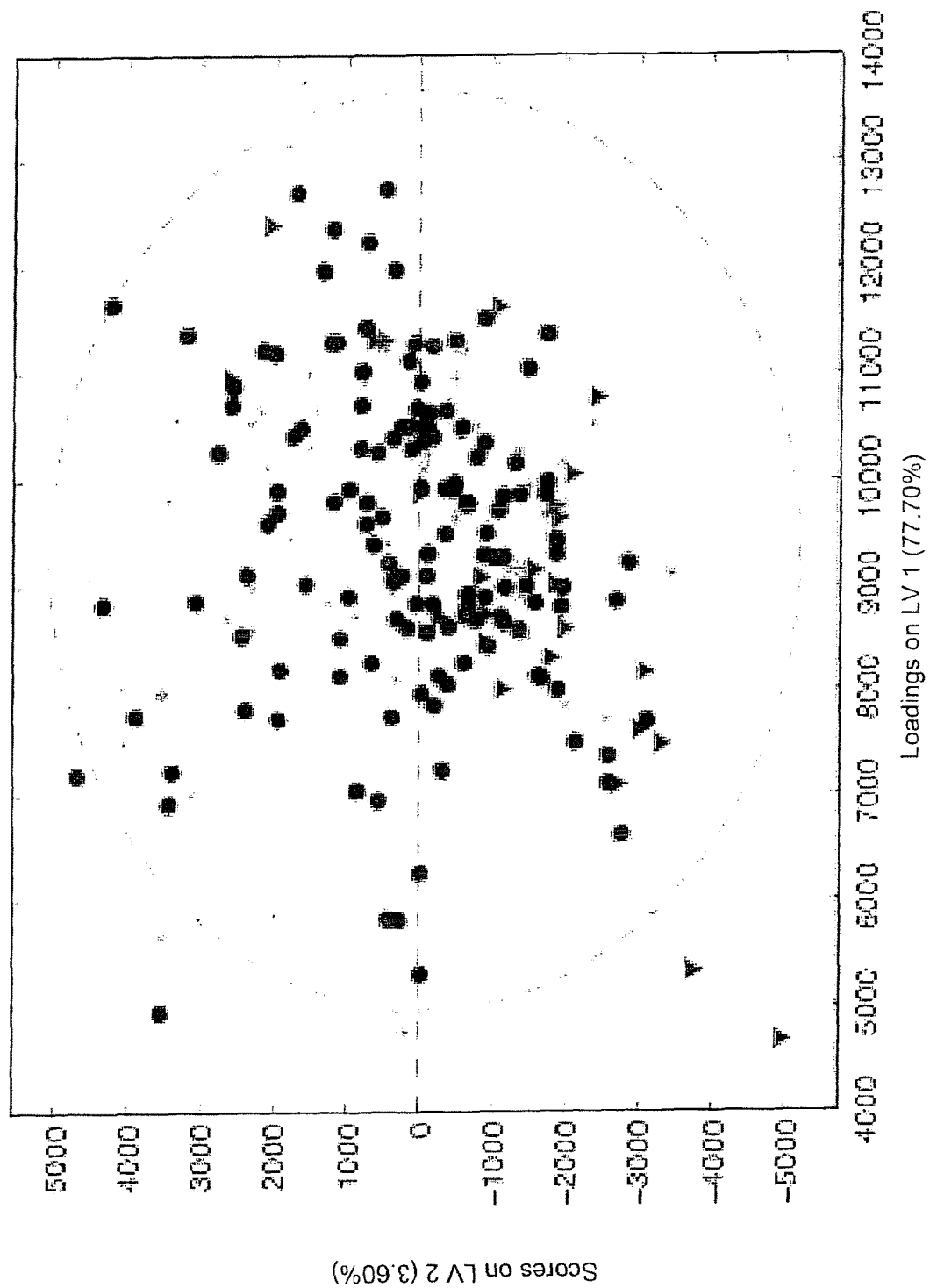
FIGS. 15a to 15d and 42 to 45 show various PLSDA scores plots: (15a, 42) Bivariate scores plot, (15b, 43) Hotelling's T2 plot, (15c, 44) Model predictions plot and (15d, 45) Model predictions probability plot.
Figure 15B:
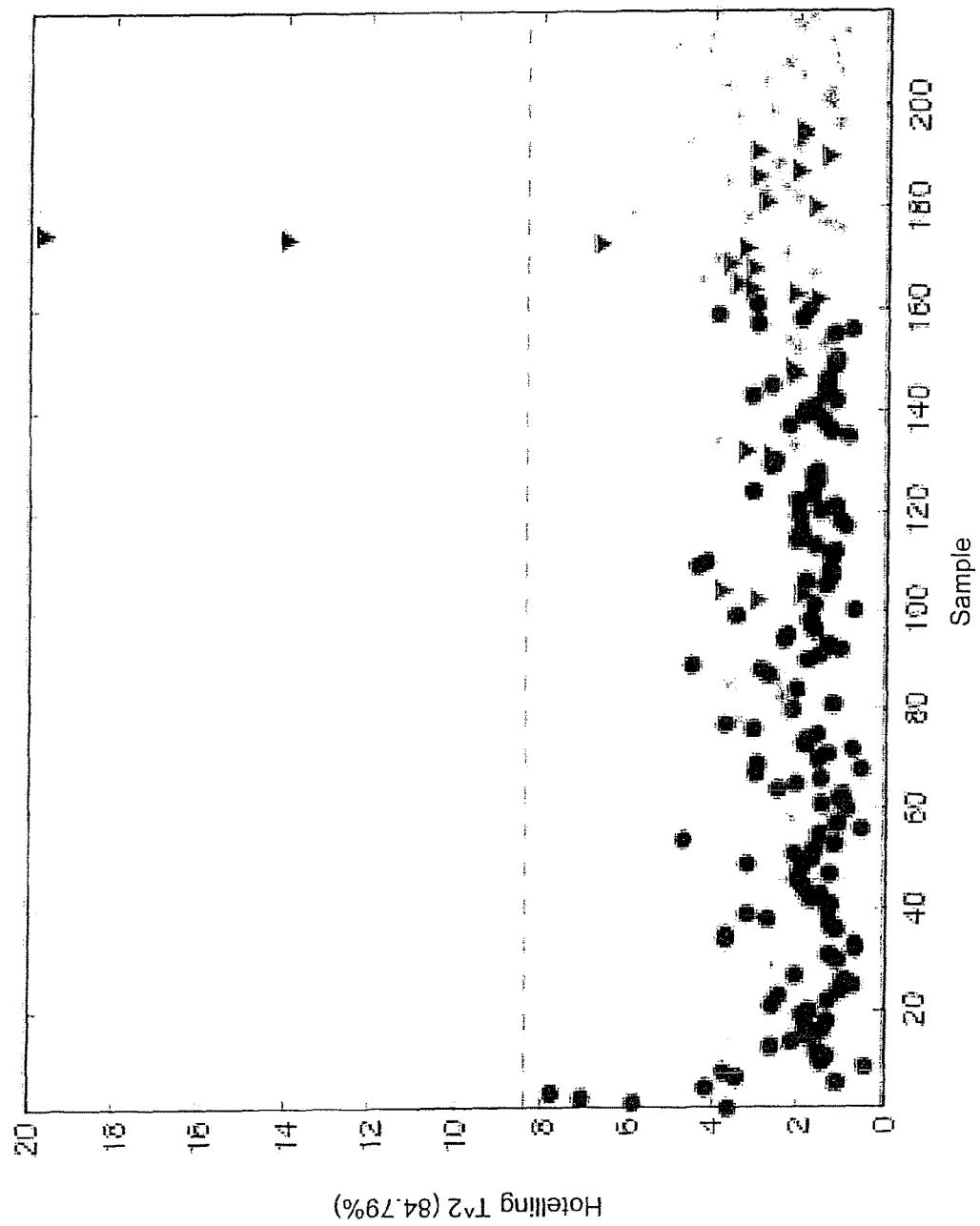
Figure 15C:
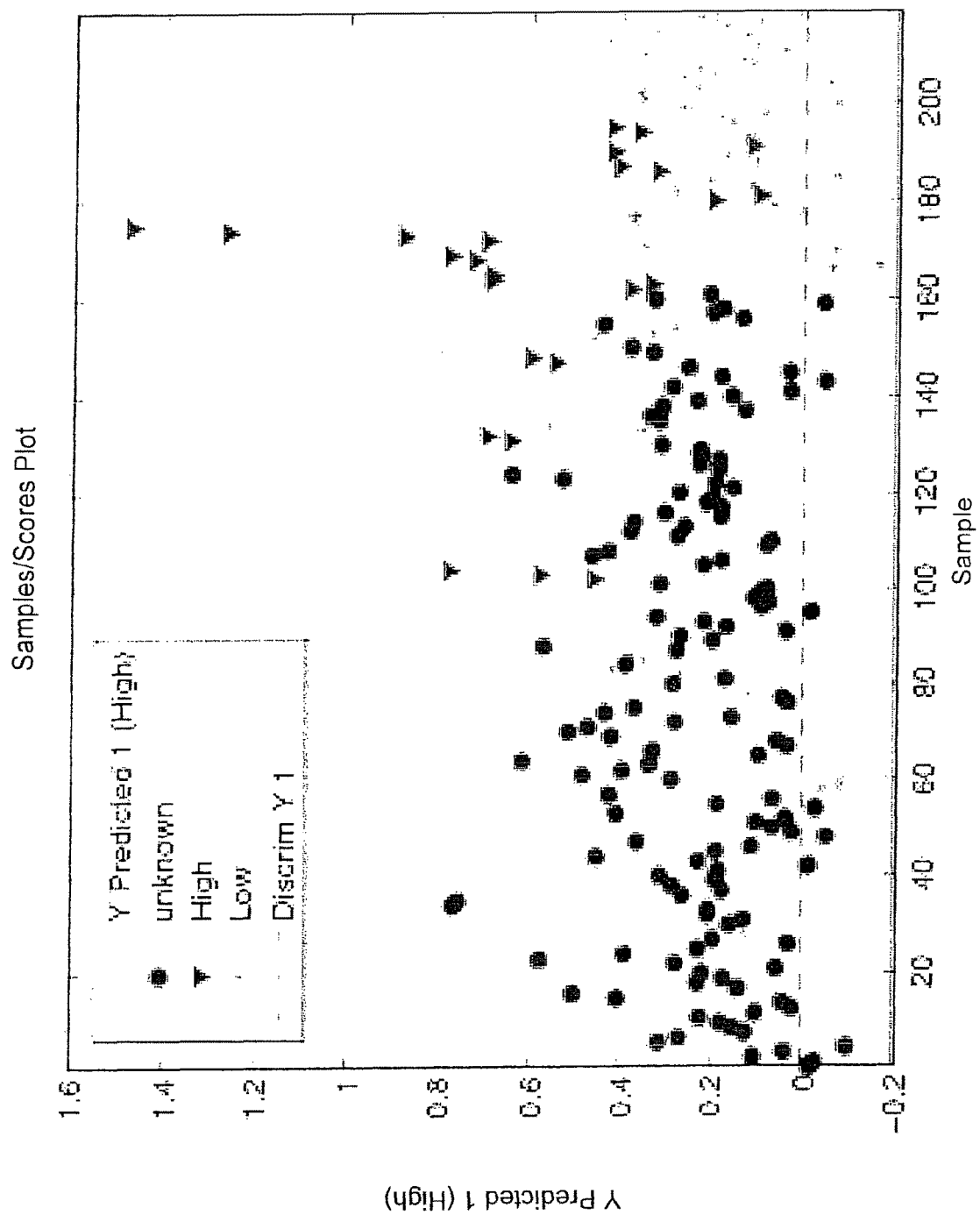
Figure 15D:
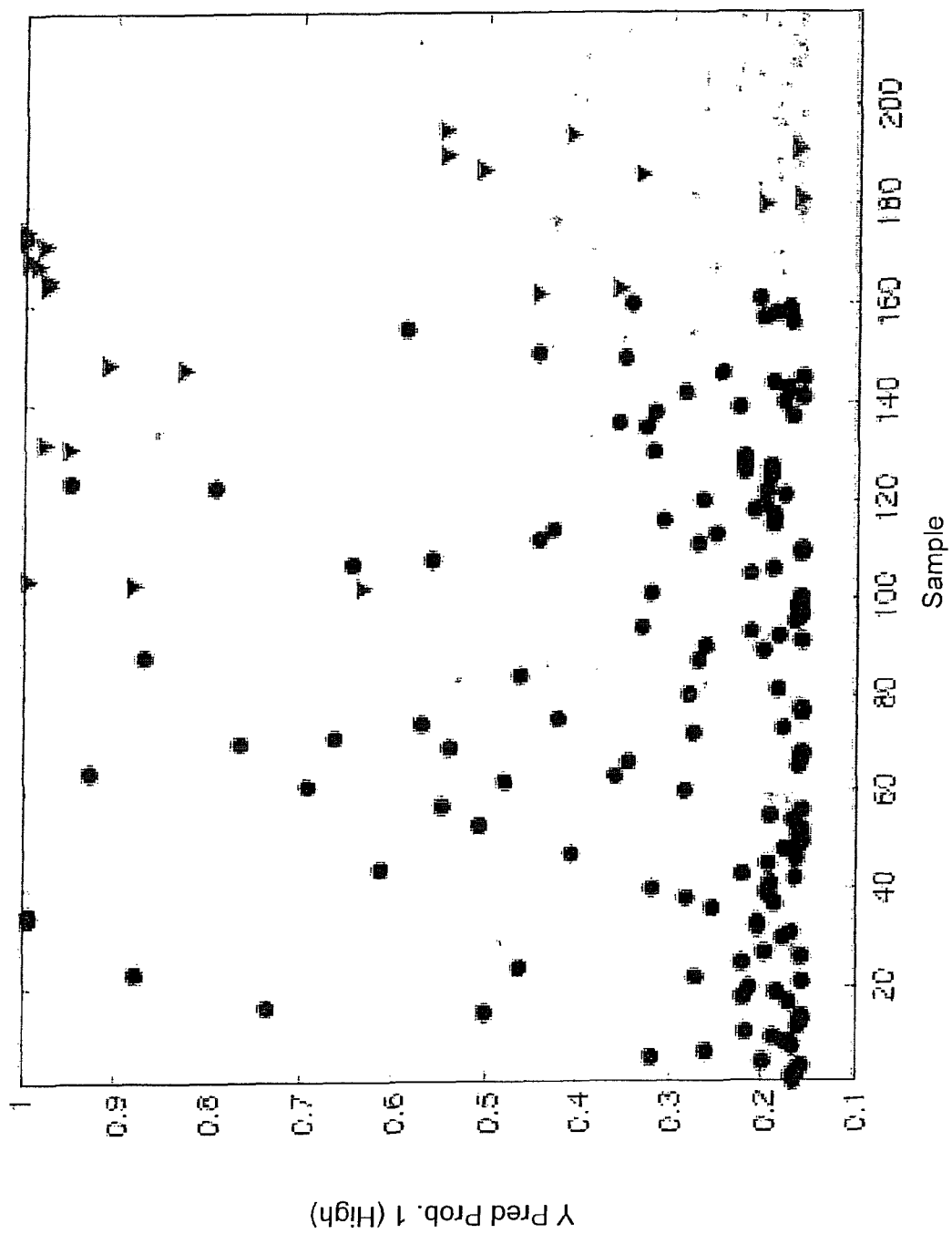
Figure 16A:
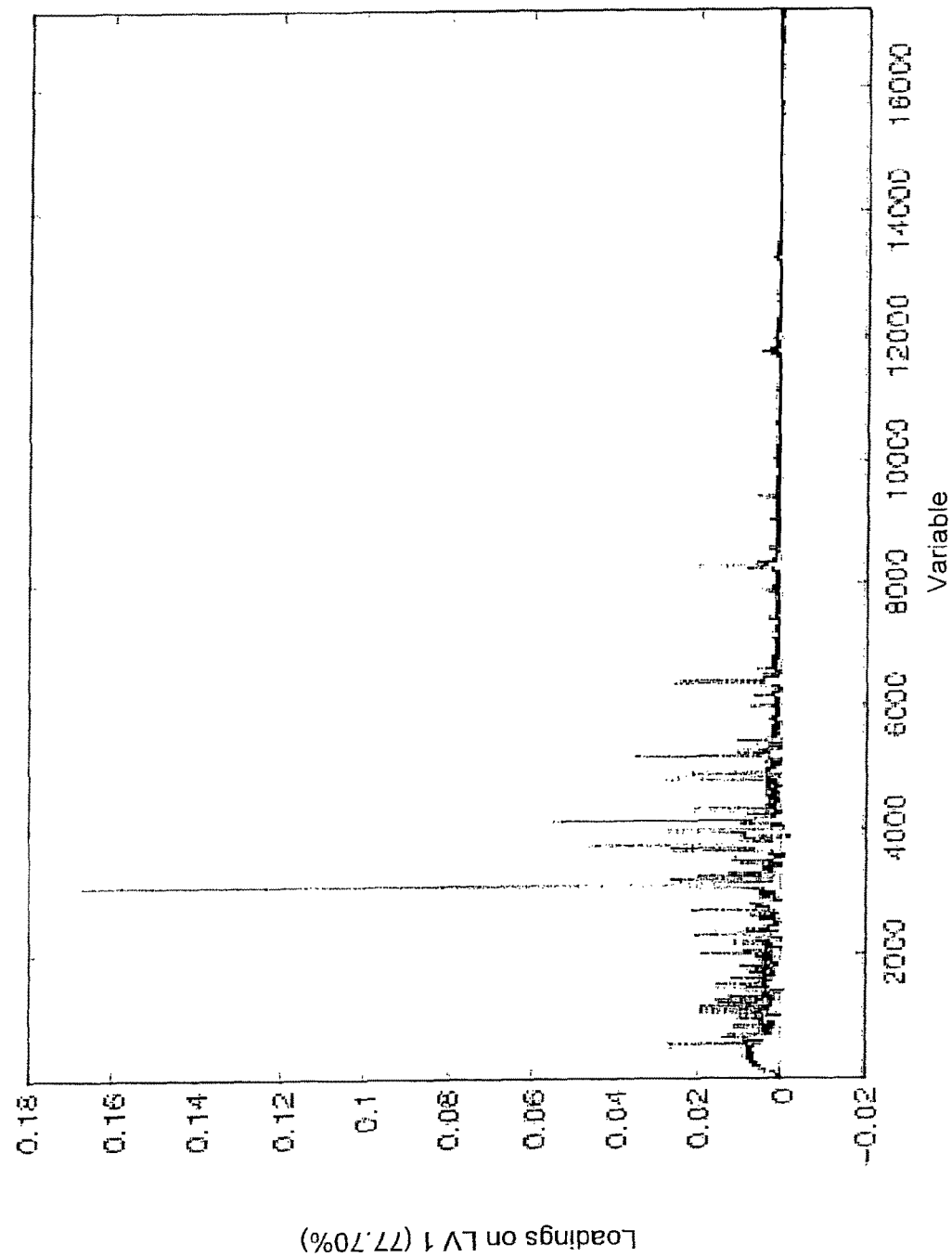
Figure 16B:
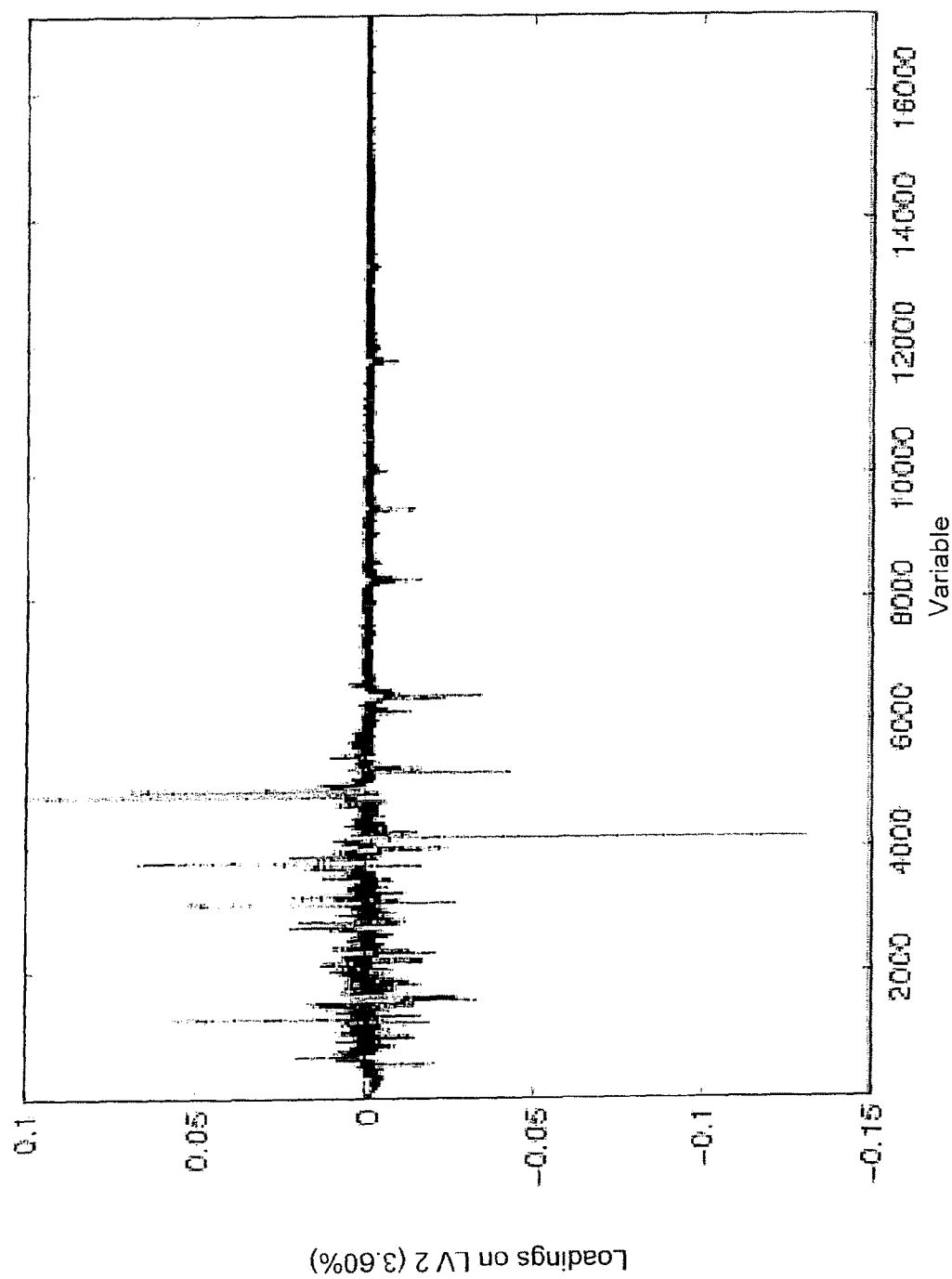

1. Load X data—This button prompts the user to import the x-block data into the software. The fingerprinting software, ms_preproc, is designed to act as an interface between the signal processing and analysis techniques, automatically converts the MS data into the required format to work with the PLS_Toolbox and saves the variable to the MATLAB workspace as the variable 'Xblock' (FIGS. 11a and 11b).
2. Load Classes (optional)—This button is used to import the y-block data into the software. However, class information can also be stored in the 'Xblock' variable (see http://wiki.eigenvector.com/index.php?title=DataSet_Object for more details). The ms_preproc software embeds the class information into the 'Xblock' variable; hence this step is optional.
3. Select Class Groups—This button presents the user with the option to select the class groups with which to build the model. FIG. 12 shows a typical example with three classes (high, medium, low). The model will calculate decision boundaries for the classes added to the right-hand column.
4. Choose Preprocessing—This button can be used to apply various preprocessing techniques to the spectra files (FIG. 13). If this step is performed using the spectral pre-processing tools in the bioinformatics toolbox, the majority of this step is optional. However, also related to preprocessing of the data is the issue of the prior probabilities assigned during training. By default the algorithm assume an equal probability that each class is selected. Sometime this is not the case, and the values must be adjusted to reflect the true probabilities. This is performed by altering the 'Method Options (PLSDA)', which is under the 'Options' section of the 'Edit' menu.
5. Choose Cross-Validation—This button allows the user to cross validate during the training process. This process is often used to provide an improved degree of confidence in a result and serves as a cross-check of classifier performance. The standard approach is to reserve a portion of the training data and use this to test the performance of the classifier. Typically, this process is then repeated with a different portion of data reserved. FIG. 14 shows the methods available for portioning the data using the PLS_toolbox (http://wiki.eigenvector.com/index.php?title=Using_Cross-Validation).
6. Build Model—This button calculates the PLS latent variables and places the optimum position of the discrimination boundaries so as to maximise the number of correct classifications within the training dataset.
7. Choose Components—This button becomes available once the PLSDA model has been calculated. It produces graphs to aid the user in the selection of the number of Latent Variables to retain in the PLSDA model. Another method to achieve this is to assume that the variation explained relative to the y-block should be in the region of 70-80% so as not to over-fit the model.
8. Review Scores—This button allows access to a number of plots related to the latent variable scores. These can be used to analyse the model performance. FIGS. 15a to 15d and 42 to 45 show some of the most useful graphs; (a) Bivariate Loadings Plot, (b) Hotelling's T2 plot, (c) Model Predictions Plot and (d) Associated Probabilities for the Model Predictions Plot.
9. Review Loadings—This button allows access to a number of plots related to the latent variable loadings. These can be used to identify the variables that have the most significant influence on each latent variable. This can be useful for identifying the areas of the spectral signal that are the most likely to influence discrimination.
10. Load Test Data—Once the model has been built, the next step is to utilise the models to make predictions about unseen data. Clicking this button presents the user with the same dialogue box as in FIGS. 11a/b. Test data can also be loaded in with the original x-block data in step 1 by not assigning a class variable to the samples. Any samples not assigned a class by our ms_preproc software during step 2 are automatically regarded as test data. These can be seen as the samples classed as unknown in FIGS. 16a, 16b, 46 and 47.
11. Apply model—This button fits the test data to the trained PLSDA model. It allows the user to determine the most probable class to which unknown samples will belong.

EXAMPLE 7

MS Profiles Subjected to MALDI-TOF and their Statistical Modelling

The paragraph exemplified focuses on results obtained from the modelling of the MS analysis data during the new cell line generation process. FIGS. 48, 49, 17 and 18 show the results obtained for the BNCD model (data are baseline corrected, normalised and cropped with duplicate samples included). The triangles (FIGS. 17 and 18) and stars (FIGS. 48 and 49) show the training data for the "High" class (>4000 mg/L), stars (FIGS. 17 and 18) and triangles (FIGS. 48 and 49) show the training samples for the "Low" class (≤3999 mg/L), black dots (FIGS. 17 and 18) and crosses (FIGS. 48 and 49) without a cell line ID number represent samples for which the class data is unknown and dots with cell line ID number show the samples that fall above the classification boundary (upper grey dotted line).

Using the processed information from the cell line construction process (i) a prediction model could be built including hundreds of MS data generated during the cell line generation process. Based on the model a list of the cell lines that were expected to produce different amount of MAb (>4000 mg/L; ≤3999 mg/L) was collated. Table 2 highlights several cell lines which can be identified in FIGS. 48, 49, 17 and 18. The cell lines were grown with their titre values recorded to measure the performance of the prediction method (Table 2).

TABLE 2

| Predicted high/low producing cell lines vs. observed productivity | | |
| --- | --- | --- |
| Cell line ID | Prediction | 10 L bioreactor |
| 262B7 | >4000 mg/L | 6524 mg/L |
| 281D8 | >4000 mg/L | 4555 mg/L |
| 241B6 | ≤3999 mg/L | 1219 mg/L |
| 243D11 | ≤3999 mg/L | 663 mg/L |
| 246F9 | ≤3999 mg/L | 964 mg/L |

The results of the validation run proofed the successful application of predictive cell line selection in the process of cell line generation, so that at early development stage collated MS profiles of individual cell lines reflect their behaviour at the later manufacturing scale.

EXAMPLE 8

The Results after the Statistical Modelling of MS Profiles Subjected to LC-ESI-MS The raw MS profiles obtained by LC-ESI-MS were signal processed by signal processing method I (example 5) and signal processing method II (example 6). The results were shown in FIGS. 19a/b and 20.

FIGS. 19a/b show the separation of three different recombinant CHO cell lines using a PLSDA analysis (FIGS. 19a/b show LV1 v LV3) and FIG. 20 shows the separation of seven different recombinant CHO cell lines after PLSDA analysis when the samples are grouped into <2 g/L and >2 g/L. The data shows two samples of each recombinant cell line group and that the PLSDA algorithm is capable of discriminating between cell lines belonging to different groups. The approach is suitable for fingerprinting recombinant cell lines on the basis of desirable (e.g. productivity) characteristics.

Table 3 shows the product concentration of the CHO cell lines 2, 42, 52, 75, 106, 144 and 164 cultivated in a 24 well plate, batch, fed batch and bioreactor. Especially, the product concentration at bioreactor scale was predicted correctly by the PLS-DA analysis using LC-ESI-MS data (FIG. 20).

TABLE 3

| CHO Cell line | Product conc. 24 well plate (mg/L) | Product conc. Batch (mg/L) | Product conc. Fed batch (mg/L) | Product conc. bioreactor scale (mg/L) | Grouping as shown in PLS-DA analysis of LC-ESI-MS data |
| --- | --- | --- | --- | --- | --- |
| 42 | 230 | 538 | 2404 | 3220.00 | >2 g/L |
| 52 | 31.5 | 31.5 | 101 | 24.00 | <2 g/L |
| 2 | 236 | 480 | 1680.5 | 2594.00 | >2 g/L |
| 144 | 175 | 391 | 1592 | 1816.00 | <2 g/L |
| 75 | 241 | 606 | 1001 | 1826.00 | <2 g/L |
| 106 | 221 | 766 | 969.5 | 2325.00 | >2 g/L |
| 164 | 202 | 534 | 881.5 | 2307.00 | >2 g/L |

EXAMPLE 9

Improving the Accuracy of Prediction 9.1 Bioreactor Round 1

In this first round, cell lines producing the antibody IgG XXX anti insulin have been conducted, unless otherwise specified, under the culture conditions as outlined in Example 1, first paragraph.

Then, said cell lines were subjected to a MS analysis to obtain raw sample MS data thereof, subsequently, the raw sample MS data were subjected to at least one first MS signal processing method comprising the steps of up-sampling, baseline correction, filtering, alignment and normalization to obtain pre-treated sample MS profiles and then the pre-treated sample MS profiles were subjected to a second data analysis comprising of a PLS-DA based comparative evaluation so as to predict the titre data in a bioreactor of the cell lines.

As pre-treated standard MS profiles MS data of cell lines producing the antibody IgG CB72.3 and pre-treated by baseline correction, normalisation and cropping, especially pretreated MS profiles of the cell lines in Table 2 (Example 7), are used. As titre data from a standard cell the titre data from cell lines producing the antibody IgG CB72.3, especially the titre data listed in Table 2 (Example 7), are used.

The Y predicted plot obtained by said method shows a set of cell lines would have been considered for bioreactor evaluation (FIG. 22). There is also a significant tail off of the validation data on the latent variables plot (FIG. 23) indicating that there may not be sufficient coverage of the data space in the model to accurately predict the titre of all cell lines.

Afterwards, the cell lines with the predicted titre data are cultivated in a cell culture so as to verify its titre data in a bioreactor. The bioreactor cultivation is carried out in a conventional manner.

The samples of the different cell lines were taken on the 15th day of bioreactor cultivation.

Table 4 shows the resultant titre data of the cell lines that were actually run in the first round of cultivation in a bioreactor.

TABLE 4

| Cell Line | Bioreactor titre data (mg/L) | Prediction from the method according to the present invention |
| --- | --- | --- |
| 025G12 | 7224 | 1/3 reps > 4 mg/ml |
| 929H9 | 7385 | 1/3 reps > 4 mg/ml |
| 897G3 | 2452 | 0/3 reps > 4 mg/ml |

The term "reps" means the repetitions of the preparations of one cell line to be subjected to MS analysis.

Under the term "x/3 reps>4 mg/ml", wherein x can be 0, 1, 2 or 3, is understood that in x cases of the three preparations of one cell line the PLS-DA based comparative evaluation predicts a titre data of more than 4 mg/ml.

9.2 Bioreactor Round 2

Bioreactor Round 2 has been carried out in the same way as specified in Example 9.1. However, as standard pre-treated MS profiles the pre-treated standard MS profiles of the Bioreactor Round 1 and the MS profiles of the cell lines, which titre data has been measured in the first run of bioreactors, have been included together with its measured titre data in the statistical program.

The Y predicted plot obtained by said method shows a different set of cell lines that would have been considered for bioreactor cultivation (FIG. 24) compared to FIG. 22. The tail off in the validation data is less pronounced on the latent variables plot compared to FIG. 23 (FIG. 25). However, it is still pronounced and the method implies a large number of cell lines will be high producers.

Table 5 shows the resultant titres of the cell lines that were actually run in the second round of bioreactors.

TABLE 5

| Cell Line | Bioreactor titre data (mg/L) | Prediction from the method according to the present invention |
| --- | --- | --- |
| 906G5 | 1311 | 1/2 reps > 4 mg/ml |
| 930C4 | 108 | 3/3 reps > 4 mg/ml |
| 934H6 | 1232 | 2/2 reps > 4 mg/ml |
| 952D9 | 79.1 | 2/2 reps > 4 mg/ml |
| 920D6 | 1911 | 3/3 reps > 4 mg/ml |
| 964E7 | 7591 | 2/3 reps > 4 mg/ml |

9.3 Bioreactor Round 3

Bioreactor Round 3 has been carried out in the same way as specified in Example 9.1. However, as standard pre-treated MS profiles the pre-treated standard MS profiles of the Bioreactor Round 1 and the MS profiles of the cell lines, which titre data has been measured in the first and second run of bioreactors, together with their measured titre data, have been included in the statistical program.

The Y predicted plot obtained by said method predicts that less cell lines will be high producers (FIG. 26). The tail off in the validation data shown in the latent variables plot (FIG. 27) is significantly reduced compared to FIG. 25. The prediction accuracy appears more reliable than the previous 2 rounds implying that the method is better fit to the data space than the previous ones.

Table 6 shows the resultant titres of the cell lines that were actually run in the third round of bioreactors.

TABLE 6

| Cell Line | Bioreactor titre data (mg/L) | Prediction from the method according to the present invention |
|---|---|---|
| 029D11 | 3074 | 1/3 reps > 4 mg/ml |
| 906B8 | 478 | 0/3 reps > 4 mg/ml |
| 917C3 | 2451 | 1/2 reps > 4 mg/ml |
| 946C4 | 823 | 0/3 reps > 4 mg/ml |
| 961H8 | 5660 | 2/2 reps > 4 mg/ml |
| 952C8 | 3959 | 2/3 reps > 4 mg/ml |

9.4 Bioreactor Round 4

Bioreactor Round 4 has been carried out in the same way as specified in Example 9.1. However, as standard pre-treated MS profiles the pre-treated standard MS profiles of the Bioreactor Round 1 and the MS profiles of the cell lines, which titre data has been measured in the first, second and third run of bioreactors, together with their measured titre data, have been included in the statistical program.

The Y predicted plot obtained by said method predicts fewer of the cell lines will be high producers (FIG. 28) compared to FIG. 26. The tail off in the validation data on the latent variables plot (FIG. 29) is again smaller that previously observed (for instance FIG. 27).

Table 7 shows the resultant titres of the cell lines that were actually run in the fourth round of bioreactors.

TABLE 7

| Cell Line | Bioreactor titre data (mg/L) | Prediction from the method according to the present invention |
|---|---|---|
| 896C7 | 5132 | 2/2 reps > 4 mg/ml |
| 931F12 | 1448 | 2/2 reps > 4 mg/ml |
| 933A8 | 731 | 0/2 reps > 4 mg/ml |
| 980F3 | 2428 | 0/2 reps > 4 mg/ml |
| 917G3 | 4463 | 0/2 reps > 4 mg/ml |
| 952F10 | 2083 | 2/2 reps > 4 mg/ml |

9.5 Bioreactor Round 5

Bioreactor Round 5 has been carried out in the same way as specified in Example 9.1. However, as standard pre-treated MS profiles the pre-treated standard MS profiles of the Bioreactor Round 1 and the MS profiles of the cell lines, which titre data has been measured in the first, second, third and fourth run of bioreactors, together with their measured titre data, have been included in the statistical program.

The Y predicted plot obtained by said method shows only a few cell lines being predicted to be high producers (FIG. 30). The tail off in the validation data on the latent variables plot (FIG. 31) did not show much variation from that of FIG. 29. Of the 5 cell lines that were run in this round, the model correctly classified 5 from 5, with 2 of the cell lines predicted to be high producers.

Table 8 shows the resultant titres of the cell lines that were actually run in the fifth round of bioreactors.

TABLE 8

| Cell Line | Bioreactor titre data (mg/L) | Prediction from the method according to the present invention |
|---|---|---|
| 033D5 | 6024 | 2/2 reps > 4 mg/ml |
| 016F11 | 2519 | 0/2 reps > 4 mg/ml |
| 016B5 | 116 | 0/2 reps > 4 mg/ml |
| 033G5 | 4155 | 2/3 reps > 4 mg/ml |
| 948G2 | 1592 | 0/2 reps > 4 mg/ml |

EXAMPLE 10

The cell lines were prepared and cultivated as outlined in Example 9.

The term "Bioreactor Round X", where X is 3, 4 and 5, means the same run of a bioreactor under the same cultivation conditions for both examples 9 and 10.

For the PLS-DA based comparative evaluation a 3 class PLS-DA model was built using both the integral viable cell count (IVC) and the cell specific productivity (qP) data. In both models the desired class was the Medium class. The class boundaries were defined as follows:

IVC Model:

High>$4500 \times 10^6$ cells×h/ml $4500 \times 10^6$ cells×h/ml>Medium>$3250 \times 10^6$ cells×h/ml Low<$3250 \times 10^6$ cells×h/ml qP Model:

High>2.35 pg×cell×h 2.35 pg×cell×h>Medium>1.75 pg×cell×h

Low<1.75 pg×cell×h

Based on the conditions and settings mentioned above a PLS-DA based comparative evaluation was performed to predict the cell culture performance data, namely the integral viable cell count data (IVC) and the cell specific productivity data (qP).

Additionally, the IVC and qP data of the cell lines were determined, when the cell lines were cultivated in the bioreactor.

10.1 Prediction of the Integral Viable Cell Count Data (IVC)

As pre-treated standard MS profiles for the prediction of Bioreactor Rounds 3 to 5 MS data of cell lines producing the antibody IgG CB72.3 and pre-treated by baseline correction, normalisation and cropping, especially pre-treated MS profiles the cell lines in Table 2 (Example 7), and pre-treated MS profiles of cell lines cultivated in the Bioreactor Rounds 1 and 2 are used. As integral viable cell count data from a standard cell the integral viable cell count data from cell lines producing the antibody IgG CB72.3, especially from the cell lines in Table 2 (Example 7), and the integral viable cell count data of the cell lines cultivated in the Bioreactor Rounds 1 and 2 are used.

10.1.1 Bioreactor Round 3

FIG. 32 shows an IVC Y Predicted plot for cell lines Round 3 Predictions using the pre-treatment of raw MS data according to the present invention and subsequent PLS-DA modelling.

Table 9 shows the observed IVC values of the cell lines that were actually run in the third round of bioreactors.

TABLE 9

| Cell Line | IVC data ($\times 10^6$ cells $\times$ h/ml) | Prediction from the method according to the present invention ($\times 10^6$ cells $\times$ h/ml) |
| --- | --- | --- |
| 029D11 | 1417 | 4500 > 1/3 reps > 3250 |
| 906B8 | 1686 | 4500 > 3/3 reps > 3250 |
| 917C3 | 2748 | 4500 > 2/3 reps > 3250 |
| 946C4 | 3107 | 4500 > 1/3 reps > 3250 |
| 961H8 | 3873 | 4500 > 3/3 reps > 3250 |
| 952C8 | 2039 | 4500 > 0/2 reps > 3250 |

Under the term "4500>x/3 reps>3250", wherein x can be 0, 1, 2 or 3, is understood that in x cases of the three preparations of one cell line the PLS-DA based comparative evaluation predicts a IVC data between 4500 and 3250.

10.1.2 Bioreactor Round 4

FIG. 33 shows an IVC Y Predicted plot for cell lines Round 4 Predictions using the pre-treatment of raw MS data according to the present invention and subsequent PLS-DA modelling.

Table 10 shows the observed IVC values of the cell lines that were actually run in the fourth round of bioreactors.

TABLE 10

| Cell Line | IVC data ($\times 10^6$ cells $\times$ h/ml) | Prediction from the method according to the present invention ($\times 10^6$ cells $\times$ h/ml) |
| --- | --- | --- |
| 896C7 | 4043 | 4500 > 2/2 reps > 3250 |
| 931F12 | 2730 | 4500 > 1/2 reps > 3250 |
| 933A8 | 1812 | 4500 > 0/2 reps > 3250 |
| 980F3 | 3067 | 4500 > 1/2 reps > 3250 |
| 917G3 | 4057 | 4500 > 0/2 reps > 3250 |
| 952F10 | 3026 | 4500 > 1/2 reps > 3250 |

10.1.3 Bioreactor Round 5

FIG. 34 shows an IVC Y Predicted plot for cell lines Round 5 Predictions using the pre-treatment of raw MS data according to the present invention and subsequent PLS-DA modelling.

Table 11 shows the observed IVC values of the cell lines that were actually run in the fifth round of bioreactors.

TABLE 11

| Cell Line | IVC data ($\times 10^6$ cells $\times$ h/ml) | Prediction from the method according to the present invention ($\times 10^6$ cells $\times$ h/ml) |
| --- | --- | --- |
| 033D5 | 4859 | 4500 > 2/2 reps > 3250 |
| 016F11 | 3472 | 4500 > 1/2 reps > 3250 |
| 016B5 | 3553 | 4500 > 0/2 reps > 3250 |
| 033G5 | 3125 | 4500 > 3/3 reps > 3250 |
| 948G2 | 2008 | 4500 > 0/2 reps > 3250 |

10.2 Prediction of the Cell Specific Productivity Data (qP)

As pre-treated standard MS profiles for the prediction of Bioreactor Rounds 3 to 5 MS data of cell lines producing the antibody IgG CB72.3 and pre-treated by baseline correction, normalisation and cropping, especially the pre-treated MS profiles of the cell lines in Table 2 (Example 7), and pre-treated MS profiles of cell lines cultivated in the Bioreactor Rounds 1 and 2 are used. As cell specific productivity data from a standard cell the cell specific productivity data from cell lines producing the antibody IgG CB72.3, especially from the cell lines in Table 2 (Example 7), and the cell specific productivity data of the cell lines cultivated in the Bioreactor Rounds 1 and 2 are used.

10.2.1 Bioreactor Round 3

FIG. 35 shows a qP Y Predicted plot for cell lines Round 3 Predictions using the pre-treatment of raw MS data according to the present invention and subsequent PLS-DA modelling.

Table 12 shows the observed qP values of the cell lines that were actually run in the third round of bioreactors.

| Cell Line | qP data (pg $\times$ cell $\times$ h) | Prediction from the method according to the present invention (pg $\times$ cell $\times$ h) |
| --- | --- | --- |
| 029D11 | 2.17 | 2.35 > 3/3 reps > 1.75 |
| 906B8 | 0.28 | 2.35 > 1/3 reps > 1.75 |
| 917C3 | 0.89 | 2.35 > 1/3 reps > 1.75 |
| 946C4 | 0.26 | 2.35 > 0/3 reps > 1.75 |
| 961H8 | 1.46 | 2.35 > 3/3 reps > 1.75 |
| 952C8 | 1.94 | 2.35 > 1/3 reps > 1.75 |

Under the term "2.35>x/3 reps>1.75", wherein x can be 0, 1, 2 or 3, is understood that in x cases of the three preparations of one cell line the PLS-DA based comparative evaluation predicts a qP data between 2.35 and 1.75.

10.2.2 Bioreactor Round 4

FIG. 36 shows a qP Y Predicted plot for cell lines Round 4 Predictions using the pre-treatment of raw MS data according to the present invention and subsequent PLS-DA modelling.

Table 13 shows the observed qP values of the cell lines that were actually run in the fourth round of bioreactors.

TABLE 13

| Cell Line | qP data (pg $\times$ cell $\times$ h) | Prediction from the method according to the present invention (pg $\times$ cell $\times$ h) |
| --- | --- | --- |
| 896C7 | 1.27 | 2.35 > 2/2 reps > 1.75 |
| 931F12 | 0.53 | 2.35 > 1/2 reps > 1.75 |
| 933A8 | 0.40 | 2.35 > 2/2 reps > 1.75 |
| 980F3 | 0.79 | 2.35 > 0/2 reps > 1.75 |
| 917G3 | 1.10 | 2.35 > 0/2 reps > 1.75 |
| 952F10 | 0.69 | 2.35 > 2/2 reps > 1.75 |

10.2.3 Bioreactor Round 5

FIG. 37 shows a qP Y Predicted plot for cell lines Round 5 Predictions using the pre-treatment of raw MS data according to the present invention and subsequent PLS-DA modelling.

Table 14 shows the observed qP values of the cell lines that were actually run in the fifth round of bioreactors.

TABLE 14

| Cell Line | qP data (pg $\times$ cell $\times$ h) | Prediction from the method according to the present invention (pg $\times$ cell $\times$ h) |
| --- | --- | --- |
| 033D5 | 1.24 | 2.35 > 0/2 reps > 1.75 |
| 016F11 | 0.73 | 2.35 > 1/2 reps > 1.75 |
| 016B5 | 0.03 | 2.35 > 0/2 reps > 1.75 |
| 033G5 | 1.33 | 2.35 > 2/3 reps > 1.75 |
| 948G2 | 0.79 | 2.35 > 0/2 reps > 1.75 |

10.3 Summary

The FIGS. 32 to 37 and the Tables 9 to 14 show that the IVC and qP bioreactor performance data of cell lines cultivated in a 96 deep well plate can be predicted in an accurate way by the method according to the present invention.

The invention claimed is:

1. A process for the prediction of cell culture performance data of at least one sample cell, the process comprising:
   (a) providing a sample of the at least one sample cell, cell culture performance data from a standard cell cultivated in a large volume bioreactor containing a volume of media of at least 10 L and raw standard MS (mass spectrometric) data from the standard cell, wherein the at least one sample cell is cultivated in medium with a low volume of 1 µL to 1 L,
   (b) subjecting the sample of the at least one sample cell to a MS analysis after 1 to 5 hours of acclimatization at a temperature of 0° C. to 10° C. to obtain raw sample MS data thereof,
   (c) subjecting the raw standard and the raw sample MS data to at least one first MS signal processing method to obtain pre-treated standard and sample MS profiles,
   (d) subjecting the cell culture performance data from the standard cell of (a) and the pre-treated standard and sample MS profiles obtained in (c) to a second MS signal processing method including a PLS-DA (partial least squares discriminant analysis) based comparative evaluation so as to directly predict the cell culture performance data of the at least one sample cell at a later stage of up-scaling in a large volume bioreactor containing a volume of medium of at least 10 L, and
   (e) cultivating the cell line in a bioreactor containing a volume of medium of at least 10 L when the at least one sample cell is determined to have a cell specific productivity of at least 0.1 g protein/L/h,
   wherein the cell culture performance data are cell specific productivity, integral viable cell count or cell product concentration data,
   and wherein the method further comprises, prior to (a): generating a cell line that expresses a recombinant protein; and cultivating the cell line in a medium with the low volume of 1 µL to 1 L, wherein the sample of the at least one sample cell is taken from the cell line.

2. The process according to claim 1, wherein the cell is selected from a group consisting of human cell lines, animal cell lines, plant cell lines, cells from fungi, cells from bacteria, cells from yeast and stem cells.

3. The process according to claim 1, wherein the cell is a CHO cell line or a CHO-K1 cell line.

4. The process according to claim 1, wherein the MS analysis in (b) is MALDI-TOF.

5. The process according to claim 1, wherein the sample of the sample cells subjected to (b) comprises from $0.015 \times 10^6$ to $0.0625 \times 10^6$ cells.

6. The process according to claim 1, wherein the raw sample MS data obtained in (b) and the raw standard MS data provided in (a) are signal processed by an operation selected from the group consisting of baseline correction, normalisation, alignment, filtering and cropping.

7. The process according to claim 1, wherein the pre-treated standard and sample MS profiles obtained in (c) are optically analysed.

8. The process according to claim 1, wherein the sample cell with the predicted cell culture performance data evaluated in (d) is cultivated in a cell culture in a large volume bioreactor containing a volume of media of at least 10 L so as to verify its cell culture performance data.

9. The process according to claim 8, wherein the raw sample MS profiles obtained in (b) and the verified cell culture performance data of the sample cell in a large volume bioreactor containing a volume of media of at least 10 L are used in (a) as standard MS data and cell culture performance data from a standard cell.

10. The process according to claim 1, in combination with a method of isolating a cell with desired cell culture performance data, further comprising:
    isolating a desired cell having a desired cell culture performance data.

11. The process according to claim 1, wherein the medium with low volume has a volume of 1 µL to 1 mL.

12. The process according to claim 1, wherein the at least one sample cell is cultivated in a medium having a cell concentration of from $10^4$ to $10^8$ cells/mL culture medium.

13. The process according to claim 1, wherein the large volume bioreactor contains a volume of medium of at least 100 L.

14. The process according to claim 1, wherein the recombinant protein is an antibody, an antibody fragment, or a fused antibody.

* * * * *